United States Patent

Andersen et al.

Patent Number: 5,492,892
Date of Patent: Feb. 20, 1996

[54] ENDOTHELIN ANTAGONISTS

[76] Inventors: Thomas T. Andersen, 15 Catalpa Dr.; Michael J. Spinella, 132 Cardinal Ave., both of Albany, N.Y. 12209

[21] Appl. No.: 243,728

[22] Filed: May 17, 1994

Related U.S. Application Data

[63] Continuation of Ser. No. 666,294, Mar. 8, 1991, abandoned.

[51] Int. Cl.$^6$ .............. A61K 38/16; C07K 14/00
[52] U.S. Cl. .............. 514/13; 530/326; 530/324; 530/317; 514/9
[58] Field of Search .............. 530/317, 324; 514/9, 13

[56] References Cited

U.S. PATENT DOCUMENTS

4,981,950  1/1991  Masaki et al. .......... 530/326
5,114,918  5/1992  Ishikawa et al. ........ 514/11

FOREIGN PATENT DOCUMENTS

0310887  9/1988  European Pat. Off.
0315118  11/1988  European Pat. Off.
0366016  10/1989  European Pat. Off.
0421284  9/1990  European Pat. Off.

OTHER PUBLICATIONS

Spinella, M. et al., Proc. Natl. Acad. Sci. (USA) 88: 7443–7446 (Aug. 1991).
Gu, Xin et al. Biochem. Biophys. Res. Commun. 179: 130–133, (1991).
Fabregat, I. et al. Journal of Cellular Physiol. 145: 88–94 (1990).
Nakajima, et al., Structure–Activity Relationship of Endothelin: Importance of Charged Groups, Biochemical and Biophysical Research Communications, vol. 163, No. 1, 1989, pp. 424–429.
Topouzis, et al., Effects of calcium entry blockers on contractions evoked by endothelin–1, [Ala$^{3,11}$]endothelin–1 and [Ala$^{1,15}$]endothelin–1 rat isolated aorta, Br. J. Pharmacol., 1989, 98, 669–677.
Rovero, et al. Structure–activity studies on endothelin (16–21), the C–terminal hexapeptide of the endothelins, in the guinea–pig bronchus, Br. J. Pharmacol (1990), 101, 232–234.
Spinella, et al., A Proposed Structrual Model of Endothelin, Peptide Research, vol. 2, No. 4 (1989) pp. 286–291.
Randall, et al., Vascular activities of endothelin–1 and same alanyl substituted analogues in resistance beds of the rat, Br. J. Pharmacol, 1989, 98, 685–699.
Maggi, et al., The activity of peptides of the endothelin family in various mammalian smooth muscle preparations, European Journal of Pharmacology, 174, 1989, pp. 23–31.
Kitazumi, et al., Structure–activity relationship in vasoconstrictor effects of sarafotoxins and endothelin–1, Febs letters, 1990, vol. 260, No. 2, 269–272.
Hiley, et al, Binding of [$^{125}$I]–endothelin–1 to rat cerebellar homogenates and its reaction with some analogues, Br. J. Pharmacol., 1990, 101, 319–324.
Takasaki, et al., Structure–Receptor Binding Relationships of Sarafotoxin and Endothelin in Procine Cardiovascular Tissue, Biochemistry International, vol. 21, No. 6, Sep. 1990 pp. 1059–1064.
Hirata, et al., Receptor Binding Activity and Cytosolic Free Calcium Response by Synthetic Endothelin Analogs in Cultured Rat Vascular Smooth Muscle Cells, Biochemical and Biophysical Research Communications, vol. 160, No. 1, 1989, pp. 228–234.
Kimura, et al., Structure–Activity Relationships of Endothelin: Importance of the C–Terminal Moiety, Biochemical and Biophysical Research Communications, 1988, vol. 156, No. 3, pp. 1182–1186.
Yanagisawa, et al., Molecular biology and biochemistry of the endothelins, TiPS, Sep. 1989, vol. 10, pp. 374–378.
Moon, et al., Endothelin–like pulmonary vasoconstrictor peptide release by alpha–thrombin, Proc. Natl. Acad. Sci. USA, 1989, 86 pp. 9529–9533.

*Primary Examiner*—Jill Warden
*Assistant Examiner*—Benet Prickril
*Attorney, Agent, or Firm*—Scully, Scott, Murphy & Presser

[57] ABSTRACT

The present invention as directed to a compound which comprises an endothelin antagonist polypeptide that is at least 40% homologous to an endothelin active peptide, consisting of Et-1, Et-2, Et-3, SC, SA and SB and has the formula:

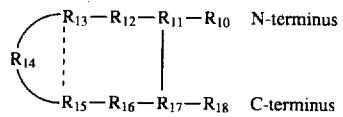

and pharmaceutically acceptable salts.

15 Claims, 1 Drawing Sheet

SEQUENCE LISTING ( 1 ) GENERAL INFORMATION:

( i i i ) NUMBER OF SEQUENCES: 84

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( D ) TOPOLOGY: both ( i i ) MOLECULE TYPE: peptide ( x i ) SEQUENCE DESCRIPTION: SEQ ID NO:1:

Cys Ser Cys Ser Ser Leu Met Asp Lys Glu Cys Val Tyr Phe Cys His
1               5                   10                  15
Leu Asp Ile Ile Trp
            20

( 2 ) INFORMATION FOR SEQ ID NO:2:

( i ) SEQUENCE CHARACTERISTICS:
        ( A ) LENGTH: 21 amino acids
        ( B ) TYPE: amino acid
        ( D ) TOPOLOGY: both ( x i ) SEQUENCE DESCRIPTION: SEQ ID NO:2:

Cys Ser Cys Ser Ser Trp Leu Asp Lys Glu Cys Val Tyr Phe Cys His
1               5                   10                  15
Leu Asp Ile Ile Trp
            20

( 2 ) INFORMATION FOR SEQ ID NO:3:

( i ) SEQUENCE CHARACTERISTICS:
        ( A ) LENGTH: 21 amino acids
        ( B ) TYPE: amino acid
        ( D ) TOPOLOGY: both ( x i ) SEQUENCE DESCRIPTION: SEQ ID NO:3:

Cys Thr Cys Phe Thr Tyr Lys Asp Lys Glu Cys Val Tyr Tyr Cys His
1               5                   10                  15
Leu Asp Ile Ile Trp
            20

( 2 ) INFORMATION FOR SEQ ID NO:4:

( i ) SEQUENCE CHARACTERISTICS:
    ( A ) LENGTH: 21 amino acids
    ( B ) TYPE: amino acid
    ( D ) TOPOLOGY: both ( x i ) SEQUENCE DESCRIPTION: SEQ ID NO:4:

```
Cys Ser Cys Lys Asp Met Thr Asp Lys Glu Cys Leu Tyr Phe Cys His
1               5                   10                  15
Gln Asp Val Ile Trp
            20
```

( 2 ) INFORMATION FOR SEQ ID NO:5:

( i ) SEQUENCE CHARACTERISTICS:
        ( A ) LENGTH: 21 amino acids
        ( B ) TYPE: amino acid
        ( D ) TOPOLOGY: both ( x i ) SEQUENCE DESCRIPTION: SEQ ID NO:5:

```
Cys Ser Cys Lys Asp Met Thr Asp Lys Glu Cys Leu Asn Phe Cys His
1               5                   10                  15
Gln Asp Val Ile Trp
            20
```

( 2 ) INFORMATION FOR SEQ ID NO:6:

( i ) SEQUENCE CHARACTERISTICS:
        ( A ) LENGTH: 21 amino acids
        ( B ) TYPE: amino acid
        ( D ) TOPOLOGY: both ( x i ) SEQUENCE DESCRIPTION: SEQ ID NO:6:

```
Cys Ser Cys Lys Asp Met Thr Asp Glu Glu Cys Leu Asn Phe Cys His
1               5                   10                  15
Gln Asp Val Ile Trp
            20
```

( 2 ) INFORMATION FOR SEQ ID NO:7:

( i ) SEQUENCE CHARACTERISTICS:
        ( A ) LENGTH: 21 amino acids
        ( B ) TYPE: amino acid
        ( D ) TOPOLOGY: both ( i x ) FEATURE:
        ( A ) NAME/KEY: Modified-site
        ( B ) LOCATION: 1
        ( D ) OTHER INFORMATION: /label=Dpr ( i x ) FEATURE:
        ( A ) NAME/KEY: Cross-links
        ( B ) LOCATION: 1..15

( x i ) SEQUENCE DESCRIPTION: SEQ ID NO:7:

```
Xaa Ser Cys Ser Ser Leu Met Asp Lys Glu Cys Val Tyr Phe Asp His
1               5                   10                  15
Leu Asp Ile Ile Trp
            20
```

( 2 ) INFORMATION FOR SEQ ID NO:8:

( i ) SEQUENCE CHARACTERISTICS:
        ( A ) LENGTH: 21 amino acids
        ( B ) TYPE: amino acid
        ( D ) TOPOLOGY: both ( i i ) MOLECULE TYPE: peptide ( i x ) FEATURE:
    ( A ) NAME/KEY: Modified-site
    ( B ) LOCATION: 1
    ( D ) OTHER INFORMATION: /label=Dpr ( i x ) FEATURE:
    ( A ) NAME/KEY: Cross-links
    ( B ) LOCATION: 1..15

( x i ) SEQUENCE DESCRIPTION: SEQ ID NO:8:

Xaa Ser Cys Ser Ser Leu Met Asp Lys Glu Cys Val Tyr Phe Glu His
1               5                   10                  15
Leu Asp Ile Ile Trp
            20

( 2 ) INFORMATION FOR SEQ ID NO:9:

( i ) SEQUENCE CHARACTERISTICS:
        ( A ) LENGTH: 21 amino acids
        ( B ) TYPE: amino acid
        ( D ) TOPOLOGY: both ( i i ) MOLECULE TYPE: peptide ( i x ) FEATURE:
        ( A ) NAME/KEY: Modified-site
        ( B ) LOCATION: 1
        ( D ) OTHER INFORMATION: /label=Dpr ( i x ) FEATURE:
        ( A ) NAME/KEY: Cross-links
        ( B ) LOCATION: 1..15

( x i ) SEQUENCE DESCRIPTION: SEQ ID NO:9:

Xaa Ser Cys Ser Ser Trp Leu Asp Lys Glu Cys Val Tyr Phe Asp His
1               5                   10                  15
Leu Asp Ile Ile Trp
            20

( 2 ) INFORMATION FOR SEQ ID NO:10:

( i ) SEQUENCE CHARACTERISTICS:
        ( A ) LENGTH: 21 amino acids
        ( B ) TYPE: amino acid
        ( D ) TOPOLOGY: both ( i i ) MOLECULE TYPE: peptide ( i x ) FEATURE:
        ( A ) NAME/KEY: Modified-site
        ( B ) LOCATION: 1
        ( D ) OTHER INFORMATION: /label=Dpr ( i x ) FEATURE:
        ( A ) NAME/KEY: Cross-links
        ( B ) LOCATION: 1..15

( x i ) SEQUENCE DESCRIPTION: SEQ ID NO:10:

Xaa Ser Cys Ser Ser Trp Leu Asp Lys Glu Cys Val Tyr Phe Glu His
1               5                   10                  15
Leu Asp Ile Ile Trp
            20

( 2 ) INFORMATION FOR SEQ ID NO:11:

( i ) SEQUENCE CHARACTERISTICS:
        ( A ) LENGTH: 21 amino acids
        ( B ) TYPE: amino acid
        ( D ) TOPOLOGY: both ( i i ) MOLECULE TYPE: peptide ( i x ) FEATURE:
            ( A ) NAME/KEY: Modified-site
            ( B ) LOCATION: 1
            ( D ) OTHER INFORMATION: /label=Dpr ( i x ) FEATURE:
            ( A ) NAME/KEY: Cross-links
            ( B ) LOCATION: 1..15

( x i ) SEQUENCE DESCRIPTION: SEQ ID NO:11:

Xaa Thr Cys Phe Thr Tyr Lys Asp Lys Glu Cys Val Tyr Tyr Asp His
1               5                   10                  15

Leu Asp Ile Ile Trp
            20

( 2 ) INFORMATION FOR SEQ ID NO:12:

( i ) SEQUENCE CHARACTERISTICS:
                    ( A ) LENGTH: 21 amino acids
                    ( B ) TYPE: amino acid
                    ( D ) TOPOLOGY: both ( i i ) MOLECULE TYPE: peptide ( i x ) FEATURE:
                    ( A ) NAME/KEY: Modified-site
                    ( B ) LOCATION: 1
                    ( D ) OTHER INFORMATION: /label=Dpr ( i x ) FEATURE:
                    ( A ) NAME/KEY: Cross-links
                    ( B ) LOCATION: 1..15

( x i ) SEQUENCE DESCRIPTION: SEQ ID NO:12:

Xaa Thr Cys Phe Thr Tyr Lys Asp Lys Glu Cys Val Tyr Tyr Glu His
1               5                   10                  15

Leu Asp Ile Ile Trp
            20

( 2 ) INFORMATION FOR SEQ ID NO:13:

( i ) SEQUENCE CHARACTERISTICS:
                    ( A ) LENGTH: 21 amino acids
                    ( B ) TYPE: amino acid
                    ( D ) TOPOLOGY: both ( i i ) MOLECULE TYPE: peptide ( i x ) FEATURE:
                    ( A ) NAME/KEY: Modified-site
                    ( B ) LOCATION: 1
                    ( D ) OTHER INFORMATION: /label=Dpr ( i x ) FEATURE:
                    ( A ) NAME/KEY: Cross-links
                    ( B ) LOCATION: 1..15

( x i ) SEQUENCE DESCRIPTION: SEQ ID NO:13:

Xaa Ser Cys Lys Asp Met Thr Asp Lys Glu Cys Leu Tyr Phe Asp His
1               5                   10                  15

Gln Asp Val Ile Trp
            20

( 2 ) INFORMATION FOR SEQ ID NO:14:

( i ) SEQUENCE CHARACTERISTICS:
                    ( A ) LENGTH: 21 amino acids
                    ( B ) TYPE: amino acid
                    ( D ) TOPOLOGY: both ( i i ) MOLECULE TYPE: peptide ( i x ) FEATURE:
  ( A ) NAME/KEY: Modified-site
  ( B ) LOCATION: 1
  ( D ) OTHER INFORMATION: /label=Dpr ( i x ) FEATURE:
  ( A ) NAME/KEY: Cross-links
  ( B ) LOCATION: 1..15

( x i ) SEQUENCE DESCRIPTION: SEQ ID NO:14:

Xaa Ser Cys Lys Asp Met Thr Asp Lys Glu Cys Leu Tyr Phe Glu His
1               5                   10                  15

Gln Asp Val Ile Trp
            20

( 2 ) INFORMATION FOR SEQ ID NO:15:

( i ) SEQUENCE CHARACTERISTICS:
  ( A ) LENGTH: 21 amino acids
  ( B ) TYPE: amino acid
  ( D ) TOPOLOGY: both ( i i ) MOLECULE TYPE: peptide ( i x ) FEATURE:
  ( A ) NAME/KEY: Modified-site
  ( B ) LOCATION: 1
  ( D ) OTHER INFORMATION: /label=Dpr ( i x ) FEATURE:
  ( A ) NAME/KEY: Cross-links
  ( B ) LOCATION: 1..15

( x i ) SEQUENCE DESCRIPTION: SEQ ID NO:15:

Xaa Ser Cys Lys Asp Met Thr Asp Lys Glu Cys Leu Asn Phe Asp His
1               5                   10                  15

Gln Asp Val Ile Trp
            20

( 2 ) INFORMATION FOR SEQ ID NO:16:

( i ) SEQUENCE CHARACTERISTICS:
  ( A ) LENGTH: 21 amino acids
  ( B ) TYPE: amino acid
  ( D ) TOPOLOGY: both ( i i ) MOLECULE TYPE: peptide ( i x ) FEATURE:
  ( A ) NAME/KEY: Modified-site
  ( B ) LOCATION: 1
  ( D ) OTHER INFORMATION: /label=Dpr ( i x ) FEATURE:
  ( A ) NAME/KEY: Cross-links
  ( B ) LOCATION: 1..15

( x i ) SEQUENCE DESCRIPTION: SEQ ID NO:16:

Xaa Ser Cys Lys Asp Met Thr Asp Lys Glu Cys Leu Asn Phe Glu His
1               5                   10                  15

Gln Asp Val Ile Trp
            20

( 2 ) INFORMATION FOR SEQ ID NO:17:

( i ) SEQUENCE CHARACTERISTICS:
  ( A ) LENGTH: 21 amino acids
  ( B ) TYPE: amino acid
  ( D ) TOPOLOGY: both ( i i ) MOLECULE TYPE: peptide ( i x ) FEATURE:
    ( A ) NAME/KEY: Modified-site
    ( B ) LOCATION: 1
    ( D ) OTHER INFORMATION: /label=Dpr ( i x ) FEATURE:
    ( A ) NAME/KEY: Cross-links
    ( B ) LOCATION: 1..15

( x i ) SEQUENCE DESCRIPTION: SEQ ID NO:17:

```
Xaa  Ser  Cys  Lys  Asp  Met  Thr  Asp  Glu  Glu  Cys  Leu  Asn  Phe  Asp  His
1                   5                        10                        15
Gln  Asp  Val  Ile  Trp
                    20
```

( 2 ) INFORMATION FOR SEQ ID NO:18:

( i ) SEQUENCE CHARACTERISTICS:
        ( A ) LENGTH: 21 amino acids
        ( B ) TYPE: amino acid
        ( D ) TOPOLOGY: both ( i i ) MOLECULE TYPE: peptide ( i x ) FEATURE:
        ( A ) NAME/KEY: Modified-site
        ( B ) LOCATION: 1
        ( D ) OTHER INFORMATION: /label=Dpr ( i x ) FEATURE:
        ( A ) NAME/KEY: Cross-links
        ( B ) LOCATION: 1..15

( x i ) SEQUENCE DESCRIPTION: SEQ ID NO:18:

```
Xaa  Ser  Cys  Lys  Asp  Met  Thr  Asp  Glu  Glu  Cys  Leu  Asn  Phe  Glu  His
1                   5                        10                        15
Gln  Asp  Val  Ile  Trp
                    20
```

( 2 ) INFORMATION FOR SEQ ID NO:19:

( i ) SEQUENCE CHARACTERISTICS:
        ( A ) LENGTH: 21 amino acids
        ( B ) TYPE: amino acid
        ( D ) TOPOLOGY: both ( i i ) MOLECULE TYPE: peptide ( i x ) FEATURE:
        ( A ) NAME/KEY: Modified-site
        ( B ) LOCATION: 1
        ( D ) OTHER INFORMATION: /label=Dpr ( i x ) FEATURE:
        ( A ) NAME/KEY: Cross-links
        ( B ) LOCATION: 1..15

( x i ) SEQUENCE DESCRIPTION: SEQ ID NO:19:

```
Xaa  Ser  Cys  Ala  Ser  Leu  Met  Asp  Lys  Glu  Cys  Val  Tyr  Phe  Asp  His
1                   5                        10                        15
Leu  Asp  Ile  Ile  Trp
                    20
```

( 2 ) INFORMATION FOR SEQ ID NO:20:

( i ) SEQUENCE CHARACTERISTICS:
        ( A ) LENGTH: 21 amino acids
        ( B ) TYPE: amino acid ( D ) TOPOLOGY: both ( i i ) MOLECULE TYPE: peptide ( i x ) FEATURE:
            ( A ) NAME/KEY: Modified-site
            ( B ) LOCATION: 1
            ( D ) OTHER INFORMATION: /label=Dpr ( i x ) FEATURE:
            ( A ) NAME/KEY: Cross-links
            ( B ) LOCATION: 1..15

( x i ) SEQUENCE DESCRIPTION: SEQ ID NO:20:

Xaa  Ser  Cys  Ala  Ser  Leu  Met  Asp  Lys  Glu  Cys  Val  Tyr  Phe  Glu  His
1                   5                        10                            15

Leu  Asp  Ile  Ile  Trp
                20

( 2 ) INFORMATION FOR SEQ ID NO:21:

( i ) SEQUENCE CHARACTERISTICS:
            ( A ) LENGTH: 21 amino acids
            ( B ) TYPE: amino acid
            ( D ) TOPOLOGY: both ( i i ) MOLECULE TYPE: peptide ( i x ) FEATURE:
            ( A ) NAME/KEY: Modified-site
            ( B ) LOCATION: 1
            ( D ) OTHER INFORMATION: /label=Dpr ( i x ) FEATURE:
            ( A ) NAME/KEY: Cross-links
            ( B ) LOCATION: 1..15

( x i ) SEQUENCE DESCRIPTION: SEQ ID NO:21:

Xaa  Ser  Cys  Ser  Ala  Leu  Met  Asp  Lys  Glu  Cys  Val  Tyr  Phe  Asp  His
1                   5                        10                            15

Leu  Asp  Ile  Ile  Trp
                20

( 2 ) INFORMATION FOR SEQ ID NO:22:

( i ) SEQUENCE CHARACTERISTICS:
            ( A ) LENGTH: 21 amino acids
            ( B ) TYPE: amino acid
            ( D ) TOPOLOGY: both ( i i ) MOLECULE TYPE: peptide ( i x ) FEATURE:
            ( A ) NAME/KEY: Modified-site
            ( B ) LOCATION: 1
            ( D ) OTHER INFORMATION: /label=Dpr ( i x ) FEATURE:
            ( A ) NAME/KEY: Cross-links
            ( B ) LOCATION: 1..15

( x i ) SEQUENCE DESCRIPTION: SEQ ID NO:22:

Xaa  Ser  Cys  Ser  Ala  Leu  Met  Asp  Lys  Glu  Cys  Val  Tyr  Phe  Glu  His
1                   5                        10                            15

Leu  Asp  Ile  Ile  Trp
                20

( 2 ) INFORMATION FOR SEQ ID NO:23:

( i ) SEQUENCE CHARACTERISTICS:
            ( A ) LENGTH: 21 amino acids ( B ) TYPE: amino acid
    ( D ) TOPOLOGY: both ( i i ) MOLECULE TYPE: peptide ( i x ) FEATURE:
    ( A ) NAME/KEY: Modified-site
    ( B ) LOCATION: 1
    ( D ) OTHER INFORMATION: /label=Dpr ( i x ) FEATURE:
    ( A ) NAME/KEY: Cross-links
    ( B ) LOCATION: 1..15

( x i ) SEQUENCE DESCRIPTION: SEQ ID NO:23:

Xaa Ser Cys Ser Ser Gly Met Asp Lys Glu Cys Val Tyr Phe Asp His
1               5                   10                  15

Leu Asp Ile Ile Trp
            20

( 2 ) INFORMATION FOR SEQ ID NO:24:

( i ) SEQUENCE CHARACTERISTICS:
        ( A ) LENGTH: 21 amino acids
        ( B ) TYPE: amino acid
        ( D ) TOPOLOGY: both ( i i ) MOLECULE TYPE: peptide ( i x ) FEATURE:
        ( A ) NAME/KEY: Modified-site
        ( B ) LOCATION: 1
        ( D ) OTHER INFORMATION: /label=Dpr ( i x ) FEATURE:
        ( A ) NAME/KEY: Cross-links
        ( B ) LOCATION: 1..15

( x i ) SEQUENCE DESCRIPTION: SEQ ID NO:24:

Xaa Ser Cys Ser Ser Gly Met Asp Lys Glu Cys Val Tyr Phe Glu His
1               5                   10                  15

Leu Asp Ile Ile Trp
            20

( 2 ) INFORMATION FOR SEQ ID NO:25:

( i ) SEQUENCE CHARACTERISTICS:
        ( A ) LENGTH: 21 amino acids
        ( B ) TYPE: amino acid
        ( D ) TOPOLOGY: both ( i i ) MOLECULE TYPE: peptide ( i x ) FEATURE:
        ( A ) NAME/KEY: Modified-site
        ( B ) LOCATION: 1
        ( D ) OTHER INFORMATION: /label=Dpr ( i x ) FEATURE:
        ( A ) NAME/KEY: Cross-links
        ( B ) LOCATION: 1..15

( x i ) SEQUENCE DESCRIPTION: SEQ ID NO:25:

Xaa Ser Cys Ser Ser Leu Met Asn Lys Glu Cys Val Tyr Phe Asp His
1               5                   10                  15

Leu Asp Ile Ile Trp
            20

( 2 ) INFORMATION FOR SEQ ID NO:26:

( i ) SEQUENCE CHARACTERISTICS:

(A) LENGTH: 21 amino acids
(B) TYPE: amino acid
(D) TOPOLOGY: both (ii) MOLECULE TYPE: peptide (ix) FEATURE:
(A) NAME/KEY: Modified-site
(B) LOCATION: 1
(D) OTHER INFORMATION: /label=Dpr (ix) FEATURE:
(A) NAME/KEY: Cross-links
(B) LOCATION: 1..15

(xi) SEQUENCE DESCRIPTION: SEQ ID NO:26:

Xaa Ser Cys Ser Ser Leu Met Asn Lys Glu Cys Val Tyr Phe Glu His
1               5                   10                  15

Leu Asp Ile Ile Trp
            20

(2) INFORMATION FOR SEQ ID NO:27:

(i) SEQUENCE CHARACTERISTICS:
(A) LENGTH: 21 amino acids
(B) TYPE: amino acid
(D) TOPOLOGY: both (ii) MOLECULE TYPE: peptide (ix) FEATURE:
(A) NAME/KEY: Modified-site
(B) LOCATION: 1
(D) OTHER INFORMATION: /label=Dpr (ix) FEATURE:
(A) NAME/KEY: Cross-links
(B) LOCATION: 1..15

(xi) SEQUENCE DESCRIPTION: SEQ ID NO:27:

Xaa Ser Cys Ser Ser Leu Met Asp Leu Glu Cys Val Tyr Phe Asp His
1               5                   10                  15

Leu Asp Ile Ile Trp
            20

(2) INFORMATION FOR SEQ ID NO:28:

(i) SEQUENCE CHARACTERISTICS:
(A) LENGTH: 21 amino acids
(B) TYPE: amino acid
(D) TOPOLOGY: both (ii) MOLECULE TYPE: peptide (ix) FEATURE:
(A) NAME/KEY: Modified-site
(B) LOCATION: 1
(D) OTHER INFORMATION: /label=Dpr (ix) FEATURE:
(A) NAME/KEY: Cross-links
(B) LOCATION: 1..15

(xi) SEQUENCE DESCRIPTION: SEQ ID NO:28:

Xaa Ser Cys Ser Ser Leu Met Asp Leu Glu Cys Val Tyr Phe Glu His
1               5                   10                  15

Leu Asp Ile Ile Trp
            20

(2) INFORMATION FOR SEQ ID NO:29:

( i ) SEQUENCE CHARACTERISTICS:
   ( A ) LENGTH: 21 amino acids
   ( B ) TYPE: amino acid
   ( D ) TOPOLOGY: both ( i i ) MOLECULE TYPE: peptide ( i x ) FEATURE:
   ( A ) NAME/KEY: Modified-site
   ( B ) LOCATION: 1
   ( D ) OTHER INFORMATION: /label=Dpr ( i x ) FEATURE:
   ( A ) NAME/KEY: Cross-links
   ( B ) LOCATION: 1..15

( x i ) SEQUENCE DESCRIPTION: SEQ ID NO:29:

Xaa Ser Cys Ser Ser Leu Met Asp Lys Glu Cys Val Phe Phe Asp His
1               5                   10                  15

Leu Asp Ile Ile Trp
            20

( 2 ) INFORMATION FOR SEQ ID NO:30:

( i ) SEQUENCE CHARACTERISTICS:
   ( A ) LENGTH: 21 amino acids
   ( B ) TYPE: amino acid
   ( D ) TOPOLOGY: both ( i i ) MOLECULE TYPE: peptide ( i x ) FEATURE:
   ( A ) NAME/KEY: Modified-site
   ( B ) LOCATION: 1
   ( D ) OTHER INFORMATION: /label=Dpr ( i x ) FEATURE:
   ( A ) NAME/KEY: Cross-links
   ( B ) LOCATION: 1..15

( x i ) SEQUENCE DESCRIPTION: SEQ ID NO:30:

Xaa Ser Cys Ser Ser Leu Met Asp Lys Glu Cys Val Phe Phe Glu His
1               5                   10                  15

Leu Asp Ile Ile Trp
            20

( 2 ) INFORMATION FOR SEQ ID NO:31:

( i ) SEQUENCE CHARACTERISTICS:
   ( A ) LENGTH: 21 amino acids
   ( B ) TYPE: amino acid
   ( D ) TOPOLOGY: both ( i i ) MOLECULE TYPE: peptide ( i x ) FEATURE:
   ( A ) NAME/KEY: Modified-site
   ( B ) LOCATION: 1
   ( D ) OTHER INFORMATION: /label=Dpr ( i x ) FEATURE:
   ( A ) NAME/KEY: Cross-links
   ( B ) LOCATION: 1..15

( x i ) SEQUENCE DESCRIPTION: SEQ ID NO:31:

Xaa Ser Cys Ser Ser Leu Met Asp Lys Glu Cys Val Tyr Phe Asp His
1               5                   10                  15

Leu Asp Ile Ile Tyr
            20

( 2 ) INFORMATION FOR SEQ ID NO:32:

( i ) SEQUENCE CHARACTERISTICS:
   ( A ) LENGTH: 21 amino acids
   ( B ) TYPE: amino acid
   ( D ) TOPOLOGY: both ( i i ) MOLECULE TYPE: peptide ( i x ) FEATURE:
   ( A ) NAME/KEY: Modified-site
   ( B ) LOCATION: 1
   ( D ) OTHER INFORMATION: /label=Dpr ( i x ) FEATURE:
   ( A ) NAME/KEY: Cross-links
   ( B ) LOCATION: 1..15

( x i ) SEQUENCE DESCRIPTION: SEQ ID NO:32:

Xaa  Ser  Cys  Ser  Ser  Leu  Met  Asp  Lys  Glu  Cys  Val  Tyr  Phe  Glu  His
1                   5                        10                            15

Leu  Asp  Ile  Ile  Tyr
               20

( 2 ) INFORMATION FOR SEQ ID NO:33:

( i ) SEQUENCE CHARACTERISTICS:
   ( A ) LENGTH: 21 amino acids
   ( B ) TYPE: amino acid
   ( D ) TOPOLOGY: both ( i i ) MOLECULE TYPE: peptide ( i x ) FEATURE:
   ( A ) NAME/KEY: Modified-site
   ( B ) LOCATION: 1
   ( D ) OTHER INFORMATION: /label=Dpr ( i x ) FEATURE:
   ( A ) NAME/KEY: Cross-links
   ( B ) LOCATION: 1..15

( x i ) SEQUENCE DESCRIPTION: SEQ ID NO:33:

Xaa  Ser  Cys  Ser  Ser  Leu  Met  Asp  Lys  Glu  Cys  Val  Tyr  Phe  Asp  His
1                   5                        10                            15

Leu  Asp  Ile  Ile  Phe
               20

( 2 ) INFORMATION FOR SEQ ID NO:34:

( i ) SEQUENCE CHARACTERISTICS:
   ( A ) LENGTH: 21 amino acids
   ( B ) TYPE: amino acid
   ( D ) TOPOLOGY: both ( i i ) MOLECULE TYPE: peptide ( i x ) FEATURE:
   ( A ) NAME/KEY: Modified-site
   ( B ) LOCATION: 1
   ( D ) OTHER INFORMATION: /label=Dpr ( i x ) FEATURE:
   ( A ) NAME/KEY: Cross-links
   ( B ) LOCATION: 1..15

( x i ) SEQUENCE DESCRIPTION: SEQ ID NO:34:

Xaa  Ser  Cys  Ser  Ser  Leu  Met  Asp  Lys  Glu  Cys  Val  Tyr  Phe  Glu  His
1                   5                        10                            15

Leu  Asp  Ile  Ile  Phe
               20

( 2 ) INFORMATION FOR SEQ ID NO:35:

( i ) SEQUENCE CHARACTERISTICS:
    ( A ) LENGTH: 21 amino acids
    ( B ) TYPE: amino acid
    ( D ) TOPOLOGY: both ( i i ) MOLECULE TYPE: peptide ( i x ) FEATURE:
    ( A ) NAME/KEY: Modified-site
    ( B ) LOCATION: 1
    ( D ) OTHER INFORMATION: /label=Dpr ( i x ) FEATURE:
    ( A ) NAME/KEY: Cross-links
    ( B ) LOCATION: 1..15

( x i ) SEQUENCE DESCRIPTION: SEQ ID NO:35:

Xaa Ser Ser Ser Ser Leu Met Asp Lys Glu Ser Val Tyr Phe Asp His
1               5                   10                  15
Leu Asp Ile Ile Trp
              20

( 2 ) INFORMATION FOR SEQ ID NO:36:

( i ) SEQUENCE CHARACTERISTICS:
    ( A ) LENGTH: 21 amino acids
    ( B ) TYPE: amino acid
    ( D ) TOPOLOGY: both ( i i ) MOLECULE TYPE: peptide ( i x ) FEATURE:
    ( A ) NAME/KEY: Modified-site
    ( B ) LOCATION: 1
    ( D ) OTHER INFORMATION: /label=Dpr ( i x ) FEATURE:
    ( A ) NAME/KEY: Cross-links
    ( B ) LOCATION: 1..15

( x i ) SEQUENCE DESCRIPTION: SEQ ID NO:36:

Xaa Ser Ser Ser Ser Leu Met Asp Lys Glu Ser Val Tyr Phe Glu His
1               5                   10                  15
Leu Asp Ile Ile Trp
              20

( 2 ) INFORMATION FOR SEQ ID NO:37:

( i ) SEQUENCE CHARACTERISTICS:
    ( A ) LENGTH: 21 amino acids
    ( B ) TYPE: amino acid
    ( D ) TOPOLOGY: both ( i i ) MOLECULE TYPE: peptide ( i x ) FEATURE:
    ( A ) NAME/KEY: Modified-site
    ( B ) LOCATION: 1
    ( D ) OTHER INFORMATION: /label=Dpr ( i x ) FEATURE:
    ( A ) NAME/KEY: Cross-links
    ( B ) LOCATION: 1..15

( x i ) SEQUENCE DESCRIPTION: SEQ ID NO:37:

Xaa Ser Ser Ser Ser Trp Leu Asp Lys Glu Ser Val Tyr Phe Asp His
1               5                   10                  15
Leu Asp Ile Ile Trp
              20

( 2 ) INFORMATION FOR SEQ ID NO:38:

( i ) SEQUENCE CHARACTERISTICS:
        ( A ) LENGTH: 21 amino acids
        ( B ) TYPE: amino acid
        ( D ) TOPOLOGY: both ( i i ) MOLECULE TYPE: peptide ( i x ) FEATURE:
        ( A ) NAME/KEY: Modified-site
        ( B ) LOCATION: 1
        ( D ) OTHER INFORMATION: /label=Dpr ( i x ) FEATURE:
        ( A ) NAME/KEY: Cross-links
        ( B ) LOCATION: 1..15

( x i ) SEQUENCE DESCRIPTION: SEQ ID NO:38:

Xaa Ser Ser Ser Ser Trp Leu Asp Lys Glu Ser Val Tyr Phe Glu His
1               5                   10                  15
Leu Asp Ile Ile Trp
            20

( 2 ) INFORMATION FOR SEQ ID NO:39:

( i ) SEQUENCE CHARACTERISTICS:
        ( A ) LENGTH: 21 amino acids
        ( B ) TYPE: amino acid
        ( D ) TOPOLOGY: both ( i i ) MOLECULE TYPE: peptide ( i x ) FEATURE:
        ( A ) NAME/KEY: Modified-site
        ( B ) LOCATION: 1
        ( D ) OTHER INFORMATION: /label=Dpr ( i x ) FEATURE:
        ( A ) NAME/KEY: Cross-links
        ( B ) LOCATION: 1..15

( x i ) SEQUENCE DESCRIPTION: SEQ ID NO:39:

Xaa Thr Ser Phe Thr Tyr Lys Asp Lys Glu Ser Val Tyr Tyr Asp His
1               5                   10                  15
Leu Asp Ile Ile Trp
            20

( 2 ) INFORMATION FOR SEQ ID NO:40:

( i ) SEQUENCE CHARACTERISTICS:
        ( A ) LENGTH: 21 amino acids
        ( B ) TYPE: amino acid
        ( D ) TOPOLOGY: both ( i i ) MOLECULE TYPE: peptide ( i x ) FEATURE:
        ( A ) NAME/KEY: Modified-site
        ( B ) LOCATION: 1
        ( D ) OTHER INFORMATION: /label=Dpr ( i x ) FEATURE:
        ( A ) NAME/KEY: Cross-links
        ( B ) LOCATION: 1..15

( x i ) SEQUENCE DESCRIPTION: SEQ ID NO:40:

Xaa Thr Ser Phe Thr Tyr Lys Asp Lys Glu Ser Val Tyr Tyr Glu His
1               5                   10                  15
Leu Asp Ile Ile Trp
            20

( 2 ) INFORMATION FOR SEQ ID NO:41:

( i ) SEQUENCE CHARACTERISTICS:
        ( A ) LENGTH: 21 amino acids
        ( B ) TYPE: amino acid
        ( D ) TOPOLOGY: both ( i i ) MOLECULE TYPE: peptide ( i x ) FEATURE:
        ( A ) NAME/KEY: Modified-site
        ( B ) LOCATION: 1
        ( D ) OTHER INFORMATION: /label=Dpr ( i x ) FEATURE:
        ( A ) NAME/KEY: Cross-links
        ( B ) LOCATION: 1..15

( x i ) SEQUENCE DESCRIPTION: SEQ ID NO:41:

Xaa Ser Ser Lys Asp Met Thr Asp Lys Glu Ser Leu Asn Phe Asp His
1               5                   10                  15

Gln Asp Val Ile Trp
            20

( 2 ) INFORMATION FOR SEQ ID NO:42:

( i ) SEQUENCE CHARACTERISTICS:
        ( A ) LENGTH: 21 amino acids
        ( B ) TYPE: amino acid
        ( D ) TOPOLOGY: both ( i i ) MOLECULE TYPE: peptide ( i x ) FEATURE:
        ( A ) NAME/KEY: Modified-site
        ( B ) LOCATION: 1
        ( D ) OTHER INFORMATION: /label=Dpr ( i x ) FEATURE:
        ( A ) NAME/KEY: Cross-links
        ( B ) LOCATION: 1..15

( x i ) SEQUENCE DESCRIPTION: SEQ ID NO:42:

Xaa Ser Ser Lys Asp Met Thr Asp Lys Glu Ser Leu Asn Phe Glu His
1               5                   10                  15

Gln Asp Val Ile Trp
            20

( 2 ) INFORMATION FOR SEQ ID NO:43:

( i ) SEQUENCE CHARACTERISTICS:
        ( A ) LENGTH: 21 amino acids
        ( B ) TYPE: amino acid
        ( D ) TOPOLOGY: both ( i i ) MOLECULE TYPE: peptide ( i x ) FEATURE:
        ( A ) NAME/KEY: Modified-site
        ( B ) LOCATION: 1
        ( D ) OTHER INFORMATION: /label=Dpr ( i x ) FEATURE:
        ( A ) NAME/KEY: Cross-links
        ( B ) LOCATION: 1..15

( x i ) SEQUENCE DESCRIPTION: SEQ ID NO:43:

Xaa Ser Ser Lys Asp Met Thr Asp Lys Glu Ser Leu Tyr Phe Asp His
1               5                   10                  15

Gln Asp Val Ile Trp

20

( 2 ) INFORMATION FOR SEQ ID NO:44:

( i ) SEQUENCE CHARACTERISTICS:
        ( A ) LENGTH: 21 amino acids
        ( B ) TYPE: amino acid
        ( D ) TOPOLOGY: both ( i i ) MOLECULE TYPE: peptide ( i x ) FEATURE:
        ( A ) NAME/KEY: Modified-site
        ( B ) LOCATION: 1
        ( D ) OTHER INFORMATION: /label=Dpr ( i x ) FEATURE:
        ( A ) NAME/KEY: Cross-links
        ( B ) LOCATION: 1..15

( x i ) SEQUENCE DESCRIPTION: SEQ ID NO:44:

```
Xaa  Ser  Ser  Lys  Asp  Met  Thr  Asp  Lys  Glu  Ser  Leu  Tyr  Phe  Glu  His
 1              5                        10                            15
Gln  Asp  Val  Ile  Trp
              20
```

( 2 ) INFORMATION FOR SEQ ID NO:45:

( i ) SEQUENCE CHARACTERISTICS:
        ( A ) LENGTH: 21 amino acids
        ( B ) TYPE: amino acid
        ( D ) TOPOLOGY: both ( i i ) MOLECULE TYPE: peptide ( i x ) FEATURE:
        ( A ) NAME/KEY: Modified-site
        ( B ) LOCATION: 1
        ( D ) OTHER INFORMATION: /label=Dpr ( i x ) FEATURE:
        ( A ) NAME/KEY: Cross-links
        ( B ) LOCATION: 1..15

( x i ) SEQUENCE DESCRIPTION: SEQ ID NO:45:

```
Xaa  Ser  Ser  Lys  Asp  Met  Thr  Asp  Glu  Glu  Ser  Leu  Asn  Phe  Asp  His
 1              5                        10                            15
Gln  Asp  Val  Ile  Trp
              20
```

( 2 ) INFORMATION FOR SEQ ID NO:46:

( i ) SEQUENCE CHARACTERISTICS:
        ( A ) LENGTH: 21 amino acids
        ( B ) TYPE: amino acid
        ( D ) TOPOLOGY: both ( i i ) MOLECULE TYPE: peptide ( i x ) FEATURE:
        ( A ) NAME/KEY: Modified-site
        ( B ) LOCATION: 1
        ( D ) OTHER INFORMATION: /label=Dpr ( i x ) FEATURE:
        ( A ) NAME/KEY: Cross-links
        ( B ) LOCATION: 1..15

( x i ) SEQUENCE DESCRIPTION: SEQ ID NO:46:

```
Xaa  Ser  Ser  Lys  Asp  Met  Thr  Asp  Glu  Glu  Ser  Leu  Asn  Phe  Glu  His
 1              5                        10                            15
```

Gln Asp Val Ile Trp
            20

( 2 ) INFORMATION FOR SEQ ID NO:47:

( i ) SEQUENCE CHARACTERISTICS:
        ( A ) LENGTH: 38 amino acids
        ( B ) TYPE: amino acid
        ( D ) TOPOLOGY: both ( i i ) MOLECULE TYPE: peptide ( i x ) FEATURE:
        ( A ) NAME/KEY: Modified-site
        ( B ) LOCATION: 1
        ( D ) OTHER INFORMATION: /label=Dpr ( i x ) FEATURE:
        ( A ) NAME/KEY: Cross-links
        ( B ) LOCATION: 1..15

( x i ) SEQUENCE DESCRIPTION: SEQ ID NO:47:

Xaa Ser Cys Ser Ser Leu Met Asp Lys Glu Cys Val Tyr Phe Asp His
 1               5                   10                  15

Leu Asp Ile Ile Trp Val Asn Thr Pro Glu His Val Val Pro Tyr Gly
            20                  25                  30

Leu Gly Ser Pro Arg Ser
            35

( 2 ) INFORMATION FOR SEQ ID NO:48:

( i ) SEQUENCE CHARACTERISTICS:
        ( A ) LENGTH: 38 amino acids
        ( B ) TYPE: amino acid
        ( D ) TOPOLOGY: both ( i i ) MOLECULE TYPE: peptide ( i x ) FEATURE:
        ( A ) NAME/KEY: Modified-site
        ( B ) LOCATION: 1
        ( D ) OTHER INFORMATION: /label=Dpr ( i x ) FEATURE:
        ( A ) NAME/KEY: Cross-links
        ( B ) LOCATION: 1..15

( x i ) SEQUENCE DESCRIPTION: SEQ ID NO:48:

Xaa Ser Cys Ser Ser Leu Met Asp Lys Glu Cys Val Tyr Phe Glu His
 1               5                   10                  15

Leu Asp Ile Ile Trp Val Asn Thr Pro Glu His Val Val Pro Tyr Gly
            20                  25                  30

Leu Gly Ser Pro Arg Ser
            35

( 2 ) INFORMATION FOR SEQ ID NO:49:

( i ) SEQUENCE CHARACTERISTICS:
        ( A ) LENGTH: 39 amino acids
        ( B ) TYPE: amino acid
        ( D ) TOPOLOGY: both ( i i ) MOLECULE TYPE: peptide ( i x ) FEATURE:
        ( A ) NAME/KEY: Modified-site
        ( B ) LOCATION: 1
        ( D ) OTHER INFORMATION: /label=Dpr ( i x ) FEATURE:
        ( A ) NAME/KEY: Cross-links (B) LOCATION: 1..15

(xi) SEQUENCE DESCRIPTION: SEQ ID NO:49:

Xaa Ser Cys Ser Ser Leu Met Asp Lys Glu Cys Val Tyr Phe Asp His
1               5                   10                  15
Leu Asp Ile Ile Trp Val Asn Thr Pro Glu His Ile Val Pro Tyr Gly
            20                  25                  30
Leu Gly Ser Pro Ser Arg Ser
            35

(2) INFORMATION FOR SEQ ID NO:50:

(i) SEQUENCE CHARACTERISTICS:
    (A) LENGTH: 39 amino acids
    (B) TYPE: amino acid
    (D) TOPOLOGY: both (ii) MOLECULE TYPE: peptide (ix) FEATURE:
    (A) NAME/KEY: Modified-site
    (B) LOCATION: 1
    (D) OTHER INFORMATION: /label=Dpr (ix) FEATURE:
    (A) NAME/KEY: Cross-links
    (B) LOCATION: 1..15

(xi) SEQUENCE DESCRIPTION: SEQ ID NO:50:

Xaa Ser Cys Ser Ser Leu Met Asp Lys Glu Cys Val Tyr Phe Glu His
1               5                   10                  15
Leu Asp Ile Ile Trp Val Asn Thr Pro Glu His Ile Val Pro Tyr Gly
            20                  25                  30
Leu Gly Ser Pro Ser Arg Ser
            35

(2) INFORMATION FOR SEQ ID NO:51:

(i) SEQUENCE CHARACTERISTICS:
    (A) LENGTH: 38 amino acids
    (B) TYPE: amino acid
    (D) TOPOLOGY: both (ii) MOLECULE TYPE: peptide (ix) FEATURE:
    (A) NAME/KEY: Modified-site
    (B) LOCATION: 1
    (D) OTHER INFORMATION: /label=Dpr (ix) FEATURE:
    (A) NAME/KEY: Cross-links
    (B) LOCATION: 1..15

(xi) SEQUENCE DESCRIPTION: SEQ ID NO:51:

Xaa Ser Cys Ser Ser Trp Leu Asp Lys Glu Cys Val Tyr Phe Asp His
1               5                   10                  15
Leu Asp Ile Ile Trp Val Asn Thr Pro Glu His Val Val Pro Tyr Gly
            20                  25                  30
Leu Gly Ser Pro Arg Ser
            35

(2) INFORMATION FOR SEQ ID NO:52:

(i) SEQUENCE CHARACTERISTICS:
    (A) LENGTH: 38 amino acids
    (B) TYPE: amino acid
    (D) TOPOLOGY: both ( i i ) MOLECULE TYPE: peptide ( i x ) FEATURE:
  ( A ) NAME/KEY: Modified-site
  ( B ) LOCATION: 1
  ( D ) OTHER INFORMATION: /label=Dpr ( i x ) FEATURE:
  ( A ) NAME/KEY: Cross-links
  ( B ) LOCATION: 1..15

( x i ) SEQUENCE DESCRIPTION: SEQ ID NO:52:

```
Xaa  Ser  Cys  Ser  Ser  Trp  Leu  Asp  Lys  Glu  Cys  Val  Tyr  Phe  Glu  His
 1                    5                        10                         15

Leu  Asp  Ile  Ile  Trp  Val  Asn  Thr  Pro  Glu  His  Val  Val  Pro  Tyr  Gly
               20                        25                    30

Leu  Gly  Ser  Pro  Arg  Ser
               35
```

( 2 ) INFORMATION FOR SEQ ID NO:53:

( i ) SEQUENCE CHARACTERISTICS:
    ( A ) LENGTH: 39 amino acids
    ( B ) TYPE: amino acid
    ( D ) TOPOLOGY: both ( i i ) MOLECULE TYPE: peptide ( i x ) FEATURE:
  ( A ) NAME/KEY: Modified-site
  ( B ) LOCATION: 1
  ( D ) OTHER INFORMATION: /label=Dpr ( i x ) FEATURE:
  ( A ) NAME/KEY: Cross-links
  ( B ) LOCATION: 1..15

( x i ) SEQUENCE DESCRIPTION: SEQ ID NO:53:

```
Xaa  Ser  Cys  Ser  Ser  Trp  Leu  Asp  Lys  Glu  Cys  Val  Tyr  Phe  Asp  His
 1                    5                        10                         15

Leu  Asp  Ile  Ile  Trp  Val  Asn  Thr  Pro  Glu  His  Ile  Val  Pro  Tyr  Gly
               20                        25                    30

Leu  Gly  Ser  Pro  Ser  Arg  Ser
               35
```

( 2 ) INFORMATION FOR SEQ ID NO:54:

( i ) SEQUENCE CHARACTERISTICS:
    ( A ) LENGTH: 39 amino acids
    ( B ) TYPE: amino acid
    ( D ) TOPOLOGY: both ( i i ) MOLECULE TYPE: peptide ( i x ) FEATURE:
  ( A ) NAME/KEY: Modified-site
  ( B ) LOCATION: 1
  ( D ) OTHER INFORMATION: /label=Dpr ( i x ) FEATURE:
  ( A ) NAME/KEY: Cross-links
  ( B ) LOCATION: 1..15

( x i ) SEQUENCE DESCRIPTION: SEQ ID NO:54:

```
Xaa  Ser  Cys  Ser  Ser  Trp  Leu  Asp  Lys  Glu  Cys  Val  Tyr  Phe  Glu  His
 1                    5                        10                         15

Leu  Asp  Ile  Ile  Trp  Val  Asn  Thr  Pro  Glu  His  Ile  Val  Pro  Tyr  Gly
               20                        25                    30
```

```
Leu Gly Ser Pro Ser Arg Ser
         35
```

( 2 ) INFORMATION FOR SEQ ID NO:55:

( i ) SEQUENCE CHARACTERISTICS:
      ( A ) LENGTH: 38 amino acids
      ( B ) TYPE: amino acid
      ( D ) TOPOLOGY: both ( i i ) MOLECULE TYPE: peptide ( i x ) FEATURE:
      ( A ) NAME/KEY: Modified-site
      ( B ) LOCATION: 1
      ( D ) OTHER INFORMATION: /label=Dpr ( i x ) FEATURE:
      ( A ) NAME/KEY: Cross-links
      ( B ) LOCATION: 1..15

( x i ) SEQUENCE DESCRIPTION: SEQ ID NO:55:

```
Xaa Thr Cys Phe Thr Tyr Lys Asp Lys Glu Cys Val Tyr Tyr Asp His
 1           5                   10                  15
Leu Asp Ile Ile Trp Val Asn Thr Pro Glu His Val Val Pro Tyr Gly
            20                  25                  30
Leu Gly Ser Pro Arg Ser
         35
```

( 2 ) INFORMATION FOR SEQ ID NO:56:

( i ) SEQUENCE CHARACTERISTICS:
      ( A ) LENGTH: 38 amino acids
      ( B ) TYPE: amino acid
      ( D ) TOPOLOGY: both ( i i ) MOLECULE TYPE: peptide ( i x ) FEATURE:
      ( A ) NAME/KEY: Modified-site
      ( B ) LOCATION: 1
      ( D ) OTHER INFORMATION: /label=Dpr ( i x ) FEATURE:
      ( A ) NAME/KEY: Cross-links
      ( B ) LOCATION: 1..15

( x i ) SEQUENCE DESCRIPTION: SEQ ID NO:56:

```
Xaa Thr Cys Phe Thr Tyr Lys Asp Lys Glu Cys Val Tyr Tyr Glu His
 1           5                   10                  15
Leu Asp Ile Ile Trp Val Asn Thr Pro Glu His Val Val Pro Tyr Gly
            20                  25                  30
Leu Gly Ser Pro Arg Ser
         35
```

( 2 ) INFORMATION FOR SEQ ID NO:57:

( i ) SEQUENCE CHARACTERISTICS:
      ( A ) LENGTH: 39 amino acids
      ( B ) TYPE: amino acid
      ( D ) TOPOLOGY: both ( i i ) MOLECULE TYPE: peptide ( i x ) FEATURE:
      ( A ) NAME/KEY: Modified-site
      ( B ) LOCATION: 1
      ( D ) OTHER INFORMATION: /label=Dpr ( i x ) FEATURE:
      ( A ) NAME/KEY: Cross-links (B) LOCATION: 1..15

(x i) SEQUENCE DESCRIPTION: SEQ ID NO:57:

```
Xaa Thr Cys Phe Thr Tyr Lys Asp Lys Glu Cys Val Tyr Tyr Asp His
1               5               10                  15
Leu Asp Ile Ile Trp Val Asn Thr Pro Glu His Ile Val Pro Tyr Gly
            20              25                  30
Leu Gly Ser Pro Ser Arg Ser
            35
```

(2) INFORMATION FOR SEQ ID NO:58:

(i) SEQUENCE CHARACTERISTICS:
       (A) LENGTH: 39 amino acids
       (B) TYPE: amino acid
       (D) TOPOLOGY: both (ii) MOLECULE TYPE: peptide (ix) FEATURE:
       (A) NAME/KEY: Modified-site
       (B) LOCATION: 1
       (D) OTHER INFORMATION: /label=Dpr (ix) FEATURE:
       (A) NAME/KEY: Cross-links
       (B) LOCATION: 1..15

(x i) SEQUENCE DESCRIPTION: SEQ ID NO:58:

```
Xaa Thr Cys Phe Thr Tyr Lys Asp Lys Glu Cys Val Tyr Tyr Glu His
1               5               10                  15
Leu Asp Ile Ile Trp Val Asn Thr Pro Glu His Ile Val Pro Tyr Gly
            20              25                  30
Leu Gly Ser Pro Ser Arg Ser
            35
```

(2) INFORMATION FOR SEQ ID NO:59:

(i) SEQUENCE CHARACTERISTICS:
       (A) LENGTH: 38 amino acids
       (B) TYPE: amino acid
       (D) TOPOLOGY: both (ii) MOLECULE TYPE: peptide (ix) FEATURE:
       (A) NAME/KEY: Modified-site
       (B) LOCATION: 1
       (D) OTHER INFORMATION: /label=Dpr (ix) FEATURE:
       (A) NAME/KEY: Cross-links
       (B) LOCATION: 1..15

(x i) SEQUENCE DESCRIPTION: SEQ ID NO:59:

```
Xaa Ser Cys Lys Asp Met Thr Asp Lys Glu Cys Leu Asn Phe Asp His
1               5               10                  15
Gln Asp Val Ile Trp Val Asn Thr Pro Glu His Val Val Pro Tyr Gly
            20              25                  30
Leu Gly Ser Pro Arg Ser
            35
```

(2) INFORMATION FOR SEQ ID NO:60:

(i) SEQUENCE CHARACTERISTICS:
       (A) LENGTH: 38 amino acids
       (B) TYPE: amino acid
       (D) TOPOLOGY: both ( i i ) MOLECULE TYPE: peptide ( i x ) FEATURE:
            ( A ) NAME/KEY: Modified-site
            ( B ) LOCATION: 1
            ( D ) OTHER INFORMATION: /label=Dpr ( i x ) FEATURE:
            ( A ) NAME/KEY: Cross-links
            ( B ) LOCATION: 1..15

( x i ) SEQUENCE DESCRIPTION: SEQ ID NO:60:

Xaa Ser Cys Lys Asp Met Thr Asp Lys Glu Cys Leu Asn Phe Glu His
1               5                   10                  15

Gln Asp Val Ile Trp Val Asn Thr Pro Glu His Val Val Pro Tyr Gly
                20                  25                  30

Leu Gly Ser Pro Arg Ser
            35

( 2 ) INFORMATION FOR SEQ ID NO:61:

( i ) SEQUENCE CHARACTERISTICS:
            ( A ) LENGTH: 39 amino acids
            ( B ) TYPE: amino acid
            ( D ) TOPOLOGY: both ( i i ) MOLECULE TYPE: peptide ( i x ) FEATURE:
            ( A ) NAME/KEY: Modified-site
            ( B ) LOCATION: 1
            ( D ) OTHER INFORMATION: /label=Dpr ( i x ) FEATURE:
            ( A ) NAME/KEY: Cross-links
            ( B ) LOCATION: 1..15

( x i ) SEQUENCE DESCRIPTION: SEQ ID NO:61:

Xaa Ser Cys Lys Asp Met Thr Asp Lys Glu Cys Leu Asn Phe Asp His
1               5                   10                  15

Gln Asp Val Ile Trp Val Asn Thr Pro Glu His Ile Val Pro Tyr Gly
                20                  25                  30

Leu Gly Ser Pro Ser Arg Ser
            35

( 2 ) INFORMATION FOR SEQ ID NO:62:

( i ) SEQUENCE CHARACTERISTICS:
            ( A ) LENGTH: 39 amino acids
            ( B ) TYPE: amino acid
            ( D ) TOPOLOGY: both ( i i ) MOLECULE TYPE: peptide ( i x ) FEATURE:
            ( A ) NAME/KEY: Modified-site
            ( B ) LOCATION: 1
            ( D ) OTHER INFORMATION: /label=Dpr ( i x ) FEATURE:
            ( A ) NAME/KEY: Cross-links
            ( B ) LOCATION: 1..15

( x i ) SEQUENCE DESCRIPTION: SEQ ID NO:62:

Xaa Ser Cys Lys Asp Met Thr Asp Lys Glu Cys Leu Asn Phe Glu His
1               5                   10                  15

Gln Asp Val Ile Trp Val Asn Thr Pro Glu His Ile Val Pro Tyr Gly
                20                  25                  30

```
Leu Gly Ser Pro Ser Arg Ser
        35
```

( 2 ) INFORMATION FOR SEQ ID NO:63:

( i ) SEQUENCE CHARACTERISTICS:
        ( A ) LENGTH: 38 amino acids
        ( B ) TYPE: amino acid
        ( D ) TOPOLOGY: both ( i i ) MOLECULE TYPE: peptide ( i x ) FEATURE:
        ( A ) NAME/KEY: Modified-site
        ( B ) LOCATION: 1
        ( D ) OTHER INFORMATION: /label=Dpr ( i x ) FEATURE:
        ( A ) NAME/KEY: Cross-links
        ( B ) LOCATION: 1..15

( x i ) SEQUENCE DESCRIPTION: SEQ ID NO:63:

```
Xaa Ser Cys Lys Asp Met Thr Asp Lys Glu Cys Leu Tyr Phe Asp His
 1            5                   10                  15
Gln Asp Val Ile Trp Val Asn Thr Pro Glu His Val Val Pro Tyr Gly
            20                  25                  30
Leu Gly Ser Pro Arg Ser
        35
```

( 2 ) INFORMATION FOR SEQ ID NO:64:

( i ) SEQUENCE CHARACTERISTICS:
        ( A ) LENGTH: 38 amino acids
        ( B ) TYPE: amino acid
        ( D ) TOPOLOGY: both ( i i ) MOLECULE TYPE: peptide ( i x ) FEATURE:
        ( A ) NAME/KEY: Modified-site
        ( B ) LOCATION: 1
        ( D ) OTHER INFORMATION: /label=Dpr ( i x ) FEATURE:
        ( A ) NAME/KEY: Cross-links
        ( B ) LOCATION: 1..15

( x i ) SEQUENCE DESCRIPTION: SEQ ID NO:64:

```
Xaa Ser Cys Lys Asp Met Thr Asp Lys Glu Cys Leu Tyr Phe Glu His
 1            5                   10                  15
Gln Asp Val Ile Trp Val Asn Thr Pro Glu His Val Val Pro Tyr Gly
            20                  25                  30
Leu Gly Ser Pro Arg Ser
        35
```

( 2 ) INFORMATION FOR SEQ ID NO:65:

( i ) SEQUENCE CHARACTERISTICS:
        ( A ) LENGTH: 39 amino acids
        ( B ) TYPE: amino acid
        ( D ) TOPOLOGY: both ( i i ) MOLECULE TYPE: peptide ( i x ) FEATURE:
        ( A ) NAME/KEY: Modified-site
        ( B ) LOCATION: 1
        ( D ) OTHER INFORMATION: /label=Dpr ( i x ) FEATURE:
        ( A ) NAME/KEY: Cross-links ( B ) LOCATION: 1..15

( x i ) SEQUENCE DESCRIPTION: SEQ ID NO:65:

Xaa Ser Cys Lys Asp Met Thr Asp Lys Glu Cys Leu Tyr Phe Asp His
1               5                   10                  15

Gln Asp Val Ile Trp Val Asn Thr Pro Glu His Ile Val Pro Tyr Gly
            20                  25                  30

Leu Gly Ser Pro Ser Arg Ser
            35

( 2 ) INFORMATION FOR SEQ ID NO:66:

( i ) SEQUENCE CHARACTERISTICS:
      ( A ) LENGTH: 39 amino acids
      ( B ) TYPE: amino acid
      ( D ) TOPOLOGY: both ( i i ) MOLECULE TYPE: peptide ( i x ) FEATURE:
      ( A ) NAME/KEY: Modified-site
      ( B ) LOCATION: 1
      ( D ) OTHER INFORMATION: /label=Dpr ( i x ) FEATURE:
      ( A ) NAME/KEY: Cross-links
      ( B ) LOCATION: 1..15

( x i ) SEQUENCE DESCRIPTION: SEQ ID NO:66:

Xaa Ser Cys Lys Asp Met Thr Asp Lys Glu Cys Leu Tyr Phe Glu His
1               5                   10                  15

Gln Asp Val Ile Trp Val Asn Thr Pro Glu His Ile Val Pro Tyr Gly
            20                  25                  30

Leu Gly Ser Pro Ser Arg Ser
            35

( 2 ) INFORMATION FOR SEQ ID NO:67:

( i ) SEQUENCE CHARACTERISTICS:
      ( A ) LENGTH: 38 amino acids
      ( B ) TYPE: amino acid
      ( D ) TOPOLOGY: both ( i i ) MOLECULE TYPE: peptide ( i x ) FEATURE:
      ( A ) NAME/KEY: Modified-site
      ( B ) LOCATION: 1
      ( D ) OTHER INFORMATION: /label=Dpr ( i x ) FEATURE:
      ( A ) NAME/KEY: Cross-links
      ( B ) LOCATION: 1..15

( x i ) SEQUENCE DESCRIPTION: SEQ ID NO:67:

Xaa Ser Cys Lys Asp Met Thr Asp Glu Glu Cys Leu Asn Phe Asp His
1               5                   10                  15

Gln Asp Val Ile Trp Val Asn Thr Pro Glu His Val Val Pro Tyr Gly
            20                  25                  30

Leu Gly Ser Pro Arg Ser
            35

( 2 ) INFORMATION FOR SEQ ID NO:68:

( i ) SEQUENCE CHARACTERISTICS:
      ( A ) LENGTH: 38 amino acids
      ( B ) TYPE: amino acid
      ( D ) TOPOLOGY: both 5,492,892

83

-continued

84

( i i ) MOLECULE TYPE: peptide ( i x ) FEATURE:
  ( A ) NAME/KEY: Modified-site
  ( B ) LOCATION: 1
  ( D ) OTHER INFORMATION: /label=Dpr ( i x ) FEATURE:
  ( A ) NAME/KEY: Cross-links
  ( B ) LOCATION: 1..15

( x i ) SEQUENCE DESCRIPTION: SEQ ID NO:68:

```
Xaa  Ser  Cys  Lys  Asp  Met  Thr  Asp  Glu  Glu  Cys  Leu  Asn  Phe  Glu  His
1                   5                        10                       15
Gln  Asp  Val  Ile  Trp  Val  Asn  Thr  Pro  Glu  His  Val  Val  Pro  Tyr  Gly
                    20                       25                       30
Leu  Gly  Ser  Pro  Arg  Ser
                    35
```

( 2 ) INFORMATION FOR SEQ ID NO:69:

( i ) SEQUENCE CHARACTERISTICS:
    ( A ) LENGTH: 39 amino acids
    ( B ) TYPE: amino acid
    ( D ) TOPOLOGY: both ( i i ) MOLECULE TYPE: peptide ( i x ) FEATURE:
    ( A ) NAME/KEY: Modified-site
    ( B ) LOCATION: 1
    ( D ) OTHER INFORMATION: /label=Dpr ( i x ) FEATURE:
    ( A ) NAME/KEY: Cross-links
    ( B ) LOCATION: 1..15

( x i ) SEQUENCE DESCRIPTION: SEQ ID NO:69:

```
Xaa  Ser  Cys  Lys  Asp  Met  Thr  Asp  Glu  Glu  Cys  Leu  Asn  Phe  Asp  His
1                   5                        10                       15
Gln  Asp  Val  Ile  Trp  Val  Asn  Thr  Pro  Glu  His  Ile  Val  Pro  Tyr  Gly
                    20                       25                       30
Leu  Gly  Ser  Pro  Ser  Arg  Ser
                    35
```

( 2 ) INFORMATION FOR SEQ ID NO:70:

( i ) SEQUENCE CHARACTERISTICS:
    ( A ) LENGTH: 39 amino acids
    ( B ) TYPE: amino acid
    ( D ) TOPOLOGY: both ( i i ) MOLECULE TYPE: peptide ( i x ) FEATURE:
    ( A ) NAME/KEY: Modified-site
    ( B ) LOCATION: 1
    ( D ) OTHER INFORMATION: /label=Dpr ( i x ) FEATURE:
    ( A ) NAME/KEY: Cross-links
    ( B ) LOCATION: 1..15

( x i ) SEQUENCE DESCRIPTION: SEQ ID NO:70:

```
Xaa  Ser  Cys  Lys  Asp  Met  Thr  Asp  Glu  Glu  Cys  Leu  Asn  Phe  Glu  His
1                   5                        10                       15
Gln  Asp  Val  Ile  Trp  Val  Asn  Thr  Pro  Glu  His  Ile  Val  Pro  Tyr  Gly
                    20                       25                       30
```

Leu Gly Ser Pro Ser Arg Ser
                35

(2) INFORMATION FOR SEQ ID NO:71:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=Dnp (ix) FEATURE:
        (A) NAME/KEY: Modified-site
        (B) LOCATION: 1
        (D) OTHER INFORMATION: /label=Boc (ix) FEATURE:
        (A) NAME/KEY: Modified-site
        (B) LOCATION: 3
        (D) OTHER INFORMATION: /label=OBzl (xi) SEQUENCE DESCRIPTION: SEQ ID NO:71:

His Leu Asp Ile Ile Trp
1               5

(2) INFORMATION FOR SEQ ID NO:72:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label=Boc (ix) FEATURE:
        (A) NAME/KEY: Modified-site
        (B) LOCATION: 1
        (D) OTHER INFORMATION: /label=Fmoc (ix) FEATURE:
        (A) NAME/KEY: Modified-site
        (B) LOCATION: 2
        (D) OTHER INFORMATION: /label=Dnp (ix) FEATURE:
        (A) NAME/KEY: Modified-site
        (B) LOCATION: 4
        (D) OTHER INFORMATION: /label=OBzl (xi) SEQUENCE DESCRIPTION: SEQ ID NO:72:

Lys His Leu Asp Ile Ile Trp
1                   5

(2) INFORMATION FOR SEQ ID NO:73:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: Modified-site (B) LOCATION: 1
                (D) OTHER INFORMATION: /label=Boc (ix) FEATURE:
                (A) NAME/KEY: Modified-site
                (B) LOCATION: 1
                (D) OTHER INFORMATION: /label=Bzl (ix) FEATURE:
                (A) NAME/KEY: Modified-site
                (B) LOCATION: 2
                (D) OTHER INFORMATION: /label=4McBzl (ix) FEATURE:
                (A) NAME/KEY: Modified-site
                (B) LOCATION: 3
                (D) OTHER INFORMATION: /label=Bzl (ix) FEATURE:
                (A) NAME/KEY: Modified-site
                (B) LOCATION: 4
                (D) OTHER INFORMATION: /label=Bzl (ix) FEATURE:
                (A) NAME/KEY: Modified-site
                (B) LOCATION: 7
                (D) OTHER INFORMATION: /label=OBzl (ix) FEATURE:
                (A) NAME/KEY: Modified-site
                (B) LOCATION: 8
                (D) OTHER INFORMATION: /label=2-Cl-Z (ix) FEATURE:
                (A) NAME/KEY: Modified-site
                (B) LOCATION: 9
                (D) OTHER INFORMATION: /label=OBzl (ix) FEATURE:
                (A) NAME/KEY: Modified-site
                (B) LOCATION: 10
                (D) OTHER INFORMATION: /label=4McBzl (ix) FEATURE:
                (A) NAME/KEY: Modified-site
                (B) LOCATION: 12
                (D) OTHER INFORMATION: /label=2-Br-Z (ix) FEATURE:
                (A) NAME/KEY: Modified-site
                (B) LOCATION: 14
                (D) OTHER INFORMATION: /label=Fmoc (ix) FEATURE:
                (A) NAME/KEY: Modified-site
                (B) LOCATION: 15
                (D) OTHER INFORMATION: /label=Dnp (ix) FEATURE:
                (A) NAME/KEY: Modified-site
                (B) LOCATION: 17
                (D) OTHER INFORMATION: /label=OBzl (xi) SEQUENCE DESCRIPTION: SEQ ID NO:73:

Ser Cys Ser Ser Leu Met Asp Lys Glu Cys Val Tyr Phe Lys His Leu
1               5                   10                  15
Asp Ile Ile Trp
            20

(2) INFORMATION FOR SEQ ID NO:74:

(i) SEQUENCE CHARACTERISTICS:
                (A) LENGTH: 21 amino acids
                (B) TYPE: amino acid
                (D) TOPOLOGY: linear (ii) MOLECULE TYPE: peptide ( i x ) FEATURE:
  ( A ) NAME/KEY: Modified-site
  ( B ) LOCATION: 1
  ( D ) OTHER INFORMATION: /label=Boc ( i x ) FEATURE:
  ( A ) NAME/KEY: Modified-site
  ( B ) LOCATION: 1
  ( D ) OTHER INFORMATION: /label=OFm ( i x ) FEATURE:
  ( A ) NAME/KEY: Modified-site
  ( B ) LOCATION: 2
  ( D ) OTHER INFORMATION: /label=Bzl ( i x ) FEATURE:
  ( A ) NAME/KEY: Modified-site
  ( B ) LOCATION: 3
  ( D ) OTHER INFORMATION: /label=4McBzl ( i x ) FEATURE:
  ( A ) NAME/KEY: Modified-site
  ( B ) LOCATION: 4
  ( D ) OTHER INFORMATION: /label=Bzl ( i x ) FEATURE:
  ( A ) NAME/KEY: Modified-site
  ( B ) LOCATION: 5
  ( D ) OTHER INFORMATION: /label=Bzl ( i x ) FEATURE:
  ( A ) NAME/KEY: Modified-site
  ( B ) LOCATION: 8
  ( D ) OTHER INFORMATION: /label=OBzl ( i x ) FEATURE:
  ( A ) NAME/KEY: Modified-site
  ( B ) LOCATION: 9
  ( D ) OTHER INFORMATION: /label=2- Cl-Z ( i x ) FEATURE:
  ( A ) NAME/KEY: Modified-site
  ( B ) LOCATION: 10
  ( D ) OTHER INFORMATION: /label=OBzl ( i x ) FEATURE:
  ( A ) NAME/KEY: Modified-site
  ( B ) LOCATION: 11
  ( D ) OTHER INFORMATION: /label=4McBzl ( i x ) FEATURE:
  ( A ) NAME/KEY: Modified-site
  ( B ) LOCATION: 13
  ( D ) OTHER INFORMATION: /label=2- Br-Z ( i x ) FEATURE:
  ( A ) NAME/KEY: Modified-site
  ( B ) LOCATION: 15
  ( D ) OTHER INFORMATION: /label=Fmoc ( i x ) FEATURE:
  ( A ) NAME/KEY: Modified-site
  ( B ) LOCATION: 16
  ( D ) OTHER INFORMATION: /label=Dnp ( i x ) FEATURE:
  ( A ) NAME/KEY: Modified-site
  ( B ) LOCATION: 18
  ( D ) OTHER INFORMATION: /label=OBzl ( x i ) SEQUENCE DESCRIPTION: SEQ ID NO:74:

```
Asp  Ser  Cys  Ser  Ser  Leu  Met  Asp  Lys  Glu  Cys  Val  Tyr  Phe  Lys  His
 1              5                        10                            15
Leu  Asp  Ile  Ile  Trp
              20
```

( 2 ) INFORMATION FOR SEQ ID NO:75:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Boc ( i x ) FEATURE:
        ( A ) NAME/KEY: Modified-site
        ( B ) LOCATION: 2
        ( D ) OTHER INFORMATION: /label=Bzl ( i x ) FEATURE:
        ( A ) NAME/KEY: Modified-site
        ( B ) LOCATION: 3
        ( D ) OTHER INFORMATION: /label=4McBzl ( i x ) FEATURE:
        ( A ) NAME/KEY: Modified-site
        ( B ) LOCATION: 4
        ( D ) OTHER INFORMATION: /label=Bzl ( i x ) FEATURE:
        ( A ) NAME/KEY: Modified-site
        ( B ) LOCATION: 5
        ( D ) OTHER INFORMATION: /label=Bzl ( i x ) FEATURE:
        ( A ) NAME/KEY: Modified-site
        ( B ) LOCATION: 8
        ( D ) OTHER INFORMATION: /label=OBzl ( i x ) FEATURE:
        ( A ) NAME/KEY: Modified-site
        ( B ) LOCATION: 9
        ( D ) OTHER INFORMATION: /label=2- Cl-Z ( i x ) FEATURE:
        ( A ) NAME/KEY: Modified-site
        ( B ) LOCATION: 10
        ( D ) OTHER INFORMATION: /label=OBzl ( i x ) FEATURE:
        ( A ) NAME/KEY: Modified-site
        ( B ) LOCATION: 11
        ( D ) OTHER INFORMATION: /label=4McBzl ( i x ) FEATURE:
        ( A ) NAME/KEY: Modified-site
        ( B ) LOCATION: 13
        ( D ) OTHER INFORMATION: /label=2- Br-Z ( i x ) FEATURE:
        ( A ) NAME/KEY: Modified-site
        ( B ) LOCATION: 16
        ( D ) OTHER INFORMATION: /label=Dnp ( i x ) FEATURE:
        ( A ) NAME/KEY: Modified-site
        ( B ) LOCATION: 18
        ( D ) OTHER INFORMATION: /label=OBzl ( x i ) SEQUENCE DESCRIPTION: SEQ ID NO:75:

```
Asp  Ser  Cys  Ser  Ser  Leu  Met  Asp  Lys  Glu  Cys  Val  Tyr  Phe  Lys  His
1                   5                        10                       15
Leu  Asp  Ile  Ile  Trp
               20
```

( 2 ) INFORMATION FOR SEQ ID NO:76:

( i ) SEQUENCE CHARACTERISTICS:
    ( A ) LENGTH: 21 amino acids
    ( B ) TYPE: amino acid
    ( D ) TOPOLOGY: both ( i i ) MOLECULE TYPE: peptide ( i x ) FEATURE:
    ( A ) NAME/KEY: Modified-site
    ( B ) LOCATION: 1
    ( D ) OTHER INFORMATION: /label=Boc ( i x ) FEATURE:
    ( A ) NAME/KEY: Modified-site
    ( B ) LOCATION: 2
    ( D ) OTHER INFORMATION: /label=Bzl ( i x ) FEATURE:
    ( A ) NAME/KEY: Modified-site
    ( B ) LOCATION: 3
    ( D ) OTHER INFORMATION: /label=4McBzl ( i x ) FEATURE:
    ( A ) NAME/KEY: Modified-site
    ( B ) LOCATION: 4
    ( D ) OTHER INFORMATION: /label=Bzl ( i x ) FEATURE:
    ( A ) NAME/KEY: Modified-site
    ( B ) LOCATION: 5
    ( D ) OTHER INFORMATION: /label=Bzl ( i x ) FEATURE:
    ( A ) NAME/KEY: Modified-site
    ( B ) LOCATION: 8
    ( D ) OTHER INFORMATION: /label=OBzl ( i x ) FEATURE:
    ( A ) NAME/KEY: Modified-site
    ( B ) LOCATION: 9
    ( D ) OTHER INFORMATION: /label=2-Cl-Z ( i x ) FEATURE:
    ( A ) NAME/KEY: Modified-site
    ( B ) LOCATION: 10
    ( D ) OTHER INFORMATION: /label=OBzl ( i x ) FEATURE:
    ( A ) NAME/KEY: Modified-site
    ( B ) LOCATION: 11
    ( D ) OTHER INFORMATION: /label=4McBzl ( i x ) FEATURE:
    ( A ) NAME/KEY: Modified-site
    ( B ) LOCATION: 13
    ( D ) OTHER INFORMATION: /label=2-Br-Z ( i x ) FEATURE:
    ( A ) NAME/KEY: Modified-site
    ( B ) LOCATION: 16
    ( D ) OTHER INFORMATION: /label=Dnp ( i x ) FEATURE:
    ( A ) NAME/KEY: Modified-site
    ( B ) LOCATION: 18
    ( D ) OTHER INFORMATION: /label=OBzl ( i x ) FEATURE:
    ( A ) NAME/KEY: Cross-links
    ( B ) LOCATION: 1..15

( x i ) SEQUENCE DESCRIPTION: SEQ ID NO:76:

Asp Ser Cys Ser Ser Leu Met Asp Lys Glu Cys Val Tyr Phe Lys His
1               5                   10                  15
Leu Asp Ile Ile Trp
            20

( 2 ) INFORMATION FOR SEQ ID NO:77:

( i ) SEQUENCE CHARACTERISTICS:
        ( A ) LENGTH: 21 amino acids
        ( B ) TYPE: amino acid
        ( D ) TOPOLOGY: both ( i i ) MOLECULE TYPE: peptide ( i x ) FEATURE:
        ( A ) NAME/KEY: Cross-links
        ( B ) LOCATION: 1..15

( x i ) SEQUENCE DESCRIPTION: SEQ ID NO:77:

```
Asp Ser Cys Ser Ser Leu Met Asp Lys Glu Cys Val Tyr Phe Lys His
1               5                   10                  15
Leu Asp Ile Ile Trp
            20
```

( 2 ) INFORMATION FOR SEQ ID NO:78:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Boc ( i x ) FEATURE:
        ( A ) NAME/KEY: Modified-site
        ( B ) LOCATION: 1
        ( D ) OTHER INFORMATION: /label=Dnp ( i x ) FEATURE:
        ( A ) NAME/KEY: Modified-site
        ( B ) LOCATION: 3
        ( D ) OTHER INFORMATION: /label=OBzl ( x i ) SEQUENCE DESCRIPTION: SEQ ID NO:78:

```
His Leu Asp Ile Ile Trp
1               5
```

( 2 ) INFORMATION FOR SEQ ID NO:79:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Fmoc ( i x ) FEATURE:
        ( A ) NAME/KEY: Modified-site
        ( B ) LOCATION: 1
        ( D ) OTHER INFORMATION: /label=tBu ( i x ) FEATURE:
        ( A ) NAME/KEY: Modified-site
        ( B ) LOCATION: 2
        ( D ) OTHER INFORMATION: /label=Dnp ( i x ) FEATURE:
        ( A ) NAME/KEY: Modified-site
        ( B ) LOCATION: 4
        ( D ) OTHER INFORMATION: /label=OBzl ( x i ) SEQUENCE DESCRIPTION: SEQ ID NO:79:

Glu His Leu Asp Ile Ile Trp
1               5

( 2 ) INFORMATION FOR SEQ ID NO:80:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Fmoc ( i x ) FEATURE:
        ( A ) NAME/KEY: Modified-site
        ( B ) LOCATION: 1
        ( D ) OTHER INFORMATION: /label=Bzl ( i x ) FEATURE:
        ( A ) NAME/KEY: Modified-site
        ( B ) LOCATION: 2
        ( D ) OTHER INFORMATION: /label=McBzl ( i x ) FEATURE:
        ( A ) NAME/KEY: Modified-site
        ( B ) LOCATION: 3
        ( D ) OTHER INFORMATION: /label=Bzl ( i x ) FEATURE:
        ( A ) NAME/KEY: Modified-site
        ( B ) LOCATION: 4
        ( D ) OTHER INFORMATION: /label=Bzl ( i x ) FEATURE:
        ( A ) NAME/KEY: Modified-site
        ( B ) LOCATION: 7
        ( D ) OTHER INFORMATION: /label=OBzl ( i x ) FEATURE:
        ( A ) NAME/KEY: Modified-site
        ( B ) LOCATION: 8
        ( D ) OTHER INFORMATION: /label=2- Cl-Z ( i x ) FEATURE:
        ( A ) NAME/KEY: Modified-site
        ( B ) LOCATION: 9
        ( D ) OTHER INFORMATION: /label=OBzl ( i x ) FEATURE:
        ( A ) NAME/KEY: Modified-site
        ( B ) LOCATION: 10
        ( D ) OTHER INFORMATION: /label=McBzl ( i x ) FEATURE:
        ( A ) NAME/KEY: Modified-site
        ( B ) LOCATION: 12
        ( D ) OTHER INFORMATION: /label=2- Br-Z ( i x ) FEATURE:
        ( A ) NAME/KEY: Modified-site
        ( B ) LOCATION: 14
        ( D ) OTHER INFORMATION: /label=tBu ( i x ) FEATURE:
        ( A ) NAME/KEY: Modified-site
        ( B ) LOCATION: 15
        ( D ) OTHER INFORMATION: /label=Dnp ( i x ) FEATURE:
        ( A ) NAME/KEY: Modified-site
        ( B ) LOCATION: 17
        ( D ) OTHER INFORMATION: /label=OBzl ( x i ) SEQUENCE DESCRIPTION: SEQ ID NO:80:

Ser Cys Ser Ser Leu Met Asp Lys Glu Cys Val Tyr Phe Glu His Leu
1               5                   10                  15
Asp Ile Ile Trp
            20

( 2 ) INFORMATION FOR SEQ ID NO:81:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Fmoc ( i x ) FEATURE:
        ( A ) NAME/KEY: Modified-site
        ( B ) LOCATION: 1
        ( D ) OTHER INFORMATION: /label=Boc ( i x ) FEATURE:
        ( A ) NAME/KEY: Modified-site
        ( B ) LOCATION: 2
        ( D ) OTHER INFORMATION: /label=Bzl ( i x ) FEATURE:
        ( A ) NAME/KEY: Modified-site
        ( B ) LOCATION: 3
        ( D ) OTHER INFORMATION: /label=MeBzl ( i x ) FEATURE:
        ( A ) NAME/KEY: Modified-site
        ( B ) LOCATION: 4
        ( D ) OTHER INFORMATION: /label=Bzl ( i x ) FEATURE:
        ( A ) NAME/KEY: Modified-site
        ( B ) LOCATION: 5
        ( D ) OTHER INFORMATION: /label=Bzl ( i x ) FEATURE:
        ( A ) NAME/KEY: Modified-site
        ( B ) LOCATION: 8
        ( D ) OTHER INFORMATION: /label=OBzl ( i x ) FEATURE:
        ( A ) NAME/KEY: Modified-site
        ( B ) LOCATION: 9
        ( D ) OTHER INFORMATION: /label=2- Cl-Z ( i x ) FEATURE:
        ( A ) NAME/KEY: Modified-site
        ( B ) LOCATION: 10
        ( D ) OTHER INFORMATION: /label=OBzl ( i x ) FEATURE:
        ( A ) NAME/KEY: Modified-site
        ( B ) LOCATION: 11
        ( D ) OTHER INFORMATION: /label=MeBzl ( i x ) FEATURE:
        ( A ) NAME/KEY: Modified-site
        ( B ) LOCATION: 13
        ( D ) OTHER INFORMATION: /label=2- Br-Z ( i x ) FEATURE:
        ( A ) NAME/KEY: Modified-site
        ( B ) LOCATION: 15
        ( D ) OTHER INFORMATION: /label=tBu ( i x ) FEATURE:

(A) NAME/KEY: Modified-site
            (B) LOCATION: 16
            (D) OTHER INFORMATION: /label=Dnp (ix) FEATURE:
            (A) NAME/KEY: Modified-site
            (B) LOCATION: 18
            (D) OTHER INFORMATION: /label=OBzl (xi) SEQUENCE DESCRIPTION: SEQ ID NO:81:

Lys Ser Cys Ser Ser Leu Met Asp Lys Glu Cys Val Tyr Phe Glu His
1               5                   10                  15

Leu Asp Ile Ile Trp
            20

(2) INFORMATION FOR SEQ ID NO:82:

(i) SEQUENCE CHARACTERISTICS:
            (A) LENGTH: 21 amino acids
            (B) TYPE: amino acid
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /label=Fmoc (ix) FEATURE:
            (A) NAME/KEY: Modified-site
            (B) LOCATION: 2
            (D) OTHER INFORMATION: /label=Bzl (ix) FEATURE:
            (A) NAME/KEY: Modified-site
            (B) LOCATION: 3
            (D) OTHER INFORMATION: /label=MeBzl (ix) FEATURE:
            (A) NAME/KEY: Modified-site
            (B) LOCATION: 4
            (D) OTHER INFORMATION: /label=Bzl (ix) FEATURE:
            (A) NAME/KEY: Modified-site
            (B) LOCATION: 5
            (D) OTHER INFORMATION: /label=Bzl (ix) FEATURE:
            (A) NAME/KEY: Modified-site
            (B) LOCATION: 8
            (D) OTHER INFORMATION: /label=OBzl (ix) FEATURE:
            (A) NAME/KEY: Modified-site
            (B) LOCATION: 9
            (D) OTHER INFORMATION: /label=2-Cl-Z (ix) FEATURE:
            (A) NAME/KEY: Modified-site
            (B) LOCATION: 10
            (D) OTHER INFORMATION: /label=OBzl (ix) FEATURE:
            (A) NAME/KEY: Modified-site
            (B) LOCATION: 11
            (D) OTHER INFORMATION: /label=MeBzl (ix) FEATURE:
            (A) NAME/KEY: Modified-site
            (B) LOCATION: 13
            (D) OTHER INFORMATION: /label=2-Br-Z (ix) FEATURE:
            (A) NAME/KEY: Modified-site
            (B) LOCATION: 16

( D ) OTHER INFORMATION: /label=Dnp ( i x ) FEATURE:
    ( A ) NAME/KEY: Modified-site
    ( B ) LOCATION: 18
    ( D ) OTHER INFORMATION: /label=OBzl ( x i ) SEQUENCE DESCRIPTION: SEQ ID NO:82:

```
Lys  Ser  Cys  Ser  Ser  Leu  Met  Asp  Lys  Glu  Cys  Val  Tyr  Phe  Glu  His
 1              5                        10                       15
Leu  Asp  Ile  Ile  Trp
               20
```

( 2 ) INFORMATION FOR SEQ ID NO:83:

( i ) SEQUENCE CHARACTERISTICS:
        ( A ) LENGTH: 21 amino acids
        ( B ) TYPE: amino acid
        ( D ) TOPOLOGY: both ( i i ) MOLECULE TYPE: peptide ( i x ) FEATURE:
        ( A ) NAME/KEY: Modified-site
        ( B ) LOCATION: 1
        ( D ) OTHER INFORMATION: /label=Fmoc ( i x ) FEATURE:
        ( A ) NAME/KEY: Modified-site
        ( B ) LOCATION: 2
        ( D ) OTHER INFORMATION: /label=Bzl ( i x ) FEATURE:
        ( A ) NAME/KEY: Modified-site
        ( B ) LOCATION: 3
        ( D ) OTHER INFORMATION: /label=McBzl ( i x ) FEATURE:
        ( A ) NAME/KEY: Modified-site
        ( B ) LOCATION: 4
        ( D ) OTHER INFORMATION: /label=Bzl ( i x ) FEATURE:
        ( A ) NAME/KEY: Modified-site
        ( B ) LOCATION: 5
        ( D ) OTHER INFORMATION: /label=Bzl ( i x ) FEATURE:
        ( A ) NAME/KEY: Modified-site
        ( B ) LOCATION: 8
        ( D ) OTHER INFORMATION: /label=OBzl ( i x ) FEATURE:
        ( A ) NAME/KEY: Modified-site
        ( B ) LOCATION: 9
        ( D ) OTHER INFORMATION: /label=2- Cl- Z ( i x ) FEATURE:
        ( A ) NAME/KEY: Modified-site
        ( B ) LOCATION: 10
        ( D ) OTHER INFORMATION: /label=OBzl ( i x ) FEATURE:
        ( A ) NAME/KEY: Modified-site
        ( B ) LOCATION: 11
        ( D ) OTHER INFORMATION: /label=McBzl ( i x ) FEATURE:
        ( A ) NAME/KEY: Modified-site
        ( B ) LOCATION: 13
        ( D ) OTHER INFORMATION: /label=2- Br-Z ( i x ) FEATURE:
        ( A ) NAME/KEY: Modified-site
        ( B ) LOCATION: 16
        ( D ) OTHER INFORMATION: /label=Dnp

```
( i x ) FEATURE:
        ( A ) NAME/KEY: Modified-site
        ( B ) LOCATION: 18
        ( D ) OTHER INFORMATION: /label=OBzl ( i x ) FEATURE:
        ( A ) NAME/KEY: Cross-links
        ( B ) LOCATION: 1..15

( x i ) SEQUENCE DESCRIPTION: SEQ ID NO:83:
```

Lys Ser Cys Ser Ser Leu Met Asp Lys Glu Cys Val Tyr Phe Glu His
 1               5                   10                      15
Leu Asp Ile Ile Trp
             20

```
( 2 ) INFORMATION FOR SEQ ID NO:84:

( i ) SEQUENCE CHARACTERISTICS:
                ( A ) LENGTH: 21 amino acids
                ( B ) TYPE: amino acid
                ( D ) TOPOLOGY: both ( i i ) MOLECULE TYPE: peptide ( i x ) FEATURE:
                ( A ) NAME/KEY: Cross-links
                ( B ) LOCATION: 1..15

( x i ) SEQUENCE DESCRIPTION: SEQ ID NO:84:
```

Lys Ser Cys Ser Ser Leu Met Asp Lys Glu Cys Val Tyr Phe Glu His
 1               5                   10                      15
Leu Asp Ile Ile Trp
             20

ENDOTHELIN ANTAGONISTS

This is a continuation of application Ser. No. 666,294 filed on Mar. 8, 1991, now abandoned.

This work was supported by grants from the American Heart Association, New York State Affiliate.

This invention relates to novel polypeptides and their precursors which have endothelin antagonist activity. This invention also relates to pharmaceutical compositions containing effective amounts of endothelin antagonists as well as processes for treating in animals pathological conditions caused or mediated by endothelins, such as vasoconstriction and cell proliferation.

BACKGROUND OF THE INVENTION

Endothelin is a potent vasoconstrictor peptide of endothelial origin (Yanagisawa, M. et al., Nature 1988, 332: 411–415), and may represent a family of vasoconstrictors. Three distinct endothelin isopeptides are known (termed herein as Et-1, Et-2, Et-3) all of which cause vasoconstriction in a number of vascular beds. Et-1 is a 21-residue peptide with two disulfide bonds and shows extensive homology with the two other known forms of the peptide (Hirata, Y., et al., Biochem. Biophys Res. Commun., 1984, 160; 228–34).

A structural model based on the endothelin amino acid sequence has been proposed. The molecule is amphipathic consisting of a rigid, disulfide bonded, hydrophilic amino-terminal half of the molecule with two turns, and has extended hydrophobic sheet structure comprising the C-terminal half of the molecule (Spinella, M. J., et al., Peptide Res., 1989 2, 286–91). The extended structure may be stabilized by intermolecular hydrogen bonding, leading to dimers or higher order aggregates in solution and is hydrophobic enough to partition into an organic solvent such as ether, as long as the molecule can keep its hydrophilic amino terminus in an aqueous phase. Several different types of microcrystals of Et-1 have been formed at an aqueous/organic boundary in a two-phase system but precise tertiary structure of endothelin via X-ray crystallography has not yet been established.

In addition, certain peptide toxins found in the venom of the asp, Atractaspis engaddensis, termed sarafotoxins S, are known which have endothelin activity causing severe coronary vasospasm in snake bite victims. The sarafotoxins display significant structural and functional homology to the endothelins. The amino acid sequence of the endothelins and sarafotoxins S are shown hereinbelow in Table 1.

TABLE 1

| Peptide Designation[2] | Amino Acid Sequence[1] Of Naturally Occurring Endothelin Active Peptides | | | | |
|---|---|---|---|---|---|
| | 1 | 5 | 10 | 15 | 20 |
| Et-1 | Cys Ser Cys Ser | Ser Leu Met Asp Lys | Glu Cys Val Tyr Phe | Cys His Leu Asp Ile | Ile Trp |
| Et-2 | Cys Ser Cys Ser | Ser Trp Leu Asp Lys | Glu Cys Val Tyr Phe | Cys His Leu Asp Ile | Ile Trp |
| Et-3 | Cys Thr Cys Phe | Thr Tyr Lys Asp Lys | Glu Cys Val Tyr Tyr | Cys His Leu Asp Ile | Ile Trp |
| SB | Cys Ser Cys Lys | Asp Met Thr Asp Lys | Glu Cys Leu Tyr Phe | Cys His Gln Asp Val | Ile Trp |
| SA | Cys Ser Cys Lys | Asp Met Thr Asp Lys | Glu Cys Leu Asn Phe | Cys His Gln Asp Val | Ile Trp |
| SC | Cys Ser Cys Lys | Asp Met Thr Asp Glu | Glu Cys Leu Asn Phe | Cys His Gln Asp Val | Ile Trp |

[1]Amino acid positions are numbered starting at the N-terminal cysteine moiety.
[2]Et-1, Et-2, Et-3 denote Endothelin 1, Endothelin 2 and Endothelin 3 respectively. SB, SA, SC denote sarafotoxin S6b, Sarafotoxin S6a1 and Sarafotoxin S6c respectively.

The endothelin active polypeptides depicted in Table 1 all contain 21 amino acid residues. All of them possess a cysteine residue at positions 1, 3, 11 and 15 from the N-terminus. In fact the native peptide depicted in Table 1 is folded so that the cysteines at positions 1 and 15 form a disulfide bond and the cysteines at positions 3 and 11 form another disulfide bond. For example, the amino acid sequence of Et-1 is depicted hereinbelow.

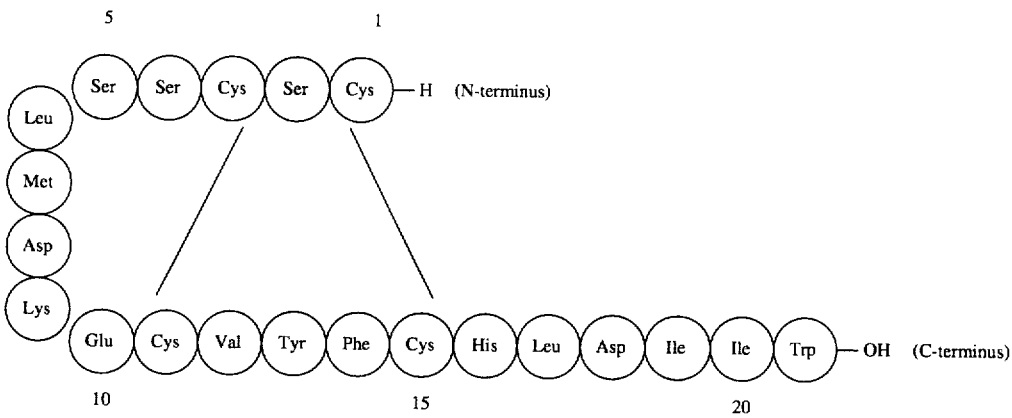

The Et-1 depicted hereinabove specifically shows that the cysteines at positions 1 and 15 form a bond and the cysteines at positions 3 and 11 form another bond. A closer examination of Et-1 clearly reveals that the linkages are disulfide bonds:

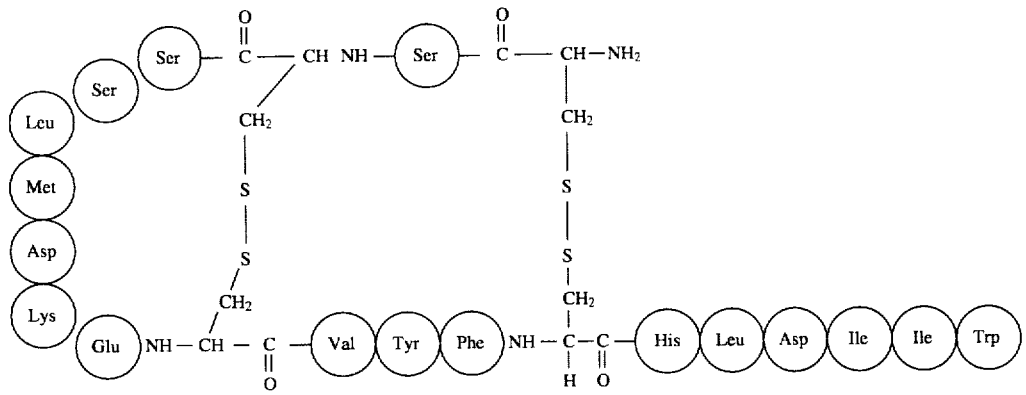

In the above formula, the chemical formula for the cysteine residues at positions 1, 3, 11 and 15 are specifically drawn. As clearly shown, the atoms connecting the cysteines at positions 1 and 15 and the cysteines at position 3 and 11 are $CH_2$—S—S—$CH_2$. The atoms linking the amino acids at position 1 and 15 together with the amino residues between these two positions inclusively, constitute an "outer bridge or loop", while those atoms linking the amino acids at position 3 and 11 together with the amino acid residues between positions 3 and 11 inclusively, constitute the "inner bridge or loop".

Before proceeding further, the terminology used will be briefly explained. Peptides are identified by amino acid sequence using established abbreviations. For example, as used herein, in the case of the commonly occurring amino acids, "Gly" stands for glycine, "Leu" stands for Leucine, "Cys" stands for cysteine, etc. Except for glycine, the amino acids depicted in the above table are considered to exist as stereoisomers in the L-configuration. Et-1, Et-2, Et-3, SA, SB, SC designate known endothelin-active polypeptides whose sequences are shown in Table 1. Amino acid moieties in polypeptides are numbered sequentially starting at the N-terminus. Positions of amino acids within the polypeptides are represented by superscripts adjacent to the amino acid designations. For example, position 1 in the naturally occurring endothelin-active polypeptides is occupied by cysteine in all cases and can be represented by "$Cys^1$". Phenylalanine at position 4 in Et-3 is represented as "$Phe^4$" Leucine at position 12 of SB as "$Leu^{12}$" trytophan at position 6 of Et-2 as "$Trp^6$" and so on. Truncated peptides of the endothelin-active series will be designated with reference to the sequences in Table 1. Thus "$Et-1^{1-10}$" denotes a decapeptide with the amino acid sequence shown for the first ten positions in Et-1 (See Table 1), "$Et-3^{15-20}$", a hexapeptide with amino acid sequence shown for positions 15–20 for Et-3; and "$SB^{1-20}$", a peptide with sequence shown for the first 20 positions of SB.

Analogs created by substitution of amino acids or other chemical moieties for the known amino acids of endothelin-active peptides are designated according to position and the amino acid substitution. Thus, an endothelin analog of Et-1 with alanine substituted for cysteine at positions 1 and 15 is designated [$Ala^{1,15}$]Et-1, and an analog of Et-2 with phenylalanine at position 21 is designated "[$Phe^{21}$]Et-2".

The positions of disulfide bridges between cysteine moieties are designated by connecting their position numbers with a dash. Thus, naturally occurring endothelin-1 containing two disulfide bridges may be depicted as "[$Cys^{1-15}$, $Cys^{3-11}$]Et-1" (when referring to the disulfide bridge structure) On the other hand "[$Cys^{1,15}$, $Cys^{3-11}$]Et-1" denotes the same polypeptide with reduced cysteine at positions 1 and 15 (no disulfide bridge between the positions).

The positions of the bridging structure replacements for the disulfide bridges between cysteine moieties of the native endothelins is denoted connecting the replacement amino acids designations/positions with a line

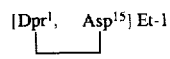

For example,

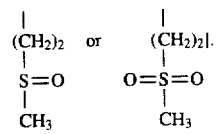

denotes that the $Cys^{1-15}$ disulfide constituting the outer loop bridging structure of Et-1 has Cys replaced with Dpr (diaminopropionic acid moiety) at position 1 with Asp at position 15, and that the two amino acid moieties participate in a bridging structure, for example, through an amide bond.

Analogs of the polypeptides in Table 1 wherein one or more amino acid substitutions, additions or deletions have been made are known. For example, [$Ala^{3,11}$]Et-1 shows endothelin activity (Randall, et al., *Br. J. Pharmacol*, 1984, 98, 685–699). [$Homoserine^6$]SB shows endothelin activity (Kitazuni, *FEBS Letters*, 1990, 260, 269–72). [$Ala^4$]Et-1, [$Ala^5$]Et-1, [$Gly^6$]Et-1, [$Met(O)^7$]Et-1, [$Asn^8$]Et-1, [$Leu^9$] Et-1, [$Phe^{13}$]Et-1, [$Tyr^{21}$]Et-1, and [$Phe^{21}$]Et-1 show appreciable endothelin activity (Nakajima, et al., *Biochem Biophys Res Commu.*, 1989, 163, 424–9). [By definition, [met] [O] refers to an oxidized methionine e.g. the side group is $$\begin{array}{cc} | & | \\ (CH_2)_2 & \text{or} \quad (CH_2)_2| \\ | & | \\ S=O & O=S=O \\ | & | \\ CH_3 & CH_3 \end{array}$$

Yet other types of analogs of the polypeptides shown in Table 1 have been shown to have endothelin activity, for example Et-1 in which the $Glu^{10}$ residue has been anisylated (Hiley, et al., *Br. J. Pharmacol*, 1990, 101, 319–24) and Lys-Arg-Et-1 (Et-1 extended through the addition of lysylarginine to the N-terminus; see Nakajima, op. cit.). Endothelin precursors, i.e., polypeptides containing more than 21 amino acids, which when cleaved chemically or enzymatically produce an endothelin active polypeptide, have been identified. For example, endothelin precursors with 38 (human) or 39 (porcine) amino acids have been identified (so called "Big Et-1") which are subsequently processed in vivo by an endothelin cleaving enzyme to produce mature Et-1 (Yanigasawa, et al., *Biochem. Pharmacol.* 1,989, 38, 1877–83); Yanigasawa, et al., *Nature*, 1988, 332, 411–15). It is contemplated that several such polypeptide precursors exist or otherwise could be synthesized by art known methods which are processable in vivo to form endothelin-active polypeptides.

The mode of action of the endothelins and sarafotoxins in eliciting vasoconstriction is still a matter of intense inquiry. The three distinct endothelins cause vasoconstriction in a number of vascular beds with an apparent potency order of: Et-2>Et-1>Et-3 (Anggard, et al. *Blood. Vessels* 1990, 29 269–81). Two distinct endothelin receptors have been cloned, one of which appears to be specific for Et-1 (Arai., et al. *Nature*, 1990, 348, 730–2) while the other interacts with all three Et polypeptides (Sakurai et al *Nature* 1990, 348 732–4).

Competitive binding studies have suggested multiple classes of receptors with varying affinities for the different endothelins anti that the distribution of the receptor subtypes is tissue specific (Simonson, et al *FASEB J.*, 1990, 4, 2989–3000); Martin. et al. *Biochem. Biophys. Res Commun.* 1989, 162, 130–7); Kloog, et al. *FEBS Letters*, 1989, 253, 199–202. Thus, it should be appreciated that more than one type of endothelin-active polypeptide exists and that more may be discovered with widely different levels of activity in different tissues. In like manner, the endothelin antagonists of the present invention may be tissue specific since they are structural analogs of the endothelin-active polypeptides.

It is important to note that the known endothelins, whether naturally occurring or synthesized, have a disulfide bridge and more specifically a $CH_2$—S—S—$CH_2$ group in the outer bridge. The cysteine at positions 1 and 15 and the outer bridge is believed to be necessary for the polypeptides in Table 1 to possess endothelin activity.

A recent report by Fabregat, et al. (*J. Cellular Physiol* 1990 145:88–94) describes a substance P based peptide analog ([D-Arg$^1$, D-Phe$^5$, D-Trp$^{7,9}$, Leu$^{11}$] substance P) that blocks certain endothelin responses and is able to inhibit $^{125}$I-labelled Et-1 binding to an Et-1 receptor in a competitive and dose dependent manner. This peptide is an undecapeptide containing no cysteine residues. Neither is it related in structure to the known endothelin-active peptides or to the novel endothelin antagonists and precursors which are the subject of the present invention.

SUMMARY OF THE INVENTION

The present invention provides structural analogs of endothelin peptides which halve endothelin antagonist activity. It has been surprisingly discovered that structural analogs wherein the outer disulfide bridge of endothelin-active peptides is replaced by a physiologically stable covalently bonded non-disulfide linkage display antagonist activity in that they have the ability to block the vasoconstrictor or vasopressor action of endothelin-active polypeptides in vascular systems.

The polypeptides of the present invention are useful in treating various cardiovascular disorders, such as hypertension, including systemic, pulmonary and hepatic portal hypertension; atherosclerosis; vasospasms, including cerebral, coronary, artery or pulmonary vasospasm; asthma; and renal failure. In addition, the compounds of the present invention are useful in treating snake bites. Thus, the present invention is also directed to a method of treating animals, including mammals, afflicted with such disorders by administering to said animal a therapeutically effective amount of the endothelin antagonists of the present invention.

More specifically, the present invention is directed to compounds which comprise an endothelin antagonist polypeptide that is at least 40% homologous to an endothelin active polypeptide consisting of Et-1, Et-2, Et-3, SC, SA and SB. The compounds of the present invention have the formula:

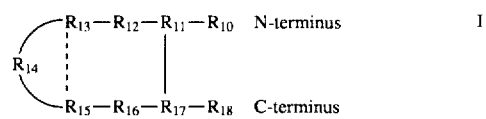

and pharmaceutically acceptable salts thereof wherein
$R_{11}$ is $AA_1$;
$AA_1$ is

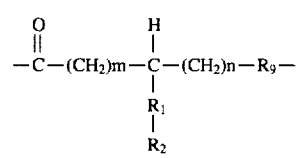

m and n are are independently 0 or 1 and $m+n \leq 1$;
$R_{17}$ is $AA_{15}$;
$AA_{15}$ is a residue having the formula:

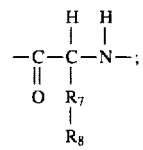

$R_{13}$ is $AA_3$;
$AA_3$ is an amino acid residue or a residue having the formula:

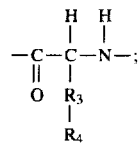

$R_{15}$ is $AA_{11}$;
$AA_{11}$ is an amino acid residue or a residue having the formula:

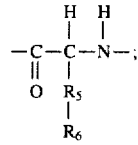

$R_1$, $R_3$, $R_5$ and $R_7$ are independently a chemical bond, an alkylene containing up to 4 carbon atoms in the principal chain and a total of 8 carbon atoms, arylene, lower cycloalkylene or aryl lower alkylene, said arylene, lower cycloalkylene or aryl lower alkylene may be unsubstituted or substituted with lower alkyl;

$R_2$ and $R_8$ are covalently bonded to each other and $R_2$ and $R_8$ taken together are $$\begin{array}{cccc} \text{H} & \text{H} & & \\ | & | & & \\ \text{C}-\text{N}-, & \text{N}-\text{C}-, & \text{C}-\text{O}, & \text{O}-\text{C}, \\ \| & \| & \| & \| \\ \text{O} & \text{O} & \text{O} & \text{O} \end{array}$$

HC=CH, O-ALK, or ALK-O $$\begin{array}{cccc} \text{H} & & \text{H} & \\ | & & | & \\ \text{N}-\text{ALK}, & \text{ALK}-\text{N}, & \text{ALK}-\text{C}-, & \text{C}-\text{ALK}, \\ & & \| & \| \\ & & \text{O} & \text{O} \end{array}$$

ALK, S-Alk, or ALK-S, wherein ALK is an alkyene containing 1 or 2, carbon atoms in the principal chain and up to a total of 4 carbon atoms with the proviso that when both $R_1$ and $R_7$ are chemical bonds then $R_2$ taken together with $R_8$ is ALK;

$R_4$ and $R_6$ are independently hydrogen, lower alkyl which may be unsubstituted or substituted with a hydroxy group or $R_4$ and $R_6$ taken together form a —S—S—, $$\begin{array}{cccc} & & & \text{H} \\ & & & | \\ -\text{C}-\text{O}, & -\text{O}-\text{C}-, & -\text{NH}-\text{C}-, & \text{C}-\text{N}, \\ \| & \| & \| & \| \\ \text{O} & \text{O} & \text{O} & \text{O} \end{array}$$

HC=CH, ALK—O—, O-ALK, $$\begin{array}{c} \text{C}-\text{ALK}, \\ \| \\ \text{O} \end{array}$$

ALK-S S-ALK $$\begin{array}{c} \text{O} \\ \| \\ \text{ALK}-\text{C}, \end{array}$$

—HC=CH—, $$\begin{array}{cc} \text{H} & \text{H} \\ | & | \\ \text{N}-\text{ALK}, & \text{ALK}-\text{N}, \end{array}$$

or ALK wherein ALK is an alkylene containing 1 or 2 carbon atoms in the principal chain and up to a total of 4 carbon atoms, with the proviso that when both $R_3$ and $R_5$ are chemical bonds, then $R_4$ and $R_6$ taken together is ALK, $R_9$ is NH, chemical bond or lower alkylene;

$R_{10}$ is H, lower alkyl, an amino acid residue or a peptide residue containing up to 5 amino acids provided that if $R_{10}$ a peptide or amino acid residue, then $R_9$ is $$\begin{array}{c} \text{H;} \\ | \\ \text{N} \end{array}$$

$R_{12}$ is an amino acid residue or a peptide residue containing from 2–3 amino acids;

$R_{14}$ is a peptide residue containing from 2–5 amino acids;

$R_{18}$ is an amino acid residue or peptide residue containing from 2–10 amino acids, wherein the total number of amino acid residues in $R_{10}$, $R_{12}$, $R_{14}$, $R_{16}$, $R_{18}$ ranges from 12–21 amino acids.

In the formula above the—line between $R_{13}$ and $R_{15}$ signify that a covalent bond may or may not be present. In other words, the compound of the present invention must contain 1 bridge connecting $R_{11}$ and $R_{17}$ and optionally may contain a second bridge between $R_{13}$ and $R_{15}$.

As indicated hereinabove, $AA_1$ and $AA_{15}$ are bridged by the group $R_1$-$R_2$-$R_5$-$R_7$ and $AA_3$ and $AA_{11}$, when bridged, are connected by the group $R_3$-$R_4$-$R_6$-$R_5$, respectively.

Figure 1:
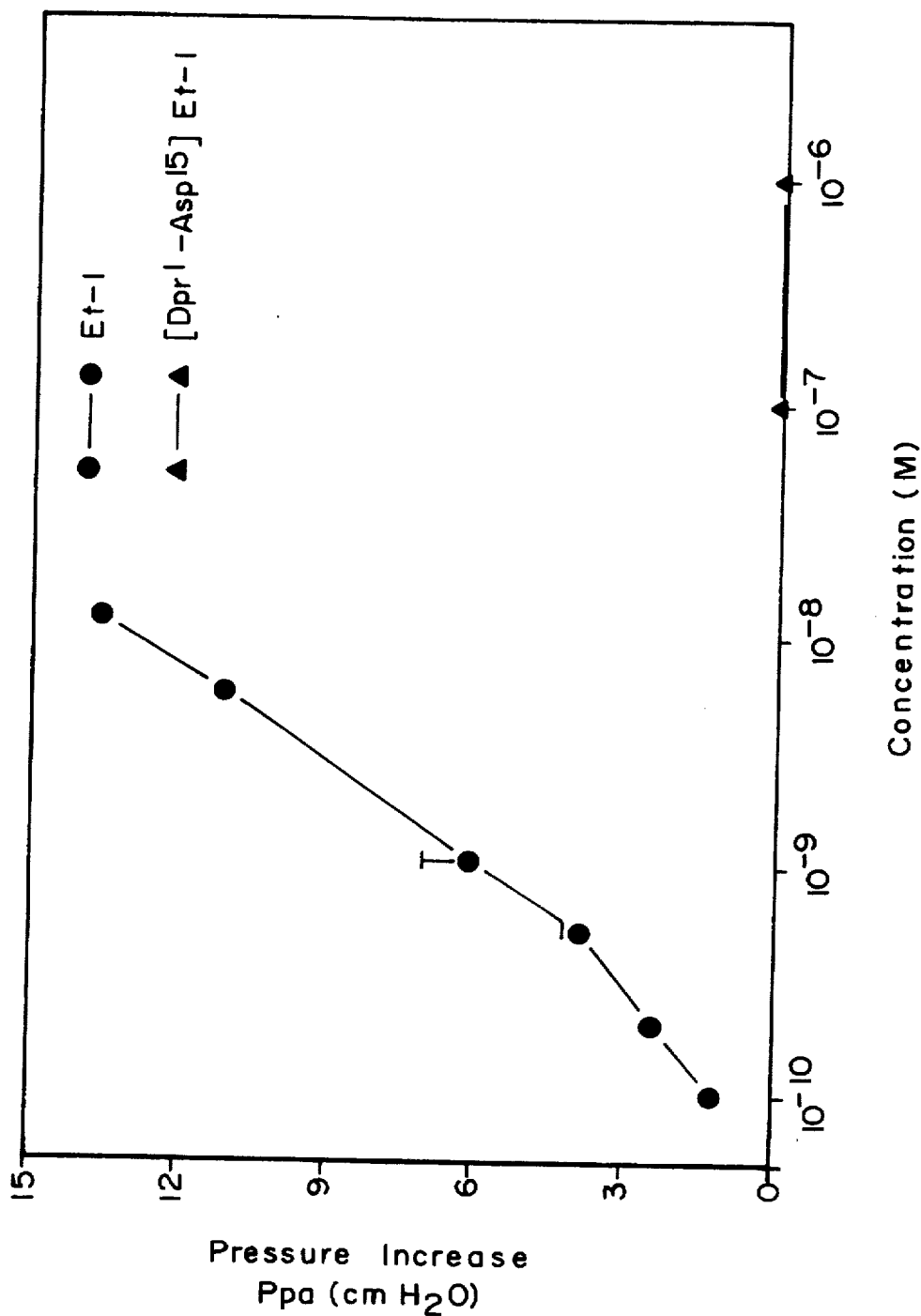
FIG 1 is a graph comparing the increase in pulmonary pressure for guinea pig lung perfused with Et-1 and $$[\overline{\text{Dpr}^1 - \text{Asp}^{15}}]\text{Et-1}$$

at concentrations ranging from $10^{-10}$ to $10^{-6}$ M.

DETAILED DESCRIPTION OF THE INVENTION

As can readily be seen from the FORMULA 1, the bridge forming between $R_{11}$ and $R_{17}$ consists of a bond between $AA_1$ and $AA_{15}$. Similarly, if a second bridge is present, the bridge is formed between $R_{13}$ and $R_{15}$. Substituting these values into Formula I, it becomes $$\begin{array}{c} \text{IA} \end{array}$$

$$\begin{array}{c}
\phantom{R_{14}}\begin{array}{ccccc}
\text{H} & \text{H} & & \text{H} & \\
| & | & & | & \\
\text{C}-\text{C}-\text{N}-R_{12}-\text{C}-(\text{CH}_2)_{\overline{m}} & \text{C}-(\text{CH}_2)_n-R_9-R_{10} \\
\| & | & \| & | & \\
\text{O} & R_3 & \text{O} & R_1 & \\
& | & & | & \\
& R_4 & & R_2 & \\
R_{14}\phantom{XX}& | & & | & \\
& R_6 & & R_8 & \\
& | & & | & \\
\text{H} & R_5 & \text{O} & \text{H} & R_7 \\
| & | & \| & | & | \\
\text{N}-\text{CH}-\text{C}-R_{16}- & \text{N}-\text{CH}-\text{C}-R_{18} \\
& & & & \| \\
& & & & \text{O}
\end{array}
\end{array}$$

In this formula, $R_{10}$, $R_9$, $R_{12}$, $R_{14}$, $R_{16}$, $R_{18}$, $R_1$, $R_2$, $R_8$, $R_7$, $R_3$, $R_4$, $R_6$, $R_5$, m and n are defined heretofore. The moiety $$\begin{array}{c}
\text{H} \\
| \\
-\text{C}-(\text{CH}_2)\text{m}-\text{C}-(\text{CH}_2)\text{n}-R_9 \\
\| \phantom{XXXXX} | \\
\text{O} \phantom{XXXXX} R_1 \\
\phantom{XXXXXX} | \\
\phantom{XXXXXX} R_2
\end{array}$$

which is $AA_1$ can be thought of as one residue and $$\begin{array}{c}
R_8 \\
| \\
R_7 \\
\text{H} \phantom{X}| \\
\text{N}-\text{CH}-\text{C}- \\
\phantom{XXXXX}\| \\
\phantom{XXXXX}\text{O}
\end{array}$$

is $AA_{15}$ can be thought of as another residue, which are joined together by the bond between $R_8$ and $R_2$. Although $R_8$ and $R_2$ may independently be $$\begin{array}{cc}
-\text{C}-, & \text{N}, \\
\| & | \\
\text{O} & \text{H}
\end{array}$$

—O—, or S, and theoretically all combinations and permutations are possible as long as the combinations yield a bond which is stable at physiological pH (for example, $R_8$ and $R_2$ do not form O—O,

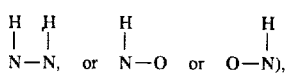

it is preferred that $R_2$–$R_8$ have only certain values, i.e.,

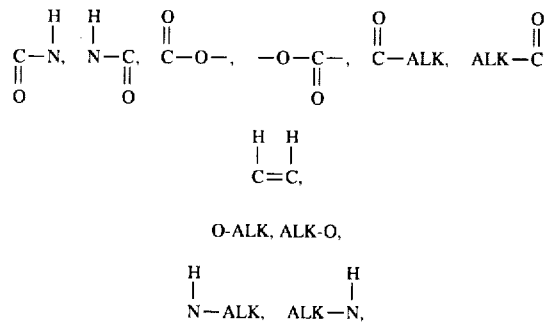

O-ALK, ALK-O, $$\begin{array}{cc} H & H \\ | & | \\ N-ALK, & ALK-N, \end{array}$$

ALK-S, S-ALK,

ALK, wherein ALK is as defined above. Based on the definitions of $R_1$, $R_2$, $R_8$ and $R_7$, this bridge may have as little as 1 atom or as many as 11 atoms in the principal chain linking $R_{11}$ with $R_{17}$. The preferred values of ALK are $CH_2$ or $CH_2CH_2$.

Similarly $R_{13}$ and $R_{15}$ when joined together are linked by a covalent bond between $R_4$ and $R_6$. The descriptions in the previous paragraph are equally applicable to the linkage between $R_4$ and $R_6$. Again, the $R_4$–$R_6$ linkage is preferred to have the values enumerated above. Thus, this second linkage may contain as little as 1 atom or as many as 11 atoms in the principal chain linking $R_{13}$ and $R_{15}$. Again, the preferred values of ALK are $CH_2$ or $CH_2CH_2$.

Consequently, the compounds of the present invention may contain only 1 bridge connecting $R_{11}$ with $R_{17}$ (or $AA_1$ with $AA_{15}$), or it may contain two bridges, i.e., $R_{11}$ with $R_{17}$ and $R_{13}$ with $R_{15}$. The former bridge must always be present; it is not necessary for the latter bridge to be present. However, the present invention excludes those compounds containing two disulfide bridges. But, the present invention contemplate compounds in which at most one disulfide bond is present, and when present, it may be in the inner bridge.

As used herein the term "amino acid residue" refers to that portion of an amino acid in which the amino hydrogen and the hydroxy from the carboxy group is absent as, for example, when said amino acid is condensed with other amino acids through peptide bonds. Likewise, the term "peptide residue" consists of two or more amino acid residues in a peptide chain in which the N-terminal hydrogen and the C-terminal hydroxyl are absent. It is preferred that the amino acid is an α or β-amino acid, most preferentially an alpha amino acid. It is also preferred that the amino acid be a naturally occurring amino acid and most preferentially one of the 20 naturally occurring amino acids which are listed in the following table along with their common abbreviations:

| ABBREVIATIONS OF COMMON AMINO ACIDS | | |
|---|---|---|
| | 3 Letter | 1 Letter |
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threorline | Thr | T |
| Tryptophan | Trp | W |
| Tyrosine | Tyr | Y |
| Valine | Val | V |

In addition, the term amino acids also include such amino acids as homoserine (Hse), and naphthylalanine (Nal). Further, the term "amino acid" also encompasses diamino lower alkanoic acid and amino lower alkyl dicarboxylic acid.

As used herein, the term lower alkyl, when used alone or in combination, is an alkyl group containing up to 6 carbon atoms. The alkyl group may be straight chained or branched. It includes such groups as methyl, ethyl, propyl, isopropyl, butyl, sec-butyl, isobutyl, t-butyl, amyl and the like. The preferred alkyl group is methyl.

Unless defined differently, as used herein, alkylene When used alone or in combination is an alkylene chain containing up to a total of six carbon atoms. The alkylene chain may be a straight-chained or branched and includes such groups as methylene, ethylene, propylene, isopropylene, butylene, isobutylene and the like.

Aryl, when used alone or in combination, refers to an aromatic hydrocarbon containing 6 to 10 ring carbon atoms and up to a total of 14 carbon atoms. Said term includes such groups as phenyl, tolyl, α and β-naphthyl and the like.

Lower cycloalkyl, when used alone or in combination with other terms, is a cycloalkyl group containing 5- or 6-ring carbon atoms and up to a total of 10 carbon atoms. Examples include cyclopentyl, cyclohexyl and the like.

Lower alkanoic acid, when used alone or in combination is a lower alkyl group substituted with a carboxy (COOH).

ALK as used herein, is preferably $CH_2$ or $CH_2CH_2$. Therefore, preferred ALK-S and S-ALK are $CH_2S$, $SCH_2$, $CH_2CH_2S$ and $S-CH_2CH_2$. The most preferred S-ALK and ALK-S are $SCH_2$, and $CH_2S$, respectively.

Diamino lower alkanoic acid as used herein is a lower alkanoic acid containing two amino groups. It is preferred that the one of the amino groups is substituted on the α-carbon. The second amino group may be substituted on any of the carbons in the alkylene chain, although it is preferred that it be substituted on the β-carbon or the omega carbon. It is especially preferred that the diamino lower alkanoic acid is an α,β-diaminoalkanoic acid. Examples include 2, 3-diaminopropionic acid, lysine and the like.

Amino lower alkyl dicarboxylic acid is a lower alkyl amine containing two carboxy groups. It is preferred that the amino group is substituted on the α carbon to one of the carboxy groups. The second carboxy group is preferably substituted on the omega carbon of the alkylene chain. Examples include aspartic acid, glutamic acid and the like.

The amino acids of the present invention can be classified into various groups. One group classflies the amino acids with non-polar or hydrophobic side chains, and includes such amino acids as alanine, valine, glycine, leucine, isoleucine, proline, methionine and the like. Another group classifies the amino acids with an aromatic side chain, such as phenylalanine, naphthylalanine, tryptophan, tyrosine and the like. A third group consists of amino acids having uncharged polar side chains and includes serine, threonine, homoserine, cysteine, asparagine, glutamine and the like. A fourth group consists of acidic amino acids and includes aspartic acid, glutamic acid and the amino lower alkyl dicarboxcyclic acid and the like. A final group classifies the basic amino acids and includes lysine, arginine, histidine, the diamino lower alkanoic acids and the like. Modifications of the amino acid residues in compounds of the present invention are possible, subject to the caveats recited hereinabove. These modifications arise when one amino acid in the polypeptide is substituted for another. It is preferred that the amino acids listed in any one class be substituted with another amino acid in the same class. All of these modifications are contemplated to be within the scope of the present invention.

The term "percent homology" is the optimized value of the percent identity (matching score) between a compound of the present invention and any one of the key amino acid sequences, viz., Et-1, Et-2, Et-3, SA, SB or SC. It is determined by calculating the overlapping peptide sequences using the homology search algorithim originally developed by Lipman, et al. (*Science*, (1987) 227: 1435) (hereinafter "Lipman, et al.") as set forth in the CD-ROM Genetic Sequence Database System Reference Manual (Hitachi America, Ltd., Software Sales and Support Dept., 950 Elm Avenue, San Bruno, Calif. 94066, U.S.A. ) (hereinafter "Manual"). Both Lipman, et al. and the Manual are incorporated by reference as if fully set forth herein.

As used herein, the term "endothelin active polypeptide" refers to a polypeptide containing from 16 to 26 amino acid residues having an outer disulfide bridge, and optionally having an inner disulfide bridge. Furthermore, they exhibit vasoconstrictor or vasopressor activity or any other property normally associated with endothelins.

Various assays for determining muscle contraction attributable to endothelin activity have been described. These tests perform the measurements using various preparations such as rat thoracic aorta, guinea pigileum, human urinary bladder, human renal artery, rat isolated perfused mesentery and aorta, guinea pig bronchus, porcine coronary artery strips and guinea pig lung and the like (Maggi, et al. *Eur. J. Phar.*, 174:23–31 (1989); Kitazumi, et al., *FEBS Letters*, 260: No. 2, 269–72 (1990); Rovero, et al. *Br. J. Pharmacol.*, 101: 232–4 (1990); Kimura, et al., *Biochem. Biophys. Res. Commun.*, 156:No. 3, 1182–6 (1988); Topouzis, et al., *Br. J. Pharmacol.*, 98: 669–77 (1989 ); Moon, et al., *Proc. Natl. Acad. Sci. USA*, 86, 9529–33 (1989); Randall, et al., *Br. J. Pharmacol.*, 98:685–99 (1989).

Still other tests for measuring the activity of endothelin-active polypeptides rely on determination of their vasopressor activity in rats (Kitazumi, et al., *FEBS Letters*, 260: No. 2, 269–72 (1990); Nakajima, et al., *Biochem. Biophys. Res. Commun.* , 163: No. 1, 424–9 (1989)).

A third category of test employs competitive receptor binding studies of endothelin-active polypeptides wherein the action of the polypeptide in displacing or inhibiting endothelins or sarafotoxins labelled with $^{125}I$ bound to different cells or tissues is determined. Thus, receptor binding studies are described using cultured rat vascular smooth muscle cells (Hirata, et al., *Biochem. Biophys. Res. Commun.* 160:No. 1, 228–34 (1989)), Swiss 3T3 cells (Fabregat, et al., *J. Cellular Physiol*, 145:88–94 (1990)), microsomal fractions from porcine thoracic aorta (Takasaki, et al., *Biochem. International*, 21:No. 6, 1059–64 (1990)), and rat cerebellar homogenates (Hiley, et al., *Br. J. Pharmacol.* 101: 319–214 (1990)).

The compounds of the present invention are endothelin antagonists, i.e., they inhibit the activity of endothelin active polypeptides. The term "endothelin antagonist" as used herein refers to a polypeptide with up to 26 amino acid residues having a percent homology of at least 40% as calculated above when compared to Et-1, Et-2, Et-3, SA, SB or SC. The endothelin antagonists display endothelin. blocking or antagonist activity as determined by commonly used testing procedures, such as by comparing the endothelin activity in the presence and absence of the antagonists in the assays described above. Exemplary of such test procedures are the assays discussed below.

Aortic Strip Contraction: This assay may be classified as contraction of helical strips of guinea pig or rat aorta (Bruner, C. A., et al , *Am. J. Physiol* 251 H1276-H1282 (1986); Brunet, C. A. , et al., *Hypertension* 11, 668–673 (1988)). For vascular reactivity studies, rat or guinea pigs are killed with an injection of pentobarbital and the thoracic aorta removed and placed in cold physiological bicarbonate buffer. Arteries are cleaned of excess fat and connective tissue and cut into helical strips. Vascular strips are mounted on metal tissue holders and placed in 50 ml tissue-baths filled with warmed (37° C.), aerated (95% $O_2$, 5% $CO_2$, pH 7.4) buffer. The upper end of each strip is connected to a force transducer (Grass FTO3) for measurement of isometric force, which is recorded on a Grass polygraph. Strips are allowed to equilibrate for 90 minutes under a constant passive force of 1.5 g, and are then exposed to synthetic peptides. Peptides are added cumulatively to the tissue bath in half-log concentration increments. Isometric tension generated is guantitated as mg force/$mm^2$. The magnitude of contractions obtained with endothelin and active polypeptide in the presence and absence of endothelin antagonists are compared with that in response to maximal depolarization (100 mM KCl) and to the maximal concentrations of norepinephrine ($10^{-6}$ M).

Concentration-response curves for endothelin-active peptides are analyzed using probit transformation to determine $ED_{50}$ values. A preferred $ED_{50}$ for the antagonists of the present invention is $10^{-12}$-$10^{-6}$M, and more preferably $10^{-10}$ to $10^{-8}$M. Potency of various analogs are compared using analysis of variance of the -log $ED_{50}$ values. Potency of various analogs may be compared using analysis of variance of the -log $ED_{50}$ values.

Competitive Binding

Endothelin active antagonists are also tested by determining their ability to compete with endothelin for receptor binding. Initially, it may be determined if a high concentration ($10^{-6}$ M) of the antagonist will shift the endothelin concentration-response curve in a competitive (parallel rightward shift) or non-competitive (decreased slope and maximum response) manner. If the antagonist appears to be a competitive antagonist for endothelin, Schild analysis may be employed to determine a pA2 value for the antagonist (which is an index of receptor affinity) (Arunlakshana, O., et al., *Brit. J. Pharmacol.* 14, 48–58 (1959) ).

In a typical procedure, mammalian (e.g., porcine, rat, guinea pig) vascular smooth muscle cells are grown 48 hours on a glass coverslip in Hanks minimal essential salts medium supplemented with 20% fetal bovine serum after which the medium is replaced with serumless medium. The latter is removed by aspiration and 1 ml of Kreb's Ringer's bicarbonate buffer containing 0.5% bovine serum albumin and 0.2 mM sodium azide is added. Endothelin or antagonist is added (up to $10^{-6}$M) and binding is allowed to occur over 45 min. at 4° C. in the presence of 1μM $^{125}$I-endothelin. The supernatant containing excess endothelin or antagonist is removed and the, cells washed three times with ice cold buffer. The residual cell associated radioactivity is determined with a gamma ray counter.

Isolated, Perfused Guinea Pig Lung: Another procedure for determining the vasoconstrictor action of the endothelin-active peptides and the blocking action of endothelin antagonists utilizes isolated, perfused guinea pig lung as described in more detail in Example 4, infra.

The present invention also includes precursors of endothelin antagonists which are polypeptides capable of being cleaved by chemical means, such as acidic or basic hydrolysis or by enzymatic means, such as endothelin cleaving enzyme to yield active endothelin antagonist of the present invention. The preferred antagonist precursors have the same structure as the antagonists depicted in Formula I except that they contain a peptide extension at either the C-terminus or N-terminus or both with up to 80 and preferably up to 30 and most preferably, from 10 to 20 amino acid residues appended to the polypeptides. Various peptide extensions are known in the art, e.g., Ma or Po discussed hereinbelow. Other peptide extensions at the C-terminus or N-terminus or both are also known. For example, EPO Applications 366 016 add 315 118 both to Masaki disclose various N-terminal and C-terminal peptide extensions e.g., His Ala Gln Gly Thr His Leu Arg Leu Arg Arg Cys Ser; Glu Gly Ala Pro Glu His His Arg Set Arg Arg; Met Asp Tyr Phe Pro Met Ile Ile Ala Leu Leu Phe Val Ala Phe Gln Gly Ala Pro Glu Thr Ala Val Leu Gly Ala Glu Leu Set Pro Glu Ala Glu Ser Gln Gly Glu Thr Pro Ser Pro His Ala Set Trp Arg Pro Arg Arg Ser Lys Arg, at the N-terminus, and at the C-terminus, Val Asn Thr Pro Glu His Ile Val Pro Tyr Gly Leu Gly Ser Pro Ser Arg Ser Arg Arg Ser Leu Lys Asp Leu Phe Pro Val Asn Thr Pro Glu; and Ile Ash Thr Pro Glu. The teachings in both EPO applications are incorporated by reference as if fully set forth herein. It is preferred that the C-terminus amino acid $R_{18}$ is Trp and that a valine residue is at the N-terminus of the peptide extension, appended to $R_{18}$ through a peptide bond. It is preferred that the peptide extension comprise an amino acid sequence that ensures that the precursor has adequate water solubility (i.e., solubility greater than about $10^{-6}$ M).

The preferred peptide extension attached to the C-terminus of $R_{18}$ has the amino sequence of Val-Asn-Thr-Pro-Glu-His-Val-Val-Pro-Tyr-Gly-Leu-Gly-Ser-Pro-Arg-Ser (hereinafter identified as Ma) or Val-Asn-Thr-Pro-Glu-His-Ile-Val-Pro-Tyr-Gly-Leu-Gly-Ser-Pro-Ser-Arg-Ser (hereinafter identified as Po). In shorthand notation, if Ma or Po are appended to a endothelin active polypeptide or antagonist, it is identified as -Ma or -Po. For example, if Ma is appended to Et-1, it is designated at. Et-1-Ma, meaning that the polypeptide is an Et-1 polypeptide joined together with a Ma polypeptide by a peptide linkage at the C-terminus amino acid of Et-1 and N-terminus amino acid of Ma. Similarly, Et-2-Po means that the N-terminus of Po polypeptide is appended to the Et-2 molecule at the C-terminal end of Et-2, and so on.

It is preferred that the endothelin antagonists of the present invention have at least 40% and preferably at least 50% homology to Et-1, Et-2 Et-3, SB, SA or SC. It is more preferred that the end othelin antagonists of the present invention have at least 60% or most preferably 90% homology with Et-1, Et-2, Et-3, SB, SA or SC.

In a preferred embodiment, the endothelin antagonists of the present invention have an extremely high degree of homology relative to the endothelin active polypeptides for which they are specific antagonists ranging from 87.5% to 96.4% when calculated by standard methods for determining percent identity of homopolymers as hereinafter defined. In spite of the remarkable similarity in size, shape, and chemical composition of the compounds of the present invention to their counterpart endothelin active polypeptides, it has been further surprisingly discovered that the compounds of the present invention exhibit antagonist activity and are effective antagonists even at concentrations substantially higher than those at which their endothelin analogs show maximin activity.

In the formula hereinabove, it is preferred that $R_1$ $R_3$, $R_5$ and $R_7$ are each independently a chemical bond or substituted or unsubstituted alkylene. If any one of $R_1$, $R_3$, $R_5$ and $R_7$ are alkylene, it is preferred that the alkylene chain is unsubstituted.

The preferred values of $R_2$ and $R_8$ taken together are

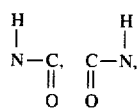

methylene or ethylene A more preferred embodiment is

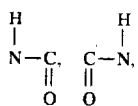

methylene, ethylene, ALK-S or S-ALK. An even more preferred embodiment of $R_2$ and $R_8$ taken together is

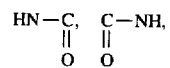

methylene, or ethylene. The most preferred embodiment of $R_2$-$R_8$ are

and especially

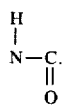

It is preferred that $R_1$-$R_2$-$R_8$-RV is

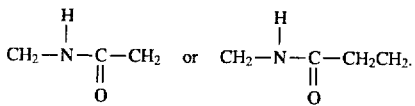

When $R_{13}$ and $R_{15}$ do not form a second bridge, the preferred values of $R_{13}$ and $R_{15}$ are Ala, Gly, Thr, homoserine and especially Ser. The most preferred is Threonine, homoserine and especially Serine. On the other hand, when $R_{13}$ and $R_{15}$ do form a second bridge, then $R_4$ and $R_6$ are covalently bonded to each other. In this case, it is preferred that $R_3$ and $R_5$ are substituted or unsubstituted alkylene or are a chemical bond and $R_4$-$R_6$ taken together is S—S

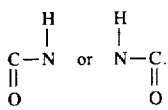

In this case, the most preferred value of $R_3$ and $R_5$ is $CH_2$ and $R_4$–$R_6$ is S—S. In the most preferred embodiment, $R_{13}$–$R_{15}$ is cysline.

In the formula hereinabove, it is preferred that $AA_1$ is an diamino lower alkanoic acid. It is especially preferred that $AA_1$ is an α,β diamino lower alkanoic acid. Finally, the most preferred $AA_1$ is 2, 3-diaminopropionic acid. Lysine is also a preferred value of $AA_1$.

The preferred value of $AA_{15}$ is an amino dicarboxylic acid, especially where one of the amino groups is substituted on the α carbon to the carboxy group. The most preferred $AA_{15}$ is aspatic acid and glutamic acid.

The most preferred values of $AA_3$ and $AA_{11}$ is cystine.

In a preferred embodiment, the compounds of the present invention contain 21 amino acid residues. In this embodiment, the compounds of the present invention have at east 40% homology to an endothelin active polypeptide selected from the group consisting of Et-1, Et-2, Et-3, SA, SB and SC and have the formula:

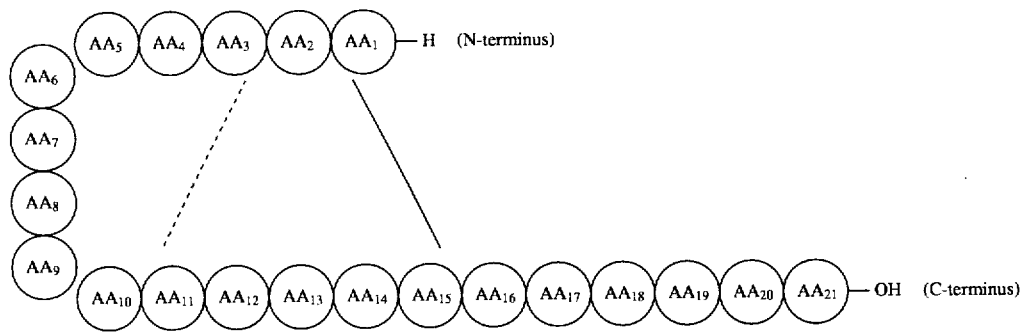

II wherein $AA_1$, $AA_3$, $AA_{11}$ and $AA_{15}$ have been defined as hereinabove and $AA_2$, $AA_4$–$AA_{10}$, $AA_{12}$–$AA_{14}$ and $AA_{16}$-$AA_{21}$ are independently amino acid residues. It is preferred that these amino acid residues are α amino acids and more preferably are independently the twenty naturally occurring amino acids, Nal or Hse.

In the formula hereinabove, the preferred values of $R_1$, $R_2$, $R_3$, $R_4$, $R_5$, $R_6$, $R_7$ and $R_8$ are discussed hereinabove.

It is preferred that: $AA_2$ is Ser, Thr, Hse, Tyr, Cys, Ash or Gln. Especially preferred values of $AA_2$ is Ser, Thr or Hse. The most preferred $AA_2$ is Ser or Thr.

It is preferred that $AA_4$ is Ser, Thr, Hse, Tyr, Cys, Asn , Gln, Phe naphthylalanine (Nal), Ala, Val, Gly, Leu, Ile, Met, Pro, Trp, Lys, Arg or His. Especially preferred values of $AA_4$ is Set, Thr, Phe, Lys or Ala, Thr, Val, Leu or Ile. The most preferred $AA_4$ is Ser, Thr, Phe and Lys.

The preferred $AA_5$ is Ser, Thr, homoserinyl, Cys, Tyr, Asn, Gln, Ala, Val, Glu, Leu, Ile, Pro, Phe, Trp, Met, Asp or Glu. Especially preferred is Ala, Ser, Thr, Val, Ile, Leu, Hse, Asp or Glu. The most preferred value of $AA_5$ is Asp, Ser, and Thr.

$AA_6$ is preferably Gly, Leu, Val, Ala, Ile, Pro, Phe, Nal, Trp, Met, Tyl, Set, Thr, homoserinyl, Cys, Asn or Gln. It is preferred that $AA_6$ is Gly, Leu, Ile, Val, Ala, Gly, Trp, and Met. Most preferably, $AA_6$ is Leu, Trp, Tyr, Phe, Met, Hse or Gly. The especially most preferred value of $AA_6$ is Leu, Trp, Tyr or Met.

$AA_7$ is preferably Met, Leu, Val, Ala, Ile, Gly, Pro, Phe, Nal, Trp, Met, Met. [0], Ser, homoserinyl, Lys, Cys, Asn, Gln, Lys, Arg or His. Especially preferred is Met, Leu, Ile, Gln, Lys, Arg or His. Especially preferred is Met, Leu, Ile, Lys, Set, or Thr. Most preferred is Met, Leu, Lys, Thr, Ser or Hse. Especially most preferred is Met, Leu, Lys or Thr.

The preferred value of $AA_8$ is Asp, Glu, Asn, or Gln. Especially preferred is Asp or Glu. The most preferred is Asp.

The preferred values of $AA_9$ is Asp, Glu, Lys, Arg, His, Leu, Ile, Val, Ala, Pro, Phe, Nal, Trp, or Met. The especially preferred value of $AA_9$ is Lys, Glu, Asp, Leu or Ile, Val or Ala. The most preferred $AA_9$ is Asp and most preferably Lys or Glu.

$AA_{10}$ is preferably Asp or especially Glu.

$AA_{12}$ is preferably Val, Ala, Gly, Leu, Ile, Pro, Phe, Nal, Trp or Met, but is most preferably Val, Ala, Leu Ile. Especially preferred is Val, Leu, Ile or Ala. Most especially preferred is Val or Leu.

$AA_{13}$ is preferably Ser, Thr, homoserinyl, Cys, Tyr,, Trp, Phe, Nal, Asn and. Gln, but most preferably Tyr, Asn, Phe or Gln. Most especially preferred is Tyr or Asn.

$AA_{14}$ is preferably Tyr, Phe, Nal, Trp, Ala, Val, Gly, Leu, Ile, Pro, Met, Set, Thr, homoserinyl, Cys, Asn or Gln. It is most preferably Trp, and especially, Tyr, Nal or Phe. Most especially, it is Phe or Tyr.

$AA_{16}$ is preferably His, Lys or Arg, and most preferably His.

$AA_{17}$ is preferably Gln, Asn, Tyr, Cys, Ser, Thr and homoserinyl, Ala, Val, Gly, Leu, Ile, Pro, Phe, Nal, Trp and Met. However, it is especially preferred that $AA_{17}$ is Gln, Ash, Leu, Ile, Val, or Ala. The most preferred $AA_{17}$ is Leu and Gln.

$AA_{18}$ is preferably Glu and especially Asp.

$AA_{19}$ is preferably Ala, Gly, Val, Leu, Ile, Pro Phe, Nal, Trp and Met. Especially preferred value of $AA_{19}$ is Ala, Val, Leu and Ile, with Val and Ile as the most preferred.

$AA_{20}$ is preferably Ala, Gly, Val, Leu, Ile, Pro, Phe, Nal, Trp and Met. Especially preferred is Ala, Val, Leu and Ile. Most especially preferred is Leu and Ile. The most preferred is Ile.

$AA_{21}$ is preferably Ala, Val, Gly, Leu, Ile, Pro, Phe, Nal, Trp and Met, Tyr, Set, Thr, homoserinyl, Cys, Asn and Glu. It is especially preferred that $AA_{21}$ is Trp or Tyr, Phe, Nal or Try and most preferably Trp.

A preferred first embodiment of the present invention is a polypeptide of Formula II having at least 40% homology to endothelin active polypeptide, wherein:

One of $AA_1$ and $AA_{15}$ is a diamino lower alkanoic acid and the other is an amino dicarboxylic acid;

$AA_2$ is Ser, Thr or homoserine;

$AA_3$ and $A_{11}$ are Cys;

$AA_4$ is Ser, Thr, homoserine, Phe, Tyr or Ala;

$AA_5$ is Ala, Ser, Thr, homoserine, Asp or Glu;

$AA_6$ is Gly, Leu, Val, Ile, Ala, Trp, Tyr or Met;

$AA_7$ is Met, Met [O], Leu, Ile, Val, Ala, Lys, Ser, Thr, and homoserine;

$AA_8$ is Asp or Glu;

$AA_9$ is Asp, Glu or Lys;

$AA_{10}$ is Asp or Glu;

$AA_{12}$ is Val, Ala, Gly, Leu, Ile or Pro;

$AA_{13}$ is Tyr, Asn or Gln;

$AA_{14}$ is Tyr, Phe or Trp;

$AA_{16}$ is His, Lys or Arg;

$AA_{17}$ is Gln, Asn, Leu, Ile, Val or Ala;

$AA_{18}$ is Glu or Asp;

$AA_{19}$ and $AA_{20}$ are independently Ala, Val, Gly, Leu or Ile; and $AA_{21}$ is Tyr or Trp or Phe.

In the above embodiment, it is especially preferred that one of $AA_1$ and $AA_{15}$ is an α, β-diamino lower alkanoic acid. Finally, it is most preferred that one of $AA_1$ and $AA_{15}$ is 2, 3-diamino propionic acid (Dpr) and the other is Asp or Glu.

It is the most especially preferred that $AA_1$ is Dpr and $AA_{15}$ is Asp or Glu.

A more preferred second embodiment of the present invention is wherein $AA_1$ is Dpr, $AA_{15}$ is Glu or Asp, and $AA_2$, $AA_4$-$AA_{10}$, $AA_{12}$-$AA_{14}$ and $AA_{16}$-$AA_{21}$ is as defined in the preferred first embodiment described hereinabove.

More preferred embodiments includes $AA_2$ is Ser, $AA_4$ is Ser, $AA_5$ is Ser, $AA_6$ is Leu, $AA_7$ is Met, $AA_8$ is Asp, $AA_9$ is Lys, $AA_{10}$ is Glu, $AA_{11}$ is Cys, $AA_{12}$ is Val, $AA_{13}$ is Tyr, $AA_{14}$ is Phe, $AA_{16}$ is His, $AA_{17}$ is Leu, $AA_{18}$ is Asp, $AA_{19}$ is Ile, $AA_{20}$ is Ile, and $AA_{21}$ is Trp;

$AA_2$ is Ser, $AA_4$ is Ser, $AA_5$ is Ser, $AA_6$ is Trp, $AA_7$ is Leu, $AA_8$ is Asp, $AA_9$ is Lys, $AA_{10}$ is Glu, $AA_{12}$ is Val, $AA_{13}$ is Tyr, $AA_{14}$ is Phe, $AA_{16}$ is His, $AA_{17}$ is Leu, $AA_{18}$ is Asp, $AA_{19}$ is Ile, $AA_{20}$ is Ile,, and $AA_{21}$ is Trp;

$AA_2$ is Thr $AA_4$ is Phe, $AA_5$ is Thr, $AA_6$ is Tyr, $AA_7$ is Lys, $AA_8$ is Asp, $AA_9$ is Lys, $AA_{10}$ is Glu, $AA_{12}$ is Val, $AA_{13}$ is Tyr, $AA_{14}$ is Tyr, $AA_{16}$ is His, $AA_{17}$ is Leu, $AA_{18}$ is Asp, $AA_{19}$ is Ile, $AA_{20}$ is Ile, and $AA_{21}$ is Trp;

$AA_2$ is Ser, $AA_4$ is Lys, $AA_5$ is Asp, $AA_6$ is Met, $AA_7$ is Thr, $AA_8$ is Asp, $AA_9$ is Lys, $AA_{10}$ is Glu, $AA_{12}$ is Leu, $AA_{13}$ is Tyr, $AA_{14}$ is Phe, $AA_{16}$ is His, $AA_{17}$ is Gln, $AA_{18}$ is Asp, $AA_{19}$ is Val, $AA_{20}$ is Ile, and $AA_{21}$ is Trp;

$AA_2$ is Ser, $AA_4$ is Lys, $AA_5$ is Asp, $AA_6$ is Met, $AA_7$ is Thr, $AA_8$ is Asp, $AA_9$ is Lys, $AA_{10}$ is Glu, $AA_{12}$ is Leu, $AA_{13}$ is Asn, $AA_{14}$ is Phe, $AA_{16}$ is His, $AA_{17}$ is Gln, $AA_{18}$ is Asp, $AA_{19}$ is Val, $AA_{20}$ is Ile, and $AA_{21}$ is Trp; or $AA_2$ is Ser, $AA_4$ is Lys, $AA_5$ is Asp, $AA_6$ is Met, $AA_7$ is Thr, $AA_8$ is Asp, $AA_9$ is Glu, $AA_{10}$ is Glu, $AA_{12}$ is Leu, $AA_{13}$ is Asn, $AA_{14}$ is Phe, $AA_{16}$ is His, $AA_{17}$ is Gln, $AA_{18}$ is Asp, $AA_{19}$ is Val, $AA_{20}$ is Ile, and $AA_{21}$ is Trp;

and, in each case $AA_1$, $AA_3$, $AA_{11}$ and $AA_{15}$ are as defined hereinabove.

The most preferred embodiment is wherein $AA_1$ is Dpr;

$AA_2$ is Ser or Thr;

$AA_3$ and $AA_1$ are Cys;

$AA_4$ is Ser, Thr, Phe or Lys;

$AA_5$ is Asp, Ser or Thr;

$AA_6$ is Leu, Trp, Tyr or Met;

$AA_7$ is Met, Leu, Lys or Thr;

$AA_8$ is Asp;

$AA_9$ is Lys or Glu;

$AA_{10}$ is Glu;

$AA_{12}$ is Val or Leu;

$AA_{13}$ is Tyr or Asn;

$AA_{14}$ is Phe or Tyr;

$AA_{16}$ is His;

$AA_{17}$ is Leu or Gln;

$AA_{18}$ is Asp;

$AA_{19}$ is Ile or Val.;

$AA_{20}$ is Ile; and $AA_{21}$ is Trp.

Preferred species of the present invention are

[Dpr¹, Asp¹⁵] Et-1, [Dpr¹, Glu¹⁵] Et-1,

[Dpr¹, Asp¹⁵] Et-2, [Dpr¹, Glu¹⁵] Et-2,

[Dpr¹, Asp¹⁵] Et-3, [Dpr¹, Glu¹⁵] Et-3,

[Dpr¹, Asp¹⁵] SB, [Dpr¹, Glu¹⁵] SB,

[Dpr¹, Asp¹⁵] SA, [Dpr¹, Glu¹⁵] SA, and

[Dpr¹, Asp¹⁵] SC, [Dpr¹, Glu¹⁵] SC.

Considering the amount of homology between the polypeptides of the present invention and the endothelins, it is surprising that the compounds of the present invention exhibit antagonist activity in endothelin susceptible tissues. While we do not wish to be held to any theory regarding mechanism it is believed that the endothelin peptide binds to one or more specific receptors and thereafter interacts with the receptor through a disulfide exchange mechanism (prestoably involving the $Cys^{1-15}$ disulfide bridge atoms) initiating a vasoconstrictive or vasopressor response. Such disulfide exchange mechanism would be analogous to those shown in the insulin and IGF receptors (Morrison, et al., *J. Biol. Chem.* 1988, 7806–13; Wilden, et al. *Bio-Chemistry*, 1989, 28:9734–40). Since the polypeptides of the present invention do not contain a disulfide outer bridge, they are able to bind competitively or non-competitively and elicit no endothelin activity for lack of proper disulfide functionality.

The polypeptides of the present invention can be prepared by art recognized procedures. Conventional solid phase synthesis methods provide great flexibility with regard to choice of amino acid moieties which may be included in the sequence (naturally occurring amino acids do not have to be used) and with regard to choice of protecting groups for side chain functions. Moreover, they provide additional advantages with regard to the cyclization steps needed to form the inner and outer bridging structures. Generally, two schemes for forming peptides are preferred. 1. t-Boc Peptides that are not cyclic may be synthesized by standard tert-butyloxycarbonyl chemistry (tBoc) (Merrifield, R. B., *J. Am Chem Soc.* (1963) 75, 2149; Merrifield, R. B., *Adv. Enzymol.* 32, 221 (1969); Merrifield R. B. *Science* (1986) 232, 341–347) or fluorenylmethoxy-carbonyl (Fmoc) chemistry (Atherton, E., et al., *J. Biorgan Chem* (1979) 8, 351–370; Sheppard, R. C., *Chem. Brit.* (1983) 19, 402–414; Atherton E. et al., *J. Chem. Soc. Perkin I* (1981) 529–537). These techniques are known to one skilled in the art. tBoc synthesis may be performed using an automated peptide synthesizer, for example, the Biosearch Model 9500. The tBoc amino acid derivatives are the most cost-effective and are commercially available in pure form.

An exemplary scheme for the synthesis of peptides using tBoc chemistry is shown hereinbelow in Scheme 1.

SCHEME I

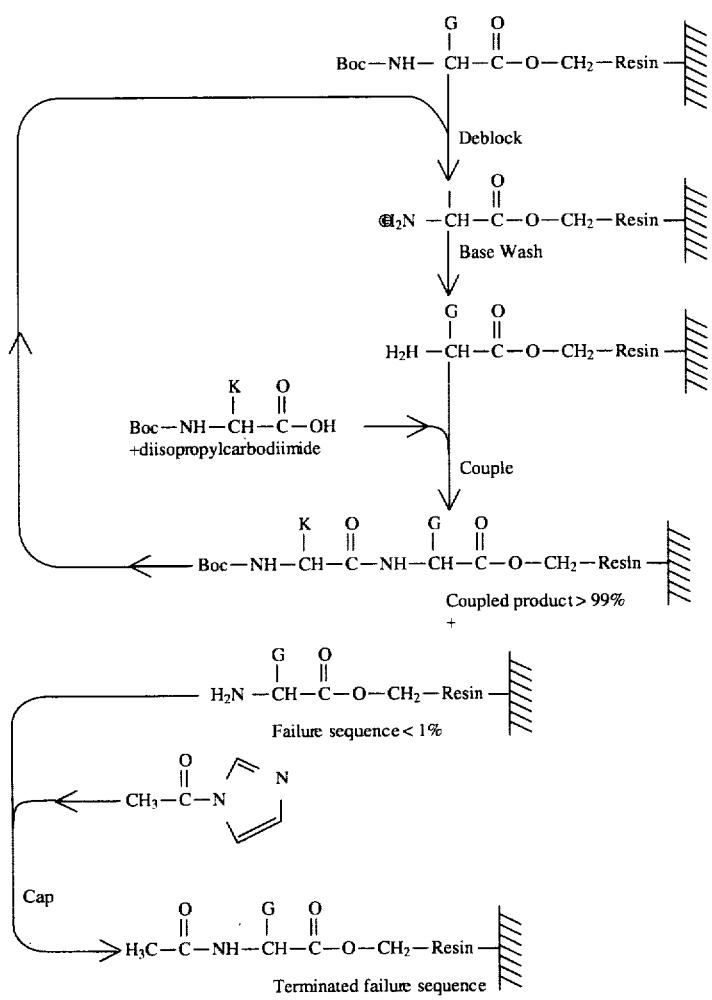

wherein G and K are side chains of the amino acids defined herein. The amino acid derivatives are blocked at the alpha amino group by a tert-butyloxycarbonyl (tBoc) group. Many blocking groups are used to protect the side chain functional groups of the amino acids, and these are known to one skilled in the art. But the most commonly used are the benzyl-based derivatives (for a general description of solid phase peptide synthesis and blocking groups, see Stewart J. M., et al and Young, J., *Solid Phase Peptide Synthesis 2nd Ed.* Pierce Chemical Co., Rockford Ill., (1984)) The C-terminal amino acid is coupled to a polystyrene-divinyl benzene resin and synthesis is performed out from the carboxy terminus to the amino terminus (see Merrifield, R. B., *Science,* op. cit.). Several resin types are available. Since endothelin is a 21 amino acid peptide with a free C-terminal, synthesis using the Merrifield resins gives optimal yields of the peptides of up to 30 amino acids and gives a peptide with a free C-terminal carboxyl group. It is most efficient to use the resin with the C-terminal amino acid already coupled (via a benzyl ester linkage) because this first coupling step is time consuming and the C-terminal amino acid resins are readily available. Upon completion of synthesis, acidolysis will cleave the ester leaving a free C-terminal carboxyl group. The preferred resin is the PAM (phenylacetamidomethyl) resin (Mitchell, A. R., et al *J. Org. Chem,* (1978) 43, 2845–2852), which has a linker which is more stable to acid than the benzyl ester linkage, thus eliminating the 1% loss of peptide during each tBoc deprotection step (see below) that results with the Merrifield resin. However, since the cleavage reaction gives low yields (as low as 70%), the PAM resins should be used only for peptides of 40 or more amino acids. The MBHA (methylbenzhydrylamine) resin is a third choice if the desired product is a peptide with an amide group on the C-terminus (Matsueda, C. R., et al., *Peptides,* 1981, 2, 45–50). This is often desired if the synthesized peptide is part of a longer polypeptide.

Synthesis occurs with the resin in a glass reaction vessel fitted at the bottom with a sintered glass disc to accommodate draining or mixing (via introduction of nitrogen gas) of the reaction mixture The various reagents for synthesis are added sequentially and are removed by filtration and washing. The addition of reagents occurs by positive pressure displacement of the reagents from their reservoirs to the reaction vessel and then nitrogen is used to mix the components in the reaction vessel. The addition of subsequent amino acids occurs by a repetitive protocol consisting of four steps. The first step is removal (deblocking) of the alpha amino protecting group using acid, e.g., 45% trifluoroacetic acid (TFA). The second step is a basewash using for example, diisopropylethylamine (DIPEA) to remove and neutralize the TFA used in the deblocking, and to insure that the now unprotected alpha amino group is unprotonated. The third step is the coupling reaction in which an amino acid with a tBoc protected alpha amino group is introduced into the reaction vessel along with the activator, such as diisopropylcarbodiimide (DIPCDI) or dicyclohexyl carbodimide. The fourth step is capping of any unreacted alpha amino groups so they are blocked from reaction in latter addition cycles. Acetyl imidazole (0.3 M) is preferably used since this reagent is a selective and powerful acylating reagent which blocks any unreacted alpha amino groups without side chain modification. Synthesis occurs by repeating this cycle for each amino acid added to the peptide.

Since the peptide-resin link is stable to 45% TFA (deblock solution), the peptide must be cleaved with strong acid. The cleavage of peptides synthesized by the tBoc approach from solid phase: resin is usually done by the hydrofluoric acid (HF) method (see Stewart, J. M. et al., *Solid Phase Peptide Synthesis*, op. cit.). Another standard procedure "low/high" HF method may also be used (Tam, J. P., et al., *Int. J. Peptide Protein Res.* 26, 262–273 (1985); Frank, B. H., et al., *Peptides: Synthesis-Structure Function* 729–738 (1981)). A Teflon-Kel-F apparatus is used to contain the HF during the acidolysis procedure. 10 ml of HF for every gram of resin is distilled into the reaction vessel where the cleavage is to take place HF cleavage is performed at 0° C. for 45 minutes This cleaves the peptide from the resin as well as removes all side chain blocking groups on the peptide. When side chain blocking groups are removed by acidolysis, reactive carbonium ions are formed which can easily alkylate methionine, cysteine, glutamic acid, tyrosine and tryptophan residues (Tam, J. P., et al., *Int. J. Peptide Protein Res.* op. cit.). These alkylations can be minimized by providing excess amounts of a nucleophile scavenger. One ml of anisole is added per gram of resin for this purpose. Thiol-containing scavengers such as thioanisol or thiocresol are used if methionine and cysteine are in the sequence. Alternatively, the two step "low-high" HF method can be used for peptides prone to side reactions. Most side chain groups can be cleaved at the first "low" step which involves a lower concentration of HF (diluted with dimethyl sulfide). However, the carbonium ions responsible for alkylation side reactions are not formed by this "low" method. The precursors of these carbonium ions are then removed before the "high" (neat HF) cleavage is performed. High HF treatment is required for the removal of the peptide from some resins as well as removing a few stable side chain protecting groups. Another method uses the Fmoc blocking group.

2. Fmoc Solid phase peptide synthesis using the Fmoc (fluorenylmethoxycarbonyl) protection scheme has gained wide acceptance in recent years because it circumvents many of the above mentioned problems encountered in the tBoc strategy. The Biosearch Model. 9500 automated peptide synthesizer can be adapted to perform Fmoc synthesis. Alternatively, Fmoc synthesis can also be performed on the manual-DuPont RAMPS system where small guantities of up to 25 peptides can be made simultaneously (*Ramps Manual* (1987) DuPont). Large scale synthesis will be performed on the automated synthesizer, while the manual system may be employed if a series of related analogs is to be made.

The Fmoc strategy employs an orthogonal system where the alpha amino protecting group is base-labile and the peptide-resin linkage is acid-labile. This offers a distinct advantage over Tboc strategy where the amino protecting group and the peptide-resin link are both acid-labile. Loss of peptide during deblocking steps is virtually eliminated in Fmoc synthesis (Bodanzsky, M., *Peptide Chemistry*, Springer-Berlag, Berlin Heidelberg (1988)). Moreover, cleavage and side chain deprotection can be performed under milder acid conditions and more labile resins and side chain protecting groups have been developed for this purpose (see Stewart, J. M. et al., *Solid Phase Peptide Synthesis*, op. cit.; Bodanzsky, M., *Peptide Chemistry*, op. cit.). This eliminates many of the side reactions that can occur with harsh HF treatment.

Like tBoc synthesis, Fmoc synthesis is from the carboxyl to the amino terminus. The amino acid derivatives are blocked at the alpha amino group by a fluorenylmethoxycarbonyl (Fmoc) group and the side chains are protected by t-butyl based groups. Since it is more desirable to synthesize endothelin antagonist peptides with a free carboxy terminus, a Wang (p-alkoxybenzyl alcohol) resin is preferred for most Fmoc syntheses. The Wang resin is available with the C-terminal amino acid already attached and, upon acid cleavage, results in a peptide with a free carboxyl terminus.

The addition of subsequent amino acids occurs by a repetitive protocol consisting of three steps. The first step is the deblocking of the alpha amino protecting group using a dilute (50%) solution of piperidine in dimethylformamide (DMF). This procedure results in a free alpha amino group that is unprotonated, thus obviating the need for a basewash step as in tBoc. The second step is the coupling reaction in which an amino acid with an Fmoc-protected alpha amino group is introduced. A number of coupling methods are possible, but the most preferred is the use of the activator BOP [(benzotriazolyloxy)tris(dimethyiamino)phosphonium hexa-fluorophosphate] in the presence of HOBt (1-hydroxybenzotriazole) to form the benzotriazolyl active ester of the amino acid to be coupled (Hudson D., *J. Org. Chem.* (1988) 53,617–624). The third step is capping (with acetic anhydride) of any unreacted alpha amino groups so they are blocked from reaction in latter addition cycles. Synthesis occurs by repeating this cycle for each amino acid added to the peptide.

Cleavage of the peptide from the resin and deprotecting of the t-butyl side chain can be accomplished at room temperature in 95% TFA with appropriate scavengers to suppress tert-butylation caused by the generation of tert-butyl trifluroacetate.

Appropriate scavengers include ethanethiol, phenol and thioanisole. The reaction time is 16 hr. for the amide resin and 3 hr. for the Wang resin.

Solid Phase Peptide Synthesis (Cyclization)

There are two major schemes in which to use solid phase peptide synthesis to make the cyclic polypeptide of the; present invention. The more traditional is to cyclize the peptide in solution after it has been cleaved from the resin and purified (for reviews—Kopple, K. D., *J. Pharmol. Sci.* (1972) 61, 1345–1356; Blout, E. R., *Biopolymers* (1981) 20, 1901–1912). Recent advances in solid phase peptide synthesis methodologies has allowed an easier method where the cyclization process can proceed while the peptide is still on the resin (Felix, A. M., et al., *Int. J. Peptide Protein Res.* 1987, 231–238; Schiller, P. W., et al., *Int. J. Peptide Protein Res.* 19.85, 25, 171–177; Buku, A., et al., *J. Protein Chem.* 1985, 4, 163–170; Lebl, M., et al., *Tetrahedron Lett.* 1984, 25, 2067–2068; Hase, S. *J. Am. Chem. Soc.* 1972, 94, 3590–3600; Flanigan, E., et al., *Tetrahedron Lett.* 1970, 2403–2406; Ploux, O., et al. *Int. J. Peptide Protein Res.* 1987, 29,162–169). This latter method obviates the problem of linear oligomer formlation which may occur in solution phase cyclization (even at high dilution). For the synthesis of cyclic peptide analogs of endothelin antagonists, two alternative methods for cyclization on a solid support may be utilized.

An exemplary procedure is depicted in Scheme II.

and has an acid function, the latter protects the other and has an amino function. The peptide is synthesized using the tBoc cycle except the basewash step uses only 1% diisopropylethylamine (DIPEA) instead of the usual 10% after the first amino acid with an Fmoc group is added. The OFm and

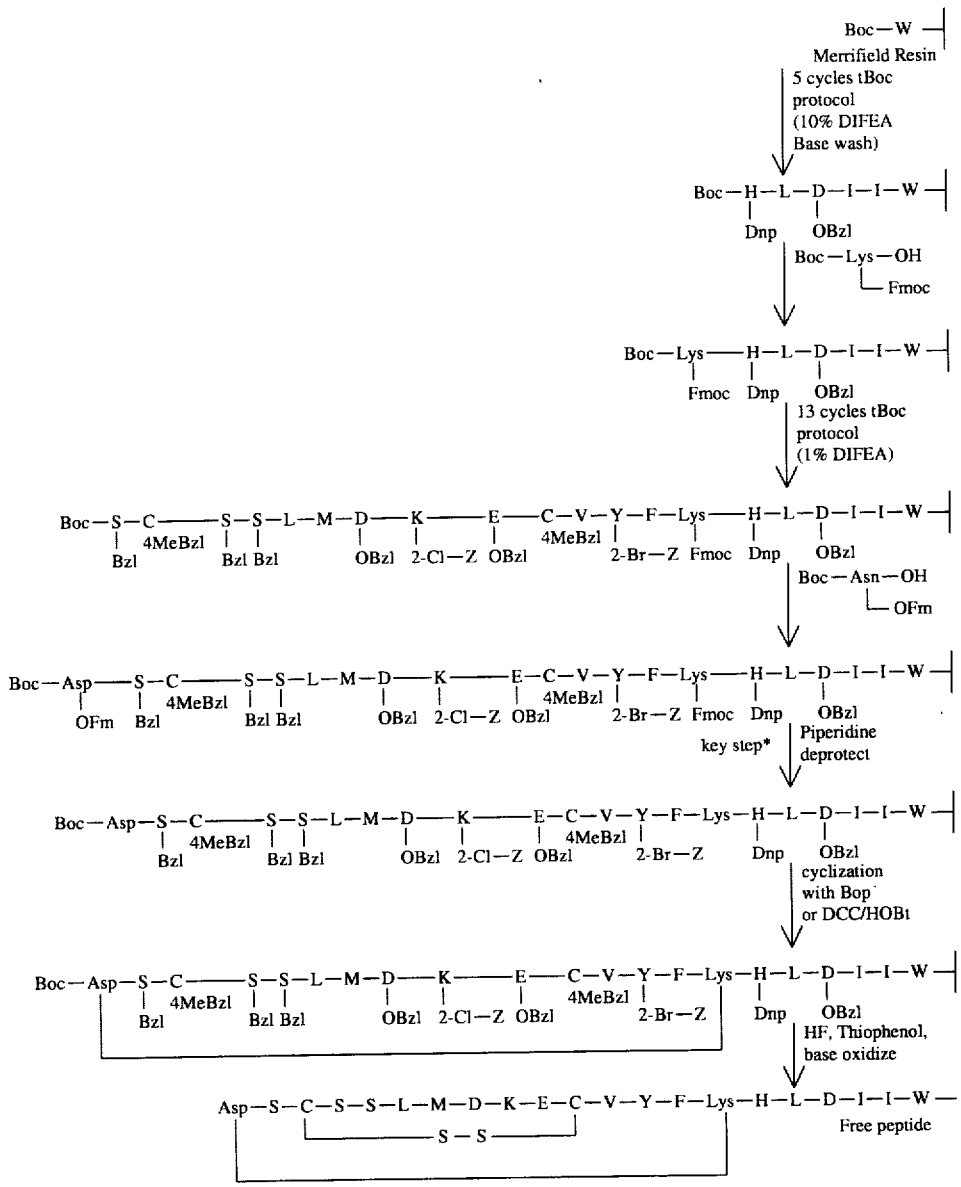

SCHEME II
Cyclization Synthesis Strategy 1

In the above Scheme, Z is benzyloxycarbonyl, Bzl is Benzyl, Me is Methyl, Dnp is 2,4-dinitrophenyl, and Fmoc is as identified in the text.

The first method involves the use of tBoc alpha amino blocking groups and two different types of side chain protecting groups. Most of the side chains are protected by the standard benzyl-based groups of tBoc synthesis. However, in the case when one of the side chains has a free carboxy group and the other has a free amino group, the amino acid side chains are protected with the OFm (9-fluorenylmethyl) or Fmoc (9-fluorenyl-methoxycarbonyl) groups, respectively. The former protects these side chains Fmoc groups have been shown to be stable in this concentration of DIPEA. The key step of this strategy (Scheme 2), occurs after the last amino acid has been added, when the OFm and Fmoc side-chain protecting groups are selectively removed with 20% piperidine in DMG. This results in a peptide still attached to the resin with all reactive side chains protected except the two involved in subsequent cyclization. Cyclization (lactamization) then proceeds through amide bond formation between the acid side chain and the amino side chain, using BOP or DCC/HOBt activation. Thiophenol treatment can then be done to remove the Dnp (2,4-dinitrophenyl) group from His, and HF cleavage can be performed to remove the benzyl-based protecting groups from the side chains along with the peptide from the resin. Finally any remaining cysteine pairs can be oxidized in base to allow disulfide bond formation.

The chemical bridge described in this cyclization strategy (namely a side-chain to side-chain cyclization through replacement of Cys$^1$ with Asp and Cys$^{15}$ with Lys) is depicted hereinbelow.

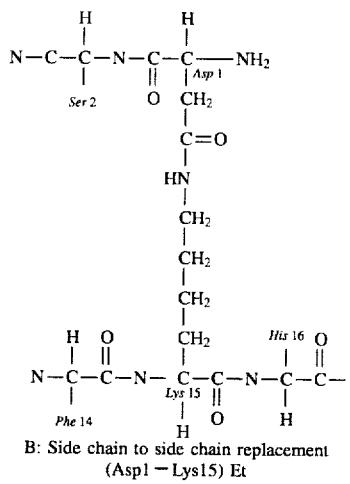

B: Side chain to side chain replacement
(Asp1 — Lys15) Et

Notice there are seven atoms in this bridge as opposed to four in native endothelin. A preferred method of cyclization is through peptide formation under amide forming conditions. In many of the exemplifications described hereinabove, the amide formation took place between the side chain amino group and the side chain carboxy group. Alternatively, the covalent linkage may occur between the amino group at the N-terminus of the polypeptide and the carboxy group on the side chain of the amino alkyl dicarboxylic acid. For example, when the $AA_{15}$ is an amino lower alkyl dicarboxylic acid, such a Glu, the carboxy group on the side chain can react with the free amino group on the N-terminus of $AA_2$ under peptide forming conditions to form the covalent bridge between $AA_1$ and $AA_{15}$.

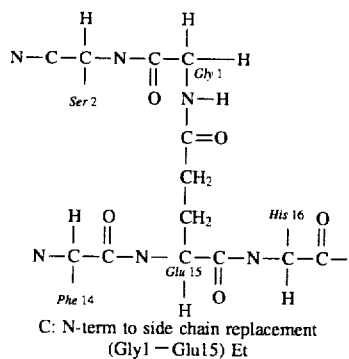

C: N-term to side chain replacement
(Gly1 — Glu15) Et

Notice this bridge matches the four atoms in the native Endothelin bridge, but an amine and carbonyl function (i.e., an amide) are introduced into the bridge. Also notice the free N-terminal NH$_2$ group is replaced by a hydrogen atom. This may be a general advantage of the side-chain to N-terminus cyclization approach, since cyclization can be easily monitored by loss of reactivity with ninhydrin reagent.

In a more general example of the above scheme, the carboxy group on the side chain can react with the amino group on $AA_2$ to form the dipeptide and thereby bridge $AA_{15}$ to the moiety at $AA_1$ as follows:

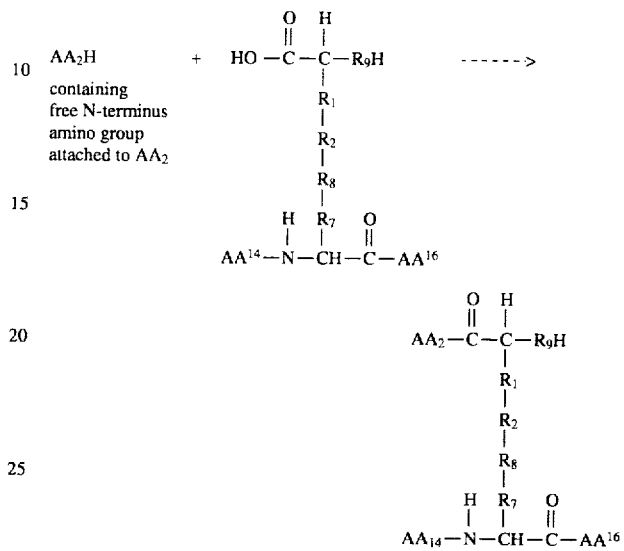

wherein $R_9$, $R_1$, $R_2$, $R_8$, $R_7$, $AA_2$, $AA_{14}$ and $AA_{16}$ are as defined hereinabove.

For example, if $AA_{15}$ is 1, 6-aminosuberic acid, i.e., $R_1$, $R_2$, $R_7$ and $R_8$ are CH$_2$ and $R_{13}$ is H, then the carboxy group on the omega position can form the amide linkage with the amino group on $AA_2$ (e.g., Ser).

In this method the bridging atoms are present in the bridging linkage, $R_7$-$R_8$-$R_2$-$R_1$, and the reaction is the formation of the amide linkage between the first and second amino acids from the N-terminus of the polypeptide. Thus, using this method, the following groups can be part of the bridging atoms: thioethers, ketones, esters, alkenes, amine, aryl, cycloalkyl, aryl lower alkyl and cycloalkyl lower alkyl groups.

Functional groups at $R_9$ would, of course, require substitution with protective groups prior to the cyclization step. For example, an amino function in this position may be protected by acylation with such protecting group as Fmoc or Tboc or by substitution with other protecting groups resistant to cleavage by the piperidine or 50% TFA deprotection steps but which are cleaved by the final side chain group deprotection steps.

Amino acids with unusual combinations of side chain and N-terminal protecting groups are commercially available from such vendors as Advance ChemTech, MilliGen/Biosearch, and Bachem. Also many unusual amino acid derivatives are also commercially available or can be custom made by Bachem.

An alternative chemical approach (see Schiller, P-W., et al., *Int. J. Peptide Protein Res.* op. cit.) involves using Fmoc alpha amino protected amino acids and Boc and tert-butyl protection for the side-chains of Lys and Glu, respectively as described in Scheme III.

SCHEME III
Cyclization Synthesis Strategy 2

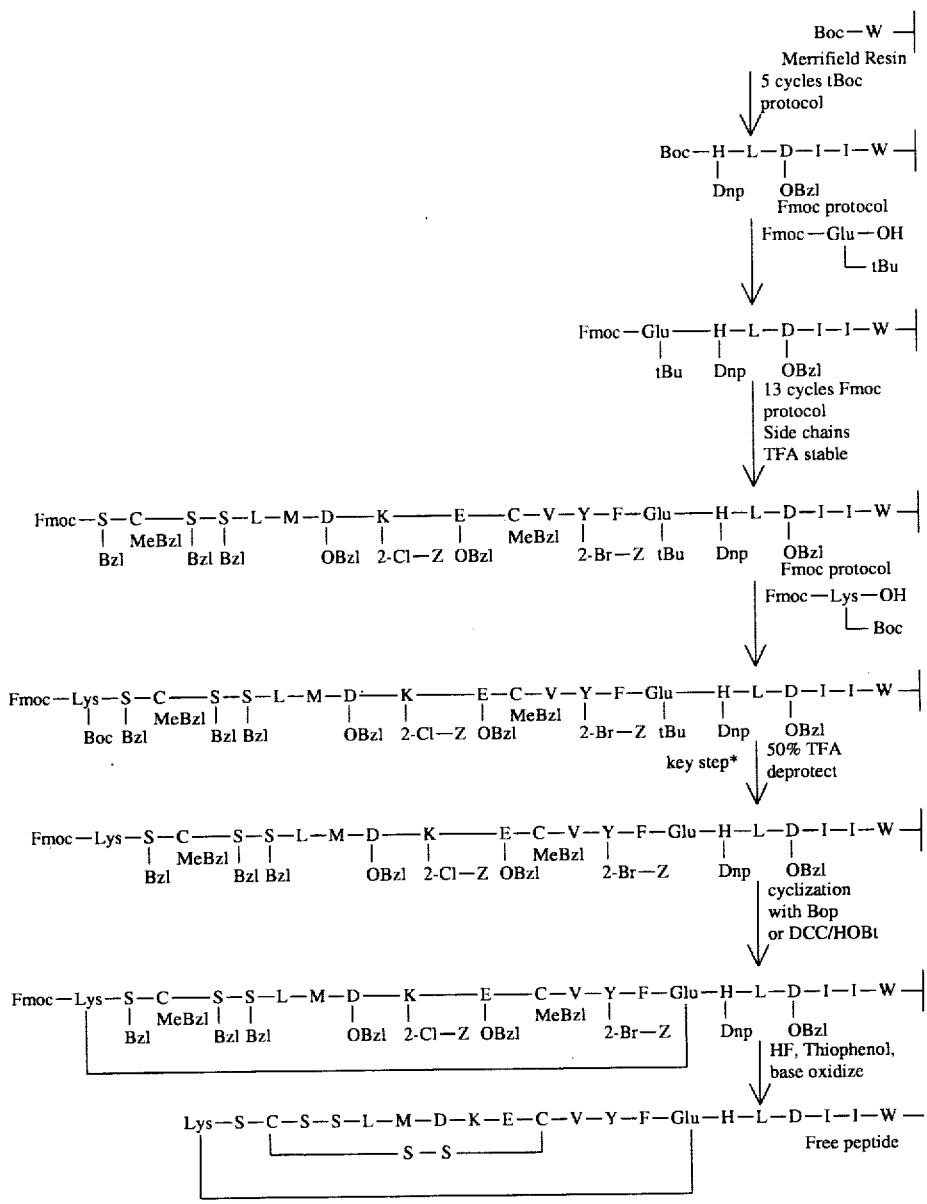

Residues between the Lys and Glu to be cyclized are side-chain protected by TFA stable groups. Fmoc synthesis strategy is used to couple the amino acids involved in the loop structure.

Again the key step in the procedure (starred arrow) is the selective removal of just the side-chain protecting groups of the amino acids involved in cyclization (in this case Lys and Glu). After removal of the Lys and Glu side chain protection by TFA treatment, cyclization on the resin can be performed through amide bond formation between the side chain amino and carboxyl groups with an appropriate coupling reagent. The formation of this cyclic structure may be preceded or followed by peptide chain assembly using tBoc amino acids and tBoc protocol, and the entire peptide chain containing the cyclic portion is finally cleaved by HF treatment. As in cyclization strategy 1, the Lys and Glu side chains can be replaced with other amino acid side chains and the method can be adapted to side-chain to N-terminal cyclization. This approach has the advantage that Fmoc N-terminal protected amino acids with tBoc or butyl based side chain protecting groups are routinely used in standard synthesis, and thus readily available and inexpensive.

The methods described hereinabove can be used to link the bridging atoms connecting $R_{13}$ and $R_{15}$ (or $AA_3$ and $AA_{11}$). Since the peptide is prepared from the C-terminus end, the peptide can first be synthesized by synthesizing the polypeptide up to $AA_3$ and forming the bridge between $AA_3$ and $AA_{11}$ in accordance with the procedure described hereinabove. Then once the bridge is formed, the amino acid residues can be added to the N-terminus of $AA_3$, and the polypeptide chain can be lengthened until the desired product is formed.

Techniques to monitor cyclization include quantitative ninhydrin and analytical reverse phase HPLC.

Peptide Purification

The purity of the products obtained after acid cleavage is usually reasonably good, but some purification is required. The purification of the peptides can be described as a three part process. The three steps are extraction from the resin, gel filtration, and reverse phase high performance liquid chromatography. After cleavage, the resin containing the peptide is washed with ethyl acetate to remove organic contaminants present in the synthesis and cleavage. Cyclohexane washes are used for endothelin antagonists because its highly hydrophobic nature causes loss of peptide in ethyl acetate or ether. The peptide is then extracted from the resin using 1 M acetic acid (AcOH). Most peptides will not be soluble in EtOAc but will be soluble in 1M AcOH. If the peptide is not soluble in 1 M AcOH, then glacial acetic acid or TFA may be used to extract the peptide. It is often necessary to solubilize and extract the peptide in a solution of guanidine hydrochloride or urea. The second step in the process of peptide purification is gel filtration. The crude product is applied to a Sephadex G-25 column in 0.1M AcOH. The fractions containing peptide are pooled and lyophilized. Gel filtration is used to remove low molecular weight contaminants from the peptide.

The third step in peptide purification is reverse phase high performance liquid chromatography (rp HPLC). Reverse phase HPLC uses nonpolar groups (C18) bonded to the column and utilizes aqueous buffers containing either methanol or acetonitrile, each with 0.1% trifluoroacetic acid (TFA). For detection, absorbance at 254 nm may be used for peptides containing aromatic residues. Peptides without aromatic residues may be monitored at 214 nm. Reverse phase HPLC is used to separate the desired peptide from failure peptide sequences and may be useful in the separation of linear peptides from cyclic ones. The retention of a peptide in reverse phase HPLC depends upon the number, size and sterochemistry of the hydrophobic and hydrophilic residues in the peptide. The interaction of side chains with the nonpolar stationary phase combined with interactions with the mobile phase determine the retention time for peptides in RP HPLC.

The final assay for peptide purity is thin layer chromatography (TLC) on silica gel. As many as six solvent systems may be used to check for peptide purity (Yamaguchi, I., et al., *Acta Chemica Scandinavica* (1979) 33, 63–68. The use of different detection reagents gives greater sensitivity to TLC (Glazer, A. N., et al., *Laboratory Techniques in Biochemistry and Molecular Biology: Chemical Modification of Proteins*, North-Holland Publishing Co., (1975)). A number of detection methods are used during routine assay for purity by TLC. Ninhydrin can be used to detect peptides with alpha amino groups exposed. Ninhydrin is a reasonably sensitive technique and can detect as little as 100 µg of peptides (see Kaiser, E., et al., *Anal. Biochem.* op. cit.). Ninhydrin cannot detect peptides that have no alpha amino groups (such as peptides where the N-terminus is involved in cyclization) or very low levels of peptide, so other detection techniques may be used. Hypochlorite reagent (Mazur, R. H., et al., *J. Biol. Chem.* 237, 1619 (1962)) is used to detect substances that contain N-H bonds. Hypochlorite detection is very sensitive and should detect all peptides. Other reagents can be used to detect specific amino acids contained in the peptides although these methods are not very sensitive. Sakaguchi reagent (see Glazer, A. N., et al., *Laboratory Techniques in Biochemistry and Molecular Biology: Chemical Modification of Proteins* op. cit.) is used to detect peptides containing arginine residues. Ehrlich's (see Glazer, A. N., et al., *Laboratory Techniques in Biochemistry and Molecular Biology: Chemical Modification of Proteins* op. cit.) reagent can be used to detect tryptophan containing peptides and Pauly reagent (see Glazer, A. N., et al., *Laboratory Techniques in Biochemistry and Molecular Biology: Chemical Modification of Proteins* op. cit.) can be used for the detection of histidine and tyrosine residues. If the peptide obtained from reverse phase HPLC migrates in a single spot in all TLC systems used, and with several detection methods shows the same single spot, then the peptide may be considered pure.

The various amino acid moieties, including $AA_1$–$AA_{21}$ defined herein may exist in either the D or L stereoismeric form. The various enantiomers, diastereomers and mixtures thereof are contemplated by the present invention. It is preferred, however, that the various $AA_1$–$AA_{21}$ are in the L-form.

The present new compounds form salts with acids when a basic amino function is present and salts with bases when an acid function, i.e., carboxy, is present. All such salts may be useful in the isolation and/or purification of the new products. Of particular value are the pharmaceutically acceptable salts with both acids and bases. Suitable acids include, for example, hydrochloric, sulfuric, nitric, benzenesulfonic, toluenesulfonic, acetic, malic, tartaric and the like which are pharmaceutically acceptable. Basic salts for pharmaceutical use are the Na, K, Ca and Mg salts.

The compounds of the present invention can be administered to the host in a variety of forms adapted to the chosen route of administration, i.e., oral, rectal, intravenous, intranasally, intramuscular or subcutaneous routes, or by inhalation or insufflation.

The active compound may be orally administered, for example, with an inert diluent or with an assimilable edible carrier, or it may be enclosed in hard or soft shell gelatin capsules, or it may be compressed into tablets. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both.. A syrup of elixir may contain the active compound, sucrose as a sweetening agent, methyl and propylparbens as preservatives, a dye as flavoring such as cherry or orange flavor.

Of course, any material used in preparing any dosage unit form should be pharmaceutically pure and substantially non-toxic in the amounts employed. In addition, the active compound may be incorporated into sustained-release preparations and formulations.

A suitable route of administration of the antagonists of the present invention is intramuscularly or intraperitoneally. Solutions of the active compound as a free base, free acid or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. It is contemplated that an especially effective mode of administration via these routes will be in a controlled release form wherein the rate of release of the antagonist is controlled by the dissolution rate of an encapsulant, diffusion rate of the antagonist through a membrane or compounding matrix and the like.

The most preferred route of administration is by intravenous injection. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such a lecithin, by the maintenance of the required particle size, in the case of dispersions, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients entunerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

For administration by inhalation, the compounds according to the present invention are conveniently delivered in the form of an aerosol spray presentation from pressurized packs, with the use of a suitable propellant, such as dichlorodifluoromethane, trichlorofluoromethane, dichlorotetrafluoroethane, carbon dioxide or other suitable gas, or from a nebuliser. In the case of a pressurized aerosol, the dosage unit may be determined by providing a valve to deliver a metered amount. Alternatively, for administration by inhalation or insufflation, the compounds of the present invention may take the form of a dry powder composition, for example, a powder mix of the compound and a suitable powder base such as lactose or starch. The powder composition may be presented in unit dosage form in for example capsules or cartridges of e.g., gelatin or blister packs from which the powder may be administered with the aid of an inhaler or insufflator.

The active compounds are effective over a wide dosage range. For example, in the various pharmaceutical formulations, including intravenous feeding, but excluding those formulations used in administration by means of inhalation, dosages can range from about 0.0001 to about 100 mg per kilogram of animal weight and preferably about 0.01 to about 10 mg per kilogram of animal weight. If the delievery system is through inhalation, it is preferable that the dosage ranges from about 0.001 to about 50 mg of active ingredient per kilogram of animal weight and more preferably from about 0.01–2 mg of active ingredient per kilogram of animal weight. However, it will be understood that the amount administered and the frequency of administration will be determined by the physician in light of the relevant circumstances, including the condition to be treated, the choice of compound to be administered and the chosen route of administration. Thus, the above dosage ranges are not intended to limit the scope of the invention in any way.

Moreover, the antagonist precursor may be the form that is administered directly to the animal. The precursor is then cleaved by the endothelin converting enzyme in the animal to yield the active compound.

The invention will be further illustrated by the following specific examples.

EXAMPLE 1

This example shows the synthesis of the [$Dpr^1$-$Asp^{15}$] Et-1 analog of Et-1 wherein the outer loop disulfide linkage of Et-1 is replaced by an amide linkage. Specific antagonist activity of the analog is also shown in assays with isolated, perfused guinea pig lung preparation.

[$Dpr^1$-$Asp^{15}$] Et-1 Et-1 was synthesized by a solid phase procedure using a Biosearch Model 9500 peptide synthesizer employing a modified tBoc protocol as outlined in Sheme IV. Briefly, aspartic acid with a fluorenylmethyl ester side chain protecting group was substituted for $Cys^{15}$ of the native endothelin-1 sequence, while $Cys^1$ in native endothelin-1 was replaced by N-alpha-tBoc-N-beta-Cbz-L-diaminopropionic acid (Dachem Bioscience, Philadelphia, Pa.). All other reactive side chains were protected by standard tBoc benzyl-based groups which are removed effectively through HF cleavage. The fully protected peptide was treated with trifluoroacetic acid to remove the N-terminal Boc group and then treated with 20% piperidine to remove the fluorenylmethyl group on $Asp^{15}$ (see Step 1 in Scheme IV)

The partially protected peptide that resulted was cyclized using BOP reagent (Felix, A. M., et al., *Int. J. peptide Protein Res.* 25, 231–238 (1987)) in the presence of 1.5% diisopropylethylamine to form the outer loop amide linkage (Step 2). Cyclization efficiency was 95% as monitored by quantitative ninhydrin reaction (Kaiser, E. et al., *Anal. Biochem*, 34, 595–598 (1970)). The dicyclic product was cleaved by a low/high HF procedure (Tam, J. P. et al. *J. Am Chem. Soc.*, 105, 6442–6455 (1983)) that removes all protecting groups (Step 3). The inner loop disulfide of the crude product was allowed to form through air oxidation in a dilute solution of NaOH, pH 8.3 for 4 hours. Crude product thus obtained was purified by reverse phase HPLC. Quality of syntheses was monitored through amino acid analysis and peptide sequencing.

EXAMPLE 2

The antagonist

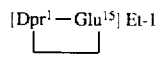

synthesized and purified according to the procedure given in Example 1 with the exception that Glu-Fmoc is substituted for Asp-Fmoc at position 15.

EXAMPLE 3

Using the procedure described in Example 1 and the appropriate amino acids, the following polypeptides can be synthesized:

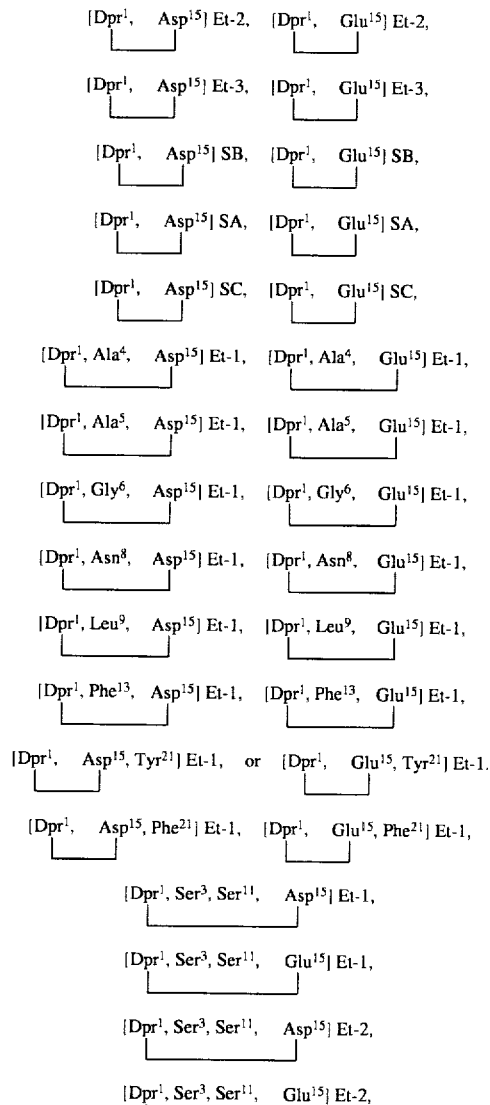

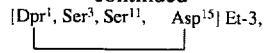
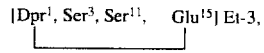
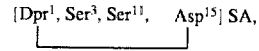
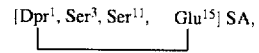
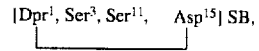
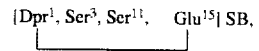
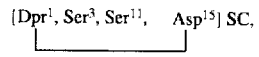
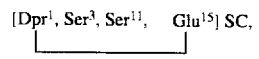
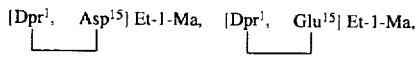
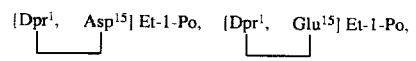
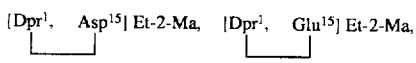
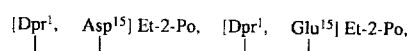
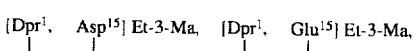
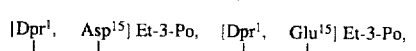
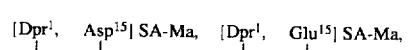
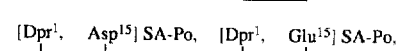
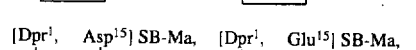
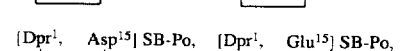
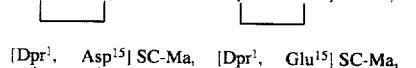
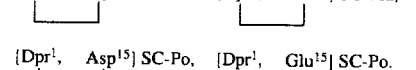

As indicated hereinabove, the compounds of the present invention are endothelin antagonists. Without wishing to be bound, it is believed that the compounds of the present invention compete with endothelins, either competitively or noncompetitvely at the receptor sites. The release of endothelins is implicated with various disorders, such as hypertension, including systemic, pulmonary and hepatic portal hypertension, atherosclerosis, vasospasms, such as cerebral, coronary, artery or pulmonary vasospasms, asthma, and renal failure. With snake bites, it is sarafotoxin release. These disorders are accompanied with vasoconstriction, vasopresser action and/or cell proliferation. As antagonists of endothelin, the compounds of the present invention inhibit endothelin action, thereby alleviating the conditions associated with endothelin or (sarafotoxin) release. Thus, the compounds of the present invention are useful in the treatment and prophylaxis of endothelin mediated disorders listed hereinabove. Furthermore, the compounds of the present invention are useful in the treatment and/or prophylaxis of other endothelin (or sarafotoxin) mediated disorders, such as myocardial infarction, restenosis, unstable angina, stroke and transient ischemic attacks. In addition, these compounds may be administered in effective amounts in conjunction with angioplasty. As endothelin antagonists, the compounds of the present invention are also useful in inhibiting muscle contraction, especially smooth and cardiac muscle. Furthermore, the compounds of the present invention are useful in the prophylaxis and treatmeent of disorders of the respiratory tract associated with smooth muscle contraction (e.g., asthma), disorders of the urinary tract that can be treated by relaxation of smooth muscle in the urinary tract (e.g., acute urinary retention); disorders associated with smooth muscle contraction in the alimentary tract (e.g., emesis, diarrhea and esophageal spasm); disorders that can be treated by relaxing vessels in the venous system (e.g., congestive heart failure).

The compounds of the present invention have potential diagnostic uses, e.g., to improve visualization of coronary arteries. In other words, the physician can administer drugs of the present invention to a patient to relax the arteries so as to enable the physician to visualize them.

The effectiveness of the compounds as an inhibitor of endothelin is an indicator as to its efficacy as a useful drug. Some of these tests were described hereinabove. Another of these tests is described below. In this test, a representative compound of the present invention, viz., $[Dpr^1\text{—}Asp^{15}]$ Et-1, was used.

EXAMPLE 4

The vasoconstrictor activity of Et-1 or Et-3 alone, or in the presence of antagonist, was determined using an isolated, perfused lung preparation (Horgan, M. J., et al. *J. Appl. Phsysiol.*, 63, 93–104 (1987)). Briefly, Hartley guinea pigs (400–500 g) of either sex were anesthetized with 50 mg/kg pentobarbital sodium. Following a tracheotomy, the thorax was opened, the lung and heart excised and the pulmonary artery cannulated. A wide cannula was placed in the left atrium. Perfusion was then started, within 5 min. of opening the thorax. The perfusion flow was set at 28 ml/min. When there was no visible sign of blood in the pulmonary venous effluent, recirculation of the perfusate was started, and pulmonary artery pressure was monitored. Endothelin activity was measured in an accumulative dose-dependent manner for agonist activity by addition of the peptides to a recirculating 300 ml bath. To assess antagonist activity, dose response curves with endothelin were done in the constant presence of antagonist.

The graph in the figure demonstrates that in the isolated, perfused guinea pig lung, Et-1 caused a dose-dependent increase in pulmonary artery pressure (Ppa): it is active at $10^{-10}$ M and gives a maximal response at $10^{-8}$ M.

$[Dpr^1\text{—}Asp^{15}]$ Et-1 on the other hand, had essentially no agonist activity even at doses as high as $1\times10^{-6}$ M.

The table below shows the results of antagonist activity determinations wherein changes in pulmonary artery pressure (expressed as experimental value—baseline value) were measured in response to perfusion of guinea pig lung with different concentrations of Et-1 in the perfusion fluid. The response with lungs preperfused, for 5 min. with $[Dpr^1\text{—}Asp^{15}]$ Et-1 at a concentration of $10^{-7}$ M before coperfusion with Et-1 was compared with the response determined on lungs perfused only with Et-1. (Results in both Tables 1 and 2 are based on the average of 4–7 determinations for each result).

TABLE 1

Antagonist Activity $[Dpr^1\text{—}Asp^{15}]$Et-1 versus Et-1 in Perfused Guinea Pig Lung

| Et-1 Conc. | Pressure Increase Ppa (cm H$_2$O) | | Pressure Increase Inhibition (%) |
|---|---|---|---|
| | Without Antagonist | With Antagonist | |
| $10^{-10}$ M | 1.2 | 0.06 | 95 |
| $2 \times 10^{-10}$ M | 2.3 | 0.6 | 75 |
| $10^{-9}$ M | 6.1 | 2.1 | 65 |

Preperfusion/coperfusion of the lung with $[Dpr^1\text{—}Asp^{15}]$ Et-1 at a dose of $10^{-7}$ M substantially decreased response to subsequent doses of endothelin: $10^{-10}$ M Et-1 response was inhibited by 95%, $2\times10^{-10}$ M Et-1 response by 75%, and a $10^{-9}$ M Et-1 response was inhibited, by 65%. Higher doses of the analog did not substantially increase this blocking activity.

Specificity of $[Dpr^1\text{—}Asp^{15}]$ Et-1 is illustrated in Table 2 which presents pressure increase data in similar lung preparations perfused with Et-3 and with other vasoconstrictor substances (alpha-thrombin and norepinephrine). As for the results shown in Table 1, pressure increase was determined on lung preparations with and without a 5 minute preperfusion step with $10^{-7}$ M $[Dpr^1\text{—}Asp^{15}]$ Et-1.

TABLE 2

Effect of $[Dpr^1\text{—}Asp^{15}]$ Et-1 On Pressure Increase

| Vasoconstrictor | Ppa (cm H$_2$O) | |
|---|---|---|
| | Without $[Dpr^1\text{—}Asp^{15}]$ Et-1 | With $[Dpr^1\text{—}Asp^{15}]$ Et-1 |
| Et-3 ($10^{-9}$ M) | 3.8 | 5.8 |
| α-Thrombin ($10^{-8}$ M) | 6.6 | 8.5 |
| Norepinephrine | 1.3 | 1.3 |

TABLE 2-continued

Effect of [Dpr¹—Asp¹⁵] Et-1 On Pressure Increase

| | Ppa (cm H₂O) | |
|---|---|---|
| Vasoconstrictor | Without [Dpr¹—Asp¹⁵] Et-1 | With [Dpr¹—Asp¹⁵] Et-1 |
| ($10^{-7}$ M) | | |

The data in Table 2 indicate no antagonist activity displayed by [Dpr¹—Asp¹⁵] in lung preparations treated with potent vasoconstricting substances other than Et-1. Taken together, the data in Tables 1 and 2 illustrate a high degree of specificity for the endothelin antagonist of the present invention.

The above embodiments and examples are given to illustrate the scope and spirit of the instant invention. Thse embodiments and examples will make apparent, to those skilled in the art, other embodiments and examples. These other embodiments and examples are within the contemplation of the present invention. Therefore, the present invention should be limited only by the appended claims.

---

What is claimed is:

1. A compound selected from the group consisting of:

[Dpr$^1$, Asp$^{15}$] Et-1, [Dpr$^1$, Asp$^{15}$] Et-2, [Dpr$^1$, Asp$^{15}$] Et-3,

[Dpr$^1$, Asp$^{15}$] SB, [Dpr$^1$, Asp$^{15}$] SA, and [Dpr$^1$, Asp$^{15}$] SC.

2. The compound according to claim 1 which is

[Dpr$^1$, Asp$^{15}$] Et-1.

3. The compound according to claim 1 which is

[Dpr$^1$, Asp$^{15}$] Et-2.

4. The compound according to claim 1 which is

[Dpr$^1$, Asp$^{15}$] Et-3.

5. The compound according to claim 1 which is

[Dpr$^1$, Asp$^{15}$] SB.

6. The compound according to claim 1 which is

[Dpr$^1$, Asp$^{15}$] SA.

7. The compound according to claim 1 which is

[Dpr$^1$, Asp$^{15}$] SC.

8. A pharmaceutical composition comprising a pharmaceutically effective amount of a compound according to any one of claim 1–7 and a pharmaceutical carrier therefor.

9. A method for the treatment and prophylaxis of endothelin mediated disorders in an animal comprising administering to said animal an effective amount of a compound according to claim 1.

10. The method according to claim 9 wherein the compound is

[Dpr$^1$, Asp$^{15}$] Et-1.

11. The method according to claim 9 wherein the compound is

[Dpr$^1$, Asp$^{15}$] Et-2.

12. The method according to claim 9 wherein the compound is

[Dpr$^1$, Asp$^{15}$] Et-3.

13. The method according to claim 9 wherein the compound is

[Dpr¹, Asp¹⁵] SB.

14. The method according to claim 9 wherein the compound is

[Dpr¹, Asp¹⁵] SA.

15. The method according to claim 9 wherein the compound is

[Dpr¹, Asp¹⁵] SC.

* * * * *

UNITED STATES PATENT AND TRADEMARK OFFICE
CERTIFICATE OF CORRECTION

PATENT NO. : 5,492,892

DATED : February 20, 1996

INVENTOR(S) : T. T. Andersen, et al.

Page 1 of 5

It is certified that error appears in the above-identified patent and that said Letters Patent is hereby corrected as shown below:

Column 4, line 24: after "structure)" insert --.--

Column 4, line 57: after "(CH$_2$)$_2$" delete --].--

Column 4, line 60: after "CH$_3$" insert --].--

Column 5, line 26: "anti" should read --and--

Column 5, line 55: "halve" should read --have--

Column 7, line 14: "S-Alk" should read --S-ALK--

Column 7, line 33: "ALK-S S-ALK" should read --ALK-S, S-ALK--

Column 7, line 49: after "R$_{10}$" insert --is--

Column 8, line 57: before "is" insert --which--

Column 9, line 5: "R $_8$" should read --R$_8$--

Column 11, line 51: "(1989)" should read --(1989))--

UNITED STATES PATENT AND TRADEMARK OFFICE
CERTIFICATE OF CORRECTION

PATENT NO. : 5,492,892

DATED : February 20, 1996

INVENTOR(S) : T. T. Andersen, et al.

It is certified that error appears in the above-identified patent and that said Letters Patent is hereby corrected as shown below:

Column 12, line 9: after "endothelin" delete --.--

Column 13, line 5: after "the" delete --,.--

Column 13, lines 30 & 31: "Set" should read --Ser--

Column 13, line 52: after "at" delete --.--

Column 14, line 25: after "ethylene" insert --.--

Column 14, line 52: "RV" should read --$R_7$--

Column 15, line 9: "cysline" should read --cystine--

Column 15, line 49: "Ash" should read --Asn--

Column 15, lines 55 & 63: "Set" should read --Ser--

Column 16, lines 4, 23 & 56" "Set" should read --Ser--

Column 16, line 15: after "Leu" insert --or--

Column 16, line 19: after "and" delete --.--.

Column 16, line 45 "Ash" should read --Asn--

UNITED STATES PATENT AND TRADEMARK OFFICE
CERTIFICATE OF CORRECTION

PATENT NO. : 5,492,892

DATED : February 20, 1996\

INVENTOR(S) : T.T. Andersen, et al.

It is certified that error appears in the above-identified patent and that said Letters Patent is hereby corrected as shown below:

Column 17, lines 28, 41 and 49: "Set" should read --Ser--

Column 17, line 29: "AA.$_8$" should read --AA$_8$--

Column 17, line 58: "AA$_1$" should read --AA$_{11}$--

Column 17, line 67: "Ash" should read --Asn--

Column 18, line 5: after "Val" delete --.--

Column 18, lines 34-35: "prestoably" should read --presumably--

Column 18, line 55: "(]963)" should read --(1963)--

Column 19, line 15: "$H_2N$" should read --$^+H_2N$--

Column 19, line 20: "$H_2H$" should read --$H_2N$--

Column 19, line 52: after "(1984))" insert --.--

Column 20, line 51: "C.R." should read --G.R.--

Column 20, line 57: after "mixture" insert --.--

UNITED STATES PATENT AND TRADEMARK OFFICE
CERTIFICATE OF CORRECTION

PATENT NO. : 5,492,892

DATED : February 20, 1996

INVENTOR(S) : T. T. Andersen, et al.

It is certified that error appears in the above-identified patent and that said Letters Patent is hereby corrected as shown below:

Column 21, line 53: after "Model" delete --.--

Column 22, line 51: after "the" delete --;--

Column 22, line 61: "19.85" should read --1985--

Column 24, lines 13 & 26: "DIFEA" should read --DIPEA--

Column 24, line 31: "Asn" should read --Asp--

Column 25, line 51: "His 16" should read --His 15--

Column 26, line 57: "P-W." should read --P.W.--

Column 29, line 21: after "and" delete --.--

Column 30, line 64, "both.." should read --both.--

UNITED STATES PATENT AND TRADEMARK OFFICE
CERTIFICATE OF CORRECTION

PATENT NO. : 5,492,892
DATED : February 20, 1996
INVENTOR(S) : T. T. Andersen, et al.

It is certified that error appears in the above-identified patent and that said Letters Patent is hereby corrected as shown below:

Column 32, lines 37 & 42: "[$\underline{\text{Dpr}}^1$-Asp$^{15}$]" should read --[Dpr$^1$ YAsp$^{15}$]--

Column 32, line 42: delete second occurrence of --Et-1--

Column 33 line 14: before "synthesized" insert --is--

Column 35, line 61: after "and" delete --,--

Signed and Sealed this

Sixteenth Day of September, 1997

BRUCE LEHMAN

Attest:

Attesting Officer

Commissioner of Patents and Trademarks